(12) United States Patent
Lyon et al.

(10) Patent No.: US 12,186,483 B2
(45) Date of Patent: Jan. 7, 2025

(54) SYSTEMS AND METHODS FOR CATEGORIZING AND/OR CHARACTERIZING A USER INTERFACE

(71) Applicant: RESMED SENSOR TECHNOLOGIES LIMITED, Dublin (IE)

(72) Inventors: Graeme Alexander Lyon, Dublin (IE); Roxana Tiron, Dublin (IE); Niall Andrew Fox, Dublin (IE); Redmond Shouldice, Dublin (IE)

(73) Assignee: RESMED SENSOR TECHNOLOGIES LIMITED, Dublin (IE)

( * ) Notice: Subject to any disclaimer, the term of this patent is extended or adjusted under 35 U.S.C. 154(b) by 0 days.

(21) Appl. No.: 18/000,771

(22) PCT Filed: Jun. 7, 2021

(86) PCT No.: PCT/IB2021/054999
§ 371 (c)(1),
(2) Date: Dec. 5, 2022

(87) PCT Pub. No.: WO2021/250553
PCT Pub. Date: Dec. 16, 2021

(65) Prior Publication Data
US 2024/0033457 A1 Feb. 1, 2024

Related U.S. Application Data

(60) Provisional application No. 63/108,161, filed on Oct. 30, 2020, provisional application No. 63/036,303, filed on Jun. 8, 2020.

(51) Int. Cl.
*A61M 16/00* (2006.01)
*G16H 40/63* (2018.01)

(52) U.S. Cl.
CPC .......... *A61M 16/024* (2017.08); *G16H 40/63* (2018.01); *A61M 2205/3375* (2013.01); *A61M 2205/6009* (2013.01)

(58) Field of Classification Search
CPC .............. A61M 16/024; A61M 16/026; A61M 2205/14; A61M 2205/15;
(Continued)

(56) References Cited

U.S. PATENT DOCUMENTS 5,245,995 A 9/1993 Sullivan et al.
6,502,572 B1 1/2003 Berthon-Jones et al.
(Continued)

FOREIGN PATENT DOCUMENTS

WO 2008/138040 A1 11/2008
WO 2010/091462 A1 8/2010
(Continued)

OTHER PUBLICATIONS

Ayappa et al., "Non-Invasive Detection of Respiratory Effort-Related Arousals (RERAs) by a Nasal Cannula/Pressure Transducer System", NYU School of Medicine; published in Sleep, vol. 23, No. 6, 2000, pp. 763-771.
(Continued)

*Primary Examiner* — Joseph D. Boecker
*Assistant Examiner* — Brian T Khong
(74) *Attorney, Agent, or Firm* — NIXON PEABODY LLP

(57) ABSTRACT

Systems and methods are disclosed for categorizing and/or characterizing a user interface. The systems and methods include generating acoustic data associated with an acoustic reflection of an acoustic signal, the acoustic reflection being indicative of, at least in part, one or more features of a user interface coupled to a respiratory therapy device via a conduit. The systems and methods further include analyzing the generated acoustic data. The systems and methods
(Continued)

further include categorizing and/or characterizing the user interface based, at least in part, on the analyzed acoustic data.

38 Claims, 24 Drawing Sheets

(58) Field of Classification Search
CPC .. A61M 2205/6018; A61M 2205/3375; A61M 2205/6009; A61M 2039/1044; A61B 5/7257; G16H 40/63
See application file for complete search history.

(56) References Cited

U.S. PATENT DOCUMENTS

| | | | |
|---|---|---|---|
| 9,358,353 B2 | 6/2016 | Armitstead et al. | |
| 10,492,720 B2 | 12/2019 | Phillips et al. | |
| 10,549,053 B2 | 2/2020 | Armitstead et al. | |
| 10,660,563 B2 | 5/2020 | McDarby et al. | |
| 2005/0005935 A1* | 1/2005 | Gradon | A61M 16/024 128/204.23 |
| 2006/0064037 A1* | 3/2006 | Shalon | G16H 20/60 128/903 |
| 2008/0281219 A1* | 11/2008 | Glickman | A61M 16/024 600/533 |
| 2011/0313689 A1* | 12/2011 | Holley | A61M 16/026 702/56 |
| 2014/0025378 A1* | 1/2014 | Aleksic | G10L 17/00 704/249 |
| 2017/0311879 A1 | 11/2017 | Armitstead et al. | |
| 2018/0075849 A1* | 3/2018 | Khoury | G10L 15/16 |
| 2019/0298271 A1* | 10/2019 | Zigel | A61B 5/4818 |
| 2020/0197640 A1 | 6/2020 | Armitstead et al. | |
| 2020/0337634 A1 | 10/2020 | McDarby et al. | |
| 2020/0383580 A1 | 12/2020 | Shouldice et al. | |
| 2021/0150873 A1 | 5/2021 | Shouldice et al. | |

FOREIGN PATENT DOCUMENTS

| | | |
|---|---|---|
| WO | 2014/047310 A1 | 3/2014 |
| WO | 2016/061629 A1 | 4/2016 |
| WO | 2017/132726 A1 | 8/2017 |
| WO | 2018/050913 A1 | 3/2018 |
| WO | 2019/006496 A1 | 1/2019 |
| WO | 2019/122413 A1 | 6/2019 |
| WO | 2019/122414 A1 | 6/2019 |
| WO | 2020/104465 A2 | 5/2020 |
| WO | 2020/220091 A1 | 11/2020 |
| WO | 2022/091034 A1 | 5/2022 |

OTHER PUBLICATIONS

Written Opinion in International Patent Application No. PCT/IB2021/054999 mailed Sep. 1, 2021 (6 pp.).
International Search Report in International Patent Application No. PCT/IB2021/054999 mailed Sep. 1, 2012 (3 pp.).

* cited by examiner

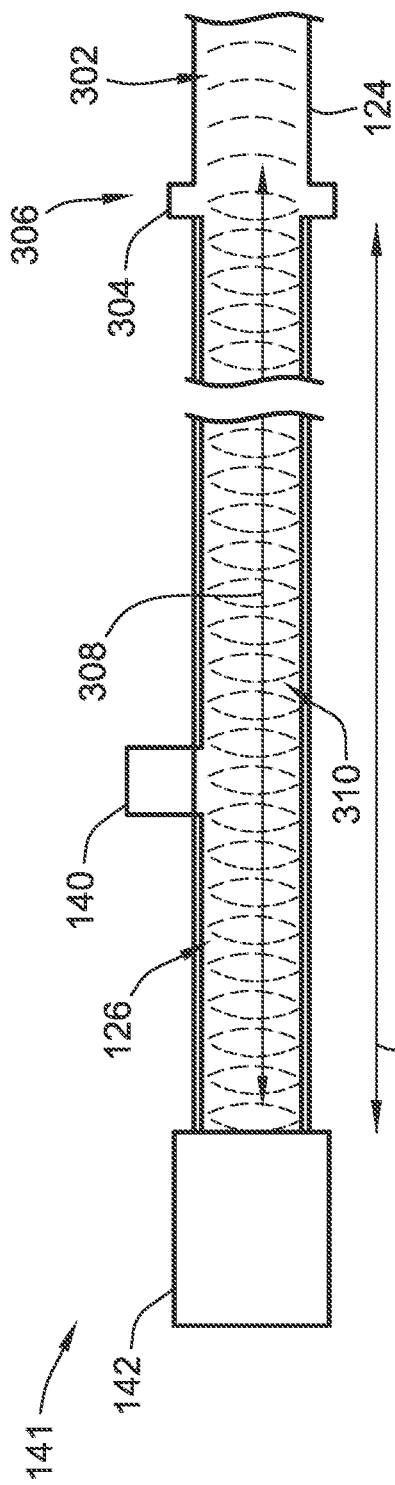
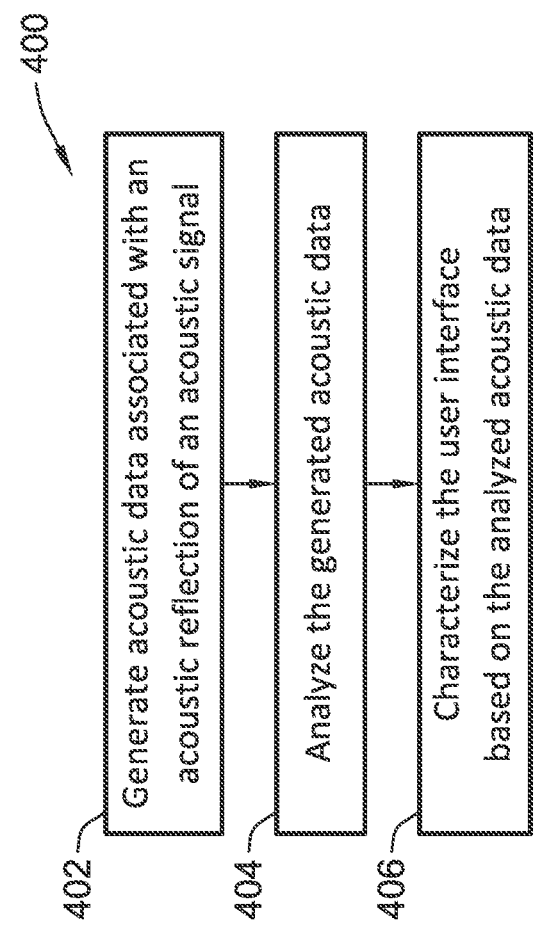

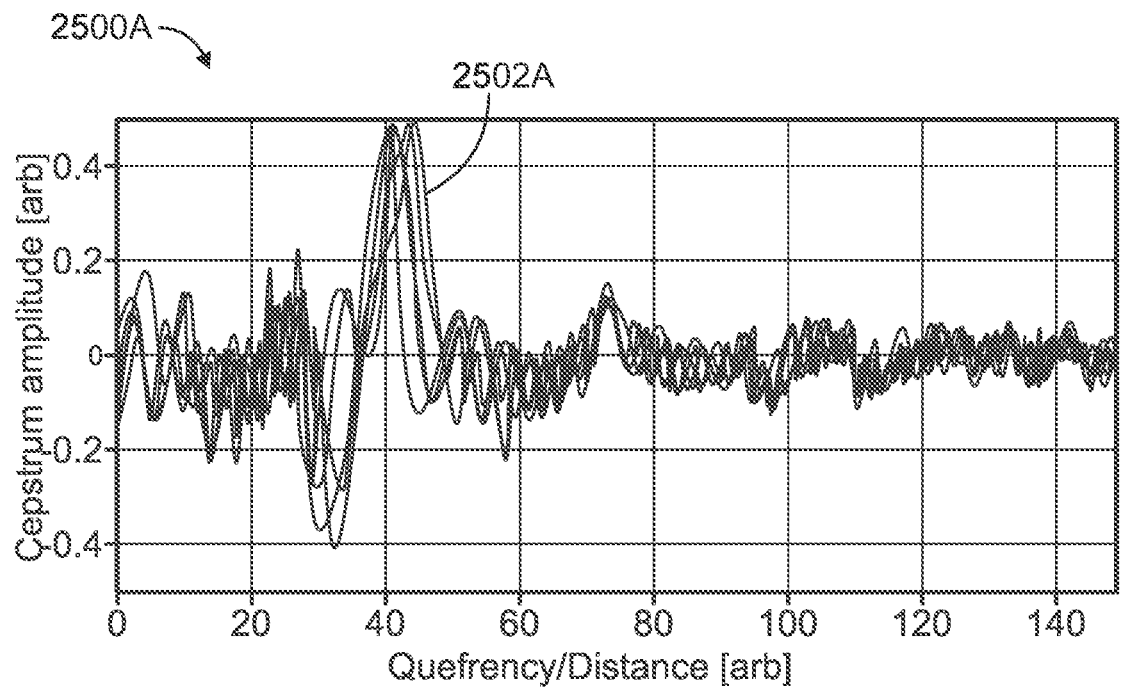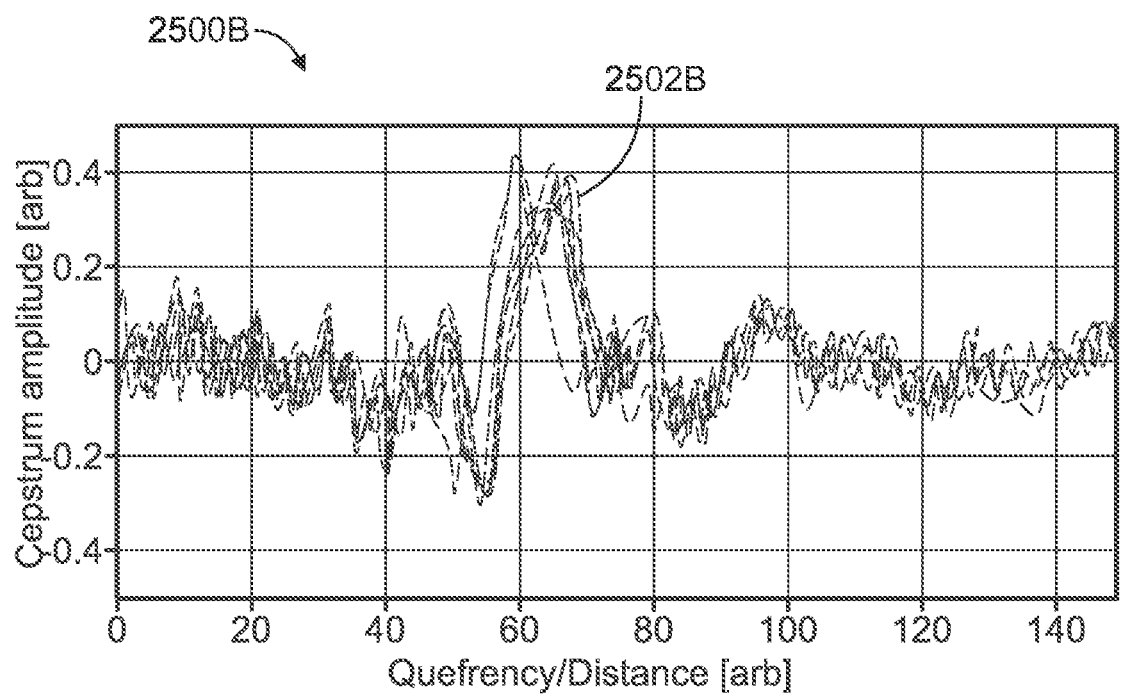
FIG. 25A

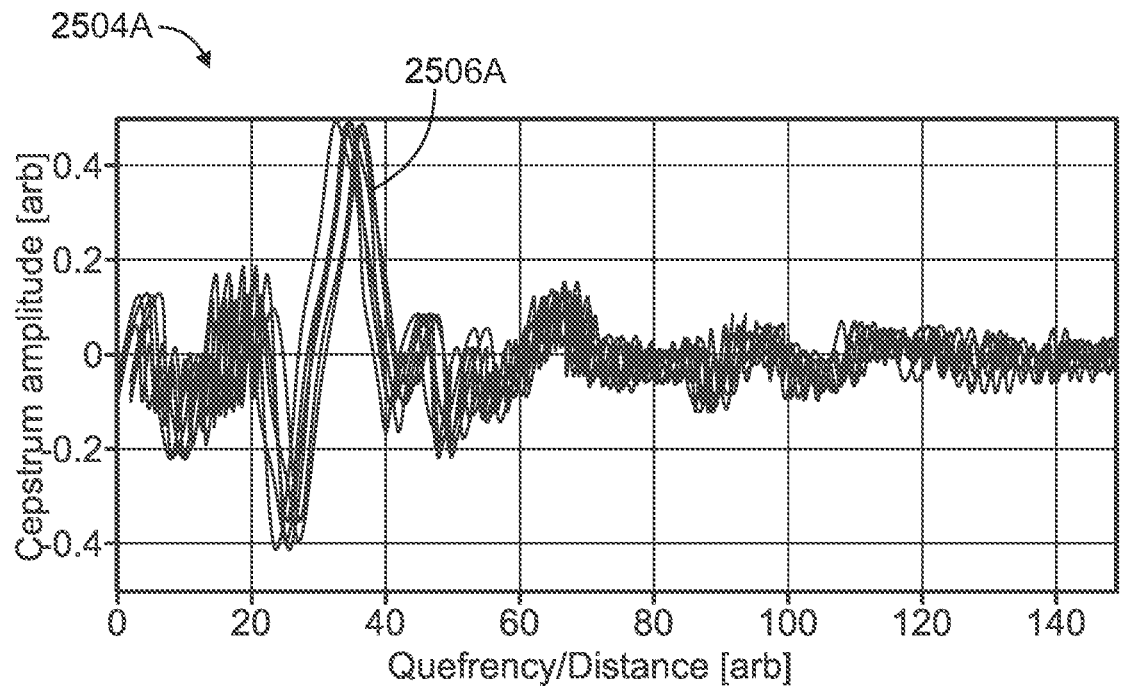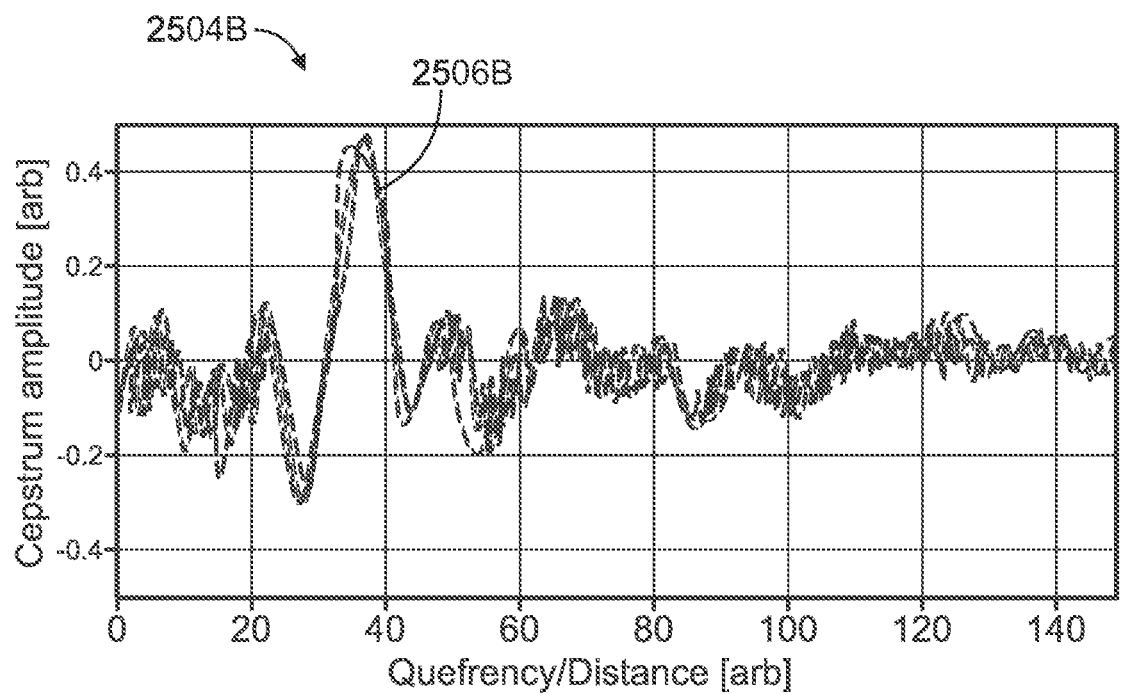
FIG. 25B

SYSTEMS AND METHODS FOR CATEGORIZING AND/OR CHARACTERIZING A USER INTERFACE

CROSS-REFERENCE TO RELATED APPLICATIONS

This application is a U.S. National Stage of International Application No. PCT/IB2021/054999, filed on Jun. 7, 2021, which claims the benefit of, and priority to, U.S. Provisional Patent Application No. 63/108,161 filed on Oct. 30, 2020, and U.S. Provisional Patent Application No. 63/036,303 filed on Jun. 8, 2020, each of which is hereby incorporated by reference herein in its entirety.

TECHNICAL FIELD

The present disclosure relates generally to systems and methods for categorizing and/or characterizing a user interface, and more particularly, to systems and methods for categorizing and/or characterizing a user interface based on an acoustic reflection of an acoustic signal.

BACKGROUND

Many individuals suffer from sleep-related and/or respiratory disorders such as, for example, Periodic Limb Movement Disorder (PLMD), Restless Leg Syndrome (RLS), Sleep-Disordered Breathing (SDB), such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, insomnia, and chest wall disorders. These disorders are often treated using a respiratory therapy system. Respiratory therapy systems can be used to treat sleep-disordered breathing conditions. Each respiratory therapy system generally has a respiratory therapy device connected to a user interface (e.g., a mask) via a conduit. The user wears the user interface and is supplied a flow of pressurized air from the respiratory therapy device via the conduit.

The user interface generally is a specific category and type of user interface for the user, such as direct or indirect connections for the category of user interface, and full face mask, a partial face mask (e.g., a mask which covers the mouth but does not cover the nose or only covers a portion of the nose), nasal mask, or nasal pillows for the type of user interface. In addition to the specific category and type, the user interface generally is a specific model made by a specific manufacturer. For various reasons, such as ensuring the user is using the correct user interface, it can be beneficial for the respiratory therapy system to know the specific category and type, and optionally specific model, of the user interface worn by the user.

A variety of different user interfaces can be used, such as nasal pillows, a nasal mask, a nose and mouth mask (e.g., a full face mask or a partial face mask), etc. In some implementations, different forms of air delivery conduit may be used. It is advantageous to know the user interface and conduit connected to a respiratory therapy device for providing improved control of therapy delivered to the user. For instance, it may be advantageous to the measurement or estimation of treatment parameters, such as pressure in the mask and vent flow. Accordingly, knowledge of what user interface is being used can enhance therapy.

Although respiratory devices may include a menu system that allows a user to enter the type of user interface being used, e.g., by type, model, manufacturer, etc., the user may enter incorrect or incomplete information.

The present disclosure is directed to solving these and other problems by categorizing and/or characterizing a user interface based on analyzed acoustic data generated from an acoustic reflection indicative of one or more features of the user interface.

SUMMARY

According to some implementations of the present disclosure, a method includes generating acoustic data associated with an acoustic reflection of an acoustic signal. The acoustic reflection is indicative of, at least in part, one or more features of a user interface coupled to a respiratory therapy device via a conduit. The method further includes analyzing the generated acoustic data. The analyzing includes windowing the generated acoustic data based, at least in part, on at least one feature of the one or more features of the user interface. The method further includes characterizing the user interface based, at least in part, on the analyzed acoustic data.

According to some aspects of the method, the windowing of the generated acoustic data includes determining a fiducial point in the generated acoustic data. According to some aspects of the method, the fiducial point is a minimum point within a predetermined section of a deconvolution of the generated acoustic data. According to some aspects of the method, the fiducial point is a maximum point within a predetermined section of a deconvolution of the generated acoustic data. According to some aspects of the method, the fiducial point corresponds to a location of the one or more features along a pathway formed, at least in part, by the conduit and the user interface. According to some aspects of the method, the one or more features cause a change in acoustic impedance. According to some aspects of the method, the change in the acoustic impedance is based, at least in part, on a narrowing of the pathway at (i) the user interface, (ii) a junction of the conduit and the user interface, or (iii) a combination thereof. According to some aspects of the method, the change in the acoustic impedance is based, at least in part, on a widening of the pathway at (i) the user interface, (ii) a junction of the conduit and the user interface, or (iii) a combination thereof. According to some aspects of the method, the windowing includes a first windowing of the generated acoustic data and a second windowing of the generated acoustic data. According to some aspects of the method, the first windowing and the second windowing vary by an amount of the generated acoustic data selected before a fiducial point in the generated acoustic data, after the fiducial point in the generated acoustic data, or a combination thereof. The amount of the generated data can be a predetermined number of data points/samples, a predetermined distance, a predetermined quefrency, etc. According to some aspects of the method, the analyzing of the generated acoustic data includes calculating a deconvolution of the generated acoustic data prior to the windowing of the generated acoustic data. According to some aspects of the method, the deconvolution of the generated acoustic data includes calculating a cepstrum of the generated acoustic data. According to some aspects of the method, the cepstrum identifies a distance associated with the acoustic reflection, the distance indicating a location of the one or more features of the user interface along an acoustic pathway travelled by the acoustic signal and relative to an acoustic sensor. The cepstrum can identify one or more distances associated with each of a corresponding one or more acoustic reflections, thereby indicating a location of each of one or more physical features along the acoustic pathway of the acoustic signal. According to some aspects of the method, the analyzing of the generated acoustic data includes calculating a derivative of the cepstrum to determine a rate of change of the cepstrum signal. According to some aspects of the method, the analyzing of the generated acoustic data includes normalizing the generated acoustic data. According to some aspects of the method, the normalizing of the generated acoustic data includes subtracting a mean value from the generated acoustic data, dividing by a standard deviation of the generated acoustic data, or a combination thereof. According to some aspects of the method, the normalizing of the generated acoustic data accounts for confounding conditions. According to some aspects of the method, the confounding conditions are attributed to microphone gain, breathing amplitude, therapy pressure, or a combination thereof. According to some aspects of the method, the characterizing of the user interface includes inputting the analyzed acoustic data into a machine learning model. In one or more implementations, the machine learning model can be supervised or unsupervised. In one or more implementations, the machine learning model can be a neural network. In one or more implementations, the neural network can be a deep neural network or a shallow neural network. In one or more implementations, the deep neural network can be a convolutional neural network. The machine learning model, such as the deep neural network, or the convolutional neural network, can determine a form factor of the user interface, a model of the user interface, a size of one or more elements of the user interface, or a combination thereof. According to some aspects of the method, the deep neural network includes one or more convolutional layers and one or more max pooling layers. According to some aspects of the method, the convolutional neural network includes N features with a max pooling of M samples of the N features, and the ratio of N to M is 1:1 to 4:1. According to some aspects of the method, the method further includes emitting the acoustic signal into the conduit connected to the user interface via an audio transducer. According to some aspects of the method, the method further includes emitting the acoustic signal into the conduit via a motor of the respiratory therapy device connected to the conduit. According to some aspects of the method, the acoustic signal is a sound audible to a human. According to some aspects of the method, the acoustic single is a sound inaudible to a human. According to some aspects of the method, the sound is inaudible based on a frequency of the sound, an amplitude of the sound, or a combination thereof. According to some aspects of the method, the acoustic signal is an ultrasonic sound. According to some aspects of the method, the user interface is not connected to a user during the generating of the acoustic data. In this arrangement, certain confounding factors may be avoided, such as a user's breathing or undesired noises emanating from the respiratory therapy device. According to some aspects of the method, the user interface is connected to a user during the generating of the acoustic data. According to some aspects of the method, the method further includes providing a flow of pressurized air through the conduit and into the user interface during the generating of the acoustic data. According to some aspects of the method, the method further includes emitting the acoustic signal in the conduit during an absence of a flow of pressurized air through the conduit and into the user interface. According to some aspects of the method, the generated acoustic data is generated from a plurality of acoustic reflections from a plurality of acoustic signals. According to some aspects of the method, the generated acoustic data is an average of the plurality of acoustic reflections from the plurality of the acoustic signals. This averaging can enhance the signal to noise ratio of the generated acoustic data by suppressing undesirable time varying components or artifacts in the acoustic data.

According to some implementations, a system is disclosed that includes a control system having one or more processors and a memory having stored thereon machine readable instructions. The control system is coupled to the memory, and any of the above aspects can be implemented when the machine executable instructions in the memory are executed by at least one of the one or more processors of the control system.

According to some implementations, a system is disclosed for characterizing a user interface, the system including a control system having one or more processors configured to implement the method of any one of the above aspects.

According to some implementations, a computer program product is disclosed that includes instructions which, when executed by a computer, cause the computer to carry out the method of any one of the above aspects. According to some aspects, the computer program product is a non-transitory computer readable medium.

According to some implementations of the present disclosure, a method includes generating acoustic data associated with an acoustic reflection of an acoustic signal. The acoustic reflection is indicative of, at least in part, one or more features of a user interface coupled to a respiratory therapy device via a conduit. The method further includes analyzing the generated acoustic data to identify one or more signatures that correlate to the one or more features of the user interface. Generally, a signature can be made up of one or more acoustic features within the acoustic data. The method further includes categorizing the user interface based, at least in part, on the one or more signatures.

According to some aspects of the method, the user interface category is associated with a direct connection between the conduit and a cushion and/or frame of the user interface. According to some aspects of the method, the one or more features and the one or more signatures are indicative of the direct connection between the conduit and the cushion and/or frame. According to some aspects of the method, the user interface category is associated with an indirect connection between the conduit and a cushion and/or frame of the user interface. According to some aspects of the method, the one or more features and the one or more signatures are indicative of the indirect connection between the conduit and the cushion and/or frame. According to some aspects of the method, the indirect connection is characterized by a further conduit located, and configured to provide a fluid connection, between the conduit and the cushion and/or frame. According to some aspects of the method, the further conduit is a headgear conduit and the headgear conduit forms part of a headgear for retaining the user interface on the user's face. The headgear conduit is configured to deliver pressurized air from the conduit to the cushion and/or frame. According to some aspects of the method, the further conduit is a user interface conduit which (i) is more flexible than the conduit, (ii) has a diameter smaller than the diameter of the conduit, or both (i) and (ii). The user interface conduit may also have a shorter length than the conduit. The user interface conduit is configured to deliver pressurized air from the conduit to the cushion and/or frame. According to some aspects of the method, the analyzing the generated acoustic data includes calculating a spectrum of the generated acoustic data. According to some aspects of the method, the analyzing the generated acoustic data includes calculating a logarithm of the spectrum. Alternatively, a non-linear operation may be used in place of a logarithm calculation. According to some aspects of the method, the analyzing the generated acoustic data includes calculating a cepstrum of the logarithm spectrum. According to some aspects of the method, the analyzing the generated acoustic data includes: selecting a segment of a logarithm (log) spectrum of the generated acoustic data; calculating a Fourier transform of the segment of the log spectrum; and correlating the one or more features of the user interface to the one or more signatures within the Fourier transform of the segment. According to some aspects of the method, the one or more signatures include a maximum magnitude of the cepstrum, a minimum magnitude of the cepstrum, a standard deviation of the cepstrum, a skewness of the cepstrum, a kurtosis of the cepstrum, a median of an absolute value of the cepstrum, a sum of the absolute value of the cepstrum, a sum of a positive area of the cepstrum, a sum of a negative area of the cepstrum, a fundamental frequency, an energy corresponding to the fundamental frequency, a mean energy, at least one resonant frequency of a combination of the conduit and the user interface, a change in the at least one resonant frequency, a number of peaks within a range, a peak prominence, distance between peaks, or a combination or change in thereof. According to some aspects of the method, the generated acoustic data includes a primary reflection within the acoustic reflection of the acoustic signal. According to some aspects of the method, the generated acoustic data includes a secondary reflection within the acoustic reflection of the acoustic signal. According to some aspects of the method, the generated acoustic data includes a tertiary reflection within the acoustic reflection of the acoustic signal. According to some aspects of the method, the generated acoustic data includes a primary reflection and a secondary reflection within the acoustic reflection of the acoustic signal. According to some aspects of the method, the user interface category associated with a direct connection between the conduit and the cushion and/or frame is categorized as such based on the one or more signatures having a maximum magnitude of the cepstrum larger than a threshold. According to some aspects of the method, the user interface category associated with an indirect connection between the conduit and the cushion and/or frame via a user interface conduit is categorized as such based on the one or more signatures satisfying a threshold number of peaks. According to some aspects of the method, the user interface category associated with an indirect connection between the conduit and the cushion and/or frame via a user interface conduit is categorized as such based on the one or more signatures having a maximum magnitude of the cepstrum less than a threshold. According to some aspects of the method, the user interface category associated with an indirect connection between the conduit and the cushion and/or frame via a headgear conduit is categorized as such based on the one or more signatures having a mean cepstrum value below a threshold. According to some aspects of the method, the categorizing the user interface based, at least in part, on the one or more signatures includes comparing the one or more signatures to one or more known signatures of one or more user interfaces of known categories.

According to some implementations, a system is disclosed that includes a memory storing machine-readable instructions and a control system including one or more processors configured to execute the machine-readable instructions to perform any one or more of the above methods and/or implementations of the methods.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims. Additional aspects of the disclosure will be apparent to those of ordinary skill in the art in view of the detailed description of various embodiments, which is made with reference to the drawings, a brief description of which is provided below.

BRIEF DESCRIPTION OF THE DRAWINGS

The disclosure, and its advantages and drawings, will be better understood from the following description of exemplary embodiments together with reference to the accompanying drawings. These drawings depict only exemplary embodiments, and are therefore not to be considered as limitations on the scope of the various embodiments or claims.

FIG. 5 illustrates the generation of acoustic data in response to an acoustic reflection indicative of one or more features of a user interface, according to some implementations of the present disclosure.

FIG. 6 is a flow diagram of a method for characterizing a user interface, according to some implementations of the present disclosure.

FIG. 25A illustrates a first plot of a cepstrum calculated from acoustic data generated using a first conduit, and a second plot of a cepstrum calculated from acoustic data generated using a second conduit, according to some implementations of the present disclosure.

FIG. 25B illustrates a first plot of a corrected cepstrum based on the first cepstrum of FIG. 25A, and a second plot of a corrected cepstrum based on the second cepstrum of FIG. 25A according to some implementations of the present disclosure.

Figure 1:
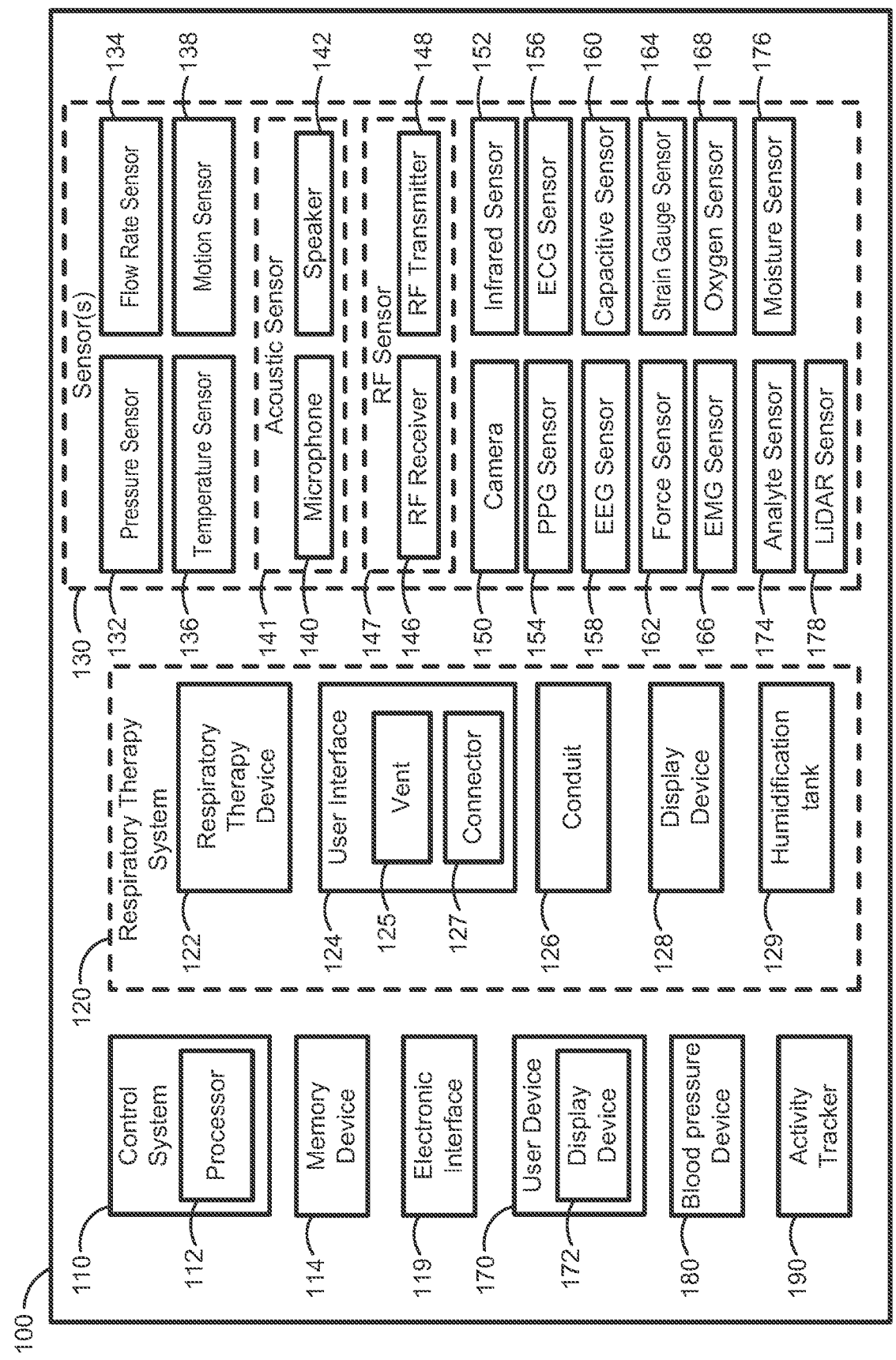
FIG. 1 is a functional block diagram of a system for categorizing and/or characterizing a user interface, according to some implementations of the present disclosure.

While the invention is susceptible to various modifications and alternative forms, specific implementations have been shown by way of example in the drawings and will be described in further detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Various embodiments are described with reference to the attached figures, where like reference numerals are used throughout the figures to designate similar or equivalent elements. The figures are not drawn to scale and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The various embodiments are not limited by the illustrated ordering of acts or events, as some acts may occur in different orders and/or concurrently with other acts or events. Furthermore, not all illustrated acts or events are required to implement a methodology in accordance with the present invention.

Elements and limitations that are disclosed, for example, in the Abstract, Summary, and Detailed Description sections, but not explicitly set forth in the claims, should not be incorporated into the claims, singly, or collectively, by implication, inference, or otherwise. For purposes of the present detailed description, unless specifically disclaimed, the singular includes the plural and vice versa. The word "including" means "including without limitation." Moreover, words of approximation, such as "about," "almost," "substantially," "approximately," "generally," and the like, can be used herein to mean "at," "near," or "nearly at," or "within 3-5% of," or "within acceptable manufacturing tolerances," or any logical combination thereof, for example.

Many individuals suffer from sleep-related and/or respiratory-related disorders such as, for example, Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hyper tension, diabetes, stroke, insomnia, and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall.

Central Sleep Apnea (CSA) is another form of SDB that results when the brain temporarily stops sending signals to the muscles that control breathing. More generally, an apnea generally refers to the cessation of breathing caused by blockage of the air or the stopping of the breathing function.

Typically, the individual will stop breathing for between about 15 seconds and about 30 seconds during an obstructive sleep apnea event. Mixed sleep apnea is another form of SDB that is a combination of OSA and CSA.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for 10 seconds or longer leading to arousal from sleep and which does not fulfill the criteria for an apnea or hypopnea event. In 1999, the AASM Task Force defined RERAs as "a sequence of breaths characterized by increasing respiratory effort leading to an arousal from sleep, but which does not meet criteria for an apnea or hypopnea. These events must fulfil both of the following criteria: 1. pattern of progressively more negative esophageal pressure, terminated by a sudden change in pressure to a less negative level and an arousal; 2. the event lasts 10 seconds or longer. In 2000, the study "Non-Invasive Detection of Respiratory Effort-Related Arousals (RERAs) by a Nasal Cannula/Pressure Transducer System" done at NYU School of Medicine and published in Sleep, vol. 23, No. 6, pp. 763-771, demonstrated that a Nasal Cannula/Pressure Transducer System was adequate and reliable in the detection of RERAs. A RERA detector may be based on a real flow signal derived from a respiratory therapy (e,g, PAP) device. For example, a flow limitation measure may be determined based on a flow signal. A measure of arousal may then be derived as a function of the flow limitation measure and a measure of sudden increase in ventilation. One such method is described in WO 2008/138040, U.S. Pat. Nos. 9,358,353, 10,549,053, and US 2020/0197640, each of which is hereby incorporated by reference herein in its entirety.

Cheyne-Stokes Respiration (CSR) is another form of SDB. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Generally, the present disclosure describes a system and method in which an acoustic reflection is used to analyze a user interface coupled to a respiratory therapy device via a conduit to categorize and/or characterize the user interface. Categorizing the user interface determines the category of the user interface, such as direct or indirect. As described in greater detail below, indirect user interfaces can also be indirect conduit or indirect frame user interfaces. Characterizing the user interface determines the specific type of user interface, including, for example, the manufacturer and specific model of the user interface. In one or more implementations, a user interface can be categorized according to the disclosed methods without also being characterized. Alternatively, in one or more implementations, a user interface can be characterized according to the disclosed methods without also being directly categorized. In which case, the user interface is only indirectly categorized through the characterization, which implicitly identifies the category. Alternatively, in one or more implementations, a user interface can be both categorized (directly) and characterized by the disclosed methods. In one or more implementation, categorizing the user interface can, for example, verify a characterization of the user interface or to create a subset of user interfaces from which to characterize the user interface.

Referring to FIG. 1, a system 100, according to some implementations of the present disclosure, is illustrated. The system 100 can be used to identify a user interface used by a user, among other uses. The system 100 includes a control system 110, a memory device 114, an electronic interface 119, one or more sensors 130, and optionally one or more user devices 170. In some implementation, the system 100 further includes a respiratory therapy system 120 that includes a respiratory therapy device 122. The system 100 can be used to detect and/or identify a user interface 124, as disclosed in further detail herein.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the user device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122 of the respiratory therapy system 120, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family medical history (such as a family history of insomnia or sleep apnea), an employment status of the user, an educational status of the user, a socioeconomic status of the user, or any combination thereof. The medical information can include, for example, information indicative of one or more medical conditions associated with the user, medication usage by the user, or both. The medical information data can further include a fall risk assessment associated with the user (e.g., a fall risk score using the Morse fall scale), a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or acoustic data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120 (also referred to as a respiratory pressure therapy system). The respiratory therapy system 120 can include a respiratory therapy device 122 (also referred to as a respiratory pressure device), a user interface 124 (also referred to as a mask or a patient interface), a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea), other respiratory disorders such as COPD, or other disorders leading to respiratory insufficiency, that may manifest either during sleep or wakefulness.

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about −20 L/min and about 150 L/min, while maintaining a positive pressure (relative to the ambient pressure). In some implementations, the control system 110, the memory device 114, the electronic interface 119, or any combination thereof can be coupled to and/or positioned within a housing of the respiratory therapy device 122.

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm H₂O relative to ambient pressure. For other forms of therapy, such as the delivery of oxygen, the user interface may not include a seal sufficient to facilitate delivery to the airways of a supply of gas at a positive pressure of about 10 cm H₂O.

Figure 2:
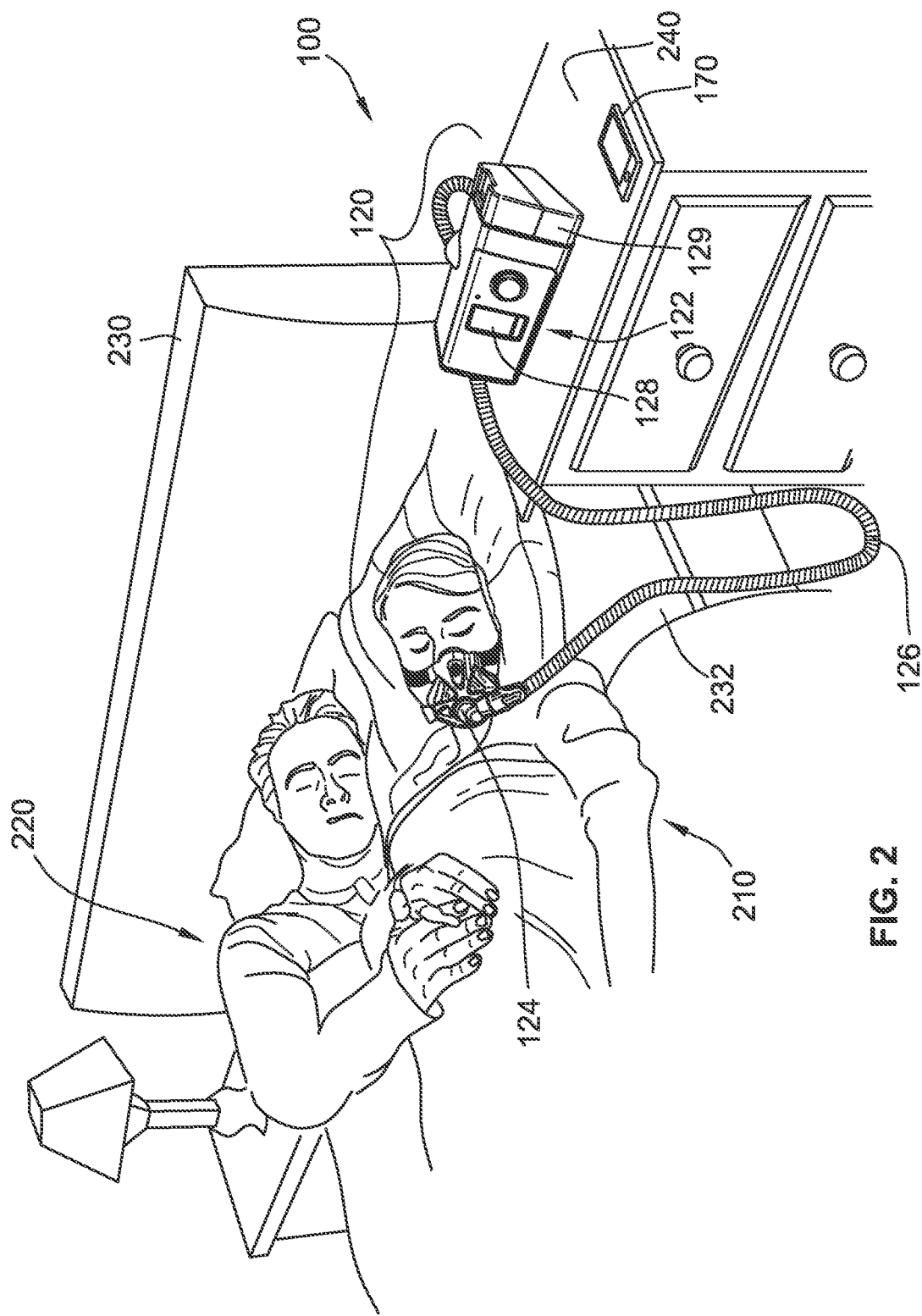
FIG. 2 is a perspective view of at least a portion of the system of FIG. 1, according to some implementations of the present disclosure.

In some implementations, the user interface 124 is or includes a facial mask that covers the nose and mouth of the user (as shown, for example, in FIG. 2). Alternatively, the user interface 124 is or includes a nasal mask that provides air to the nose of the user or a nasal pillow mask that delivers air directly to the nostrils of the user. The user interface 124 can include a strap assembly that has a plurality of straps (e.g., including hook and loop fasteners) for positioning and/or stabilizing the user interface 124 on a portion of the user interface 124 on a desired location of the user (e.g., the face), and a conformal cushion (e.g., silicone, plastic, foam, etc.) that aids in providing an air-tight seal between the user interface 124 and the user. In some implementations, the user interface 124 may include a connector 127 and one or more vents 125. The one or more vents 125 can be used to permit the escape of carbon dioxide and other gases exhaled by the user. In other implementations, the user interface 124 includes a mouthpiece (e.g., a night guard mouthpiece molded to conform to the user's teeth, a mandibular repositioning device, etc.). In some implementations, the connector 127 is distinct from, but couplable to, the user interface 124 (and/or conduit 126). The connector 127 is configured to connect and fluidly couple the user interface 124 to the conduit 126.

The conduit 126 allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation. Generally, the respiratory therapy system 120 forms an air pathway that extends between a motor of the respiratory therapy device 122 and the user and/or the user's airway. Thus, the air pathway generally includes at least a motor of the respiratory therapy device 122, the user interface 124, and the conduit 126.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score or a therapy score (such as a myAir™ score, such as described in WO 2016/061629 and US 2017/0311879, each of which is hereby incorporated by reference herein in its entirety), the current date/time, personal information for the user, a questionnaire for the user, etc.). In some implementations, the display device 128 acts as a human-machine interface (HMI) that includes a graphic user interface (GUI) configured to display the image (s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself. In other implementations, the respiratory therapy device 122 or the conduit 126 can include a waterless humidifier. The waterless humidifier can incorporate sensors that interface with other sensor positioned elsewhere in system 100.

The respiratory therapy system 120 can be used, for example, as a ventilator or a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based at least in part on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can include the display device 128, which can allow the user to interact with the respiratory therapy device 122. The respiratory therapy device 122 can also include the humidification tank 129, which stores the water used to humidify the pressurized air. The respiratory therapy device 122 can be positioned on a nightstand 240 that is directly adjacent to the bed 230 as shown in FIG. 2, or more generally, on any surface or structure that is generally adjacent to the bed 230 and/or the user 210. The user can also wear the blood pressure device 180 and the activity tracker 190 while lying on the mattress 232 in the bed 230.

Referring back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, an RF transmitter 148, a camera 150, an infrared (IR) sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or sensors 130 are configured to output sensor data that is received and stored in the memory device 114 or one or more other memory devices. The sensors 130 can also include, an electrooculography (EOG) sensor, a peripheral oxygen saturation ($SpO_2$) sensor, a galvanic skin response (GSR) sensor, a carbon dioxide ($CO_2$) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the IR sensor 152, the PPG sensor 154, the ECG sensor 156, the EEG sensor 158, the capacitive sensor 160, the force sensor 162, the strain gauge sensor 164, the EMG sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example physiological data, acoustic data, or both, that is associated with a user of the respiratory therapy system 120 (such as the user 210 of FIG. 2), the respiratory therapy system 120, both the user and the respiratory therapy system 120, or other entities, objects, activities, etc. Physiological data generated by one or more of the sensors 130 can be used by the control system 110 to determine a sleep-wake signal associated with the user during the sleep session and one or more sleep-related parameters. The sleep-wake signal can be indicative of one or more sleep stages (sometimes referred to as sleep states), including sleep, wakefulness, relaxed wakefulness, micro-awakenings, or distinct sleep stages such as a rapid eye movement (REM) stage (which can include both a typical REM stage and an atypical REM stage), a first non-REM stage (often referred to as "N1"), a second non-REM stage (often referred to as "N2"), a third non-REM stage (often referred to as "N3"), or any combination thereof. Methods for determining sleep stages from physiological data generated by one or more of the sensors, such as sensors 130, are described in, for example, WO 2014/047310, U.S. Pat. Nos. 10,492,720, 10,660,563, US 2020/0337634, WO 2017/132726, WO 2019/122413, US 2021/0150873, WO 2019/122414, US 2020/0383580, each of which is hereby incorporated by reference herein in its entirety.

The sleep-wake signal can also be timestamped to indicate a time that the user enters the bed, a time that the user exits the bed, a time that the user attempts to fall asleep, etc. The sleep-wake signal can be measured one or more of the sensors 130 during the sleep session at a predetermined sampling rate, such as, for example, one sample per second, one sample per 30 seconds, one sample per minute, etc. Examples of the one or more sleep-related parameters that can be determined for the user during the sleep session based at least in part on the sleep-wake signal include a total time in bed, a total sleep time, a total wake time, a sleep onset latency, a wake-after-sleep-onset parameter, a sleep efficiency, a fragmentation index, an amount of time to fall asleep, a consistency of breathing rate, a fall asleep time, a wake time, a rate of sleep disturbances, a number of movements, or any combination thereof.

Physiological data and/or acoustic data generated by the one or more sensors 130 can also be used to determine a respiration signal associated with the user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration amplitude ratio, an inspiration-expiration duration ratio, a number of events per hour, a pattern of events, pressure settings of the respiratory therapy device 122, or any combination thereof. The event(s) can include snoring, apneas, central apneas, obstructive apneas, mixed apneas, hypopneas, RERAs, a flow limitation (e.g., an event that results in the absence of the increase in flow despite an elevation in negative intrathoracic pressure indicating increased effort), a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, an elevated stress level, etc. Events can be detected by any means known in the art such as described in, for example, U.S. Pat. Nos. 5,245,995, 6,502,572, WO 2018/050913, WO 2020/104465, each of which is incorporated by reference herein in its entirety.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user, a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user and proximal to the user interface 124, and configured to detect features of the pulse shape, speed, amplitude, or volume. In some implementations, the motion sensor 138 alternatively or additionally generates one or more signals representing bodily movement of the user, from which may be obtained a signal representing a sleep state of the user; for example, via a respiratory movement of the user.

The microphone 140 outputs acoustic data that can be stored in the memory device 114 and/or analyzed by the processor 112 of the control system 110. The acoustic data generated by the microphone 140 is reproducible as one or more sound(s) during a sleep session (e.g., sounds from the user) to determine (e.g., using the control system 110) one or more sleep-related parameters, as described in further detail herein. The acoustic data from the microphone 140 can also be used to identify (e.g., using the control system 110) an event experienced by the user during the sleep session, as described in further detail herein. In other implementations, the acoustic data from the microphone 140 is representative of noise associated with the respiratory therapy system 120. In some implementations, the system 100 includes a plurality of microphones (e.g., two or more microphones and/or an array of microphones with beam-forming) such that sound data generated by each of the plurality of microphones can be used to discriminate the sound data generated by another of the plurality of microphones. The microphone 140 can be coupled to or integrated in the respiratory therapy system 120 (or the system 100) generally in any configuration. For example, the microphone 140 can be disposed inside the respiratory therapy device 122, the user interface 124, the conduit 126, or other components. The microphone 140 can also be positioned adjacent to or coupled to the outside of the respiratory therapy device 122, the outside of the user interface 124, the outside of the conduit 126, or outside of any other components. The microphone 140 could also be a component of the user device 170 (e.g., the microphone 140 is a microphone of a smart phone). The microphone 140 can be integrated into the user interface 124, the conduit 126, the respiratory therapy device 122, or any combination thereof. In general, the microphone 140 can be located at any point within or adjacent to the air pathway of the respiratory therapy system 120, which includes at least the motor of the respiratory therapy device 122, the user interface 124, and the conduit 126. Thus, the air pathway can also be referred to as the acoustic pathway.

The speaker 142 outputs sound waves that are audible to the user. In one or more implementations, the sound waves can be audible to a user of the system 100 or inaudible to the user of the system (e.g., ultrasonic sound waves). The speaker 142 can be used, for example, as an alarm clock or to play an alert or message to the user (e.g., in response to an event). In some implementations, the speaker 142 can be used to communicate the acoustic data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and/or frequency, and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user or a bed partner of the user (such as bed partner 220 in FIG. 2). Based at least in part on the data from the microphone 140 and/or the speaker 142, the control system 110 can determine a location of the user and/or one or more of the sleep-related parameters described in herein, such as, for example, a respiration signal, a respiration rate, an inspiration amplitude, an expiration amplitude, an inspiration-expiration ratio, a number of events per hour, a pattern of events, a sleep stage, pressure settings of the respiratory therapy device 122, a mouth leak status, or any combination thereof. In this context, a SONAR sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above. In some implementations, the speaker 142 is a bone conduction speaker. In some implementations, the one or more sensors 130 include (i) a first microphone that is the same or similar to the microphone 140, and is integrated into the acoustic sensor 141 and (ii) a second microphone that is the same as or similar to the microphone 140, but is separate and distinct from the first microphone that is integrated into the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a RADAR sensor). In some such implementations, the RF sensor 147 includes a control circuit. The specific format of the RF communication could be WiFi, Bluetooth, etc.

In some implementations, the RF sensor 147 is a part of a mesh system. One example of a mesh system is a WiFi mesh system, which can include mesh nodes, mesh router (s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based at least in part on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user enters the user's bed (such as bed 230 in FIG. 2), and to determine a time when the user exits the bed 230. The camera 150 can also be used to track eye movements, pupil dilation (if one or both of the user's eyes are open), blink rate, or any changes during REM sleep. The camera 150 can also be used to track the position of the user, which can impact the duration and/or severity of apneic episodes in users with positional obstructive sleep apnea.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user, embedded in clothing and/or fabric that is worn by the user, embedded in and/or coupled to the user interface 124 and/or its associated headgear (e.g., straps, etc.), etc.

The ECG sensor 156 outputs physiological data associated with electrical activity of the heart of the user. In some implementations, the ECG sensor 156 includes one or more electrodes that are positioned on or around a portion of the user during the sleep session. The physiological data from the ECG sensor 156 can be used, for example, to determine one or more of the sleep-related parameters described herein.

The EEG sensor 158 outputs physiological data associated with electrical activity of the brain of the user. In some implementations, the EEG sensor 158 includes one or more electrodes that are positioned on or around the scalp of the user during the sleep session. The physiological data from the EEG sensor 158 can be used, for example, to determine a sleep stage of the user at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user. The data output by the analyte sensor 174 can be stored in the memory device 114 and used by the control system 110 to determine the identity and concentration of any analytes in the user's breath. In some implementations, the analyte sensor 174 is positioned near a mouth of the user to detect analytes in breath exhaled from the user's mouth. For example, when the user interface 124 is a facial mask that covers the nose and mouth of the user, the analyte sensor 174 can be positioned within the facial mask to monitor the user mouth breathing. In other implementations, such as when the user interface 124 is a nasal mask or a nasal pillow mask, the analyte sensor 174 can be positioned near the nose of the user to detect analytes in breath exhaled through the user's nose. In still other implementations, the analyte sensor 174 can be positioned near the user's mouth when the user interface 124 is a nasal mask or a nasal pillow mask. In this implementation, the analyte sensor 174 can be used to detect whether any air is inadvertently leaking from the user's mouth. In some implementations, the analyte sensor 174 is a volatile organic compound (VOC) sensor that can be used to detect carbon-based chemicals or compounds, such as carbon dioxide. In some implementations, the analyte sensor 174 can also be used to detect whether the user is breathing through their nose or mouth. For example, if the data output by an analyte sensor 174 positioned near the mouth of the user or within the facial mask (in implementations where the user interface 124 is a facial mask) detects the presence of an analyte, the control system 110 can use this data as an indication that the user is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user's face, near the connection between the conduit 126 and the user interface 124, near the connection between the conduit 126 and the respiratory therapy device 122, etc.). Thus, in some implementations, the moisture sensor 176 can be coupled to or integrated into the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user, for example the air inside the user's bedroom. The moisture sensor 176 can also be used to track the user's biometric response to environmental changes.

One or more LiDAR sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, or any combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, the pressure sensor 132 and/or the flow rate sensor 134 are integrated into and/or coupled to the respiratory therapy device 122. In some implementations, at least one of the one or more sensors 130 is not coupled to the respiratory therapy device 122, the control system 110, or the user device 170, and is positioned generally adjacent to the user during the sleep session (e.g., positioned on or in contact with a portion of the user, worn by the user, coupled to or positioned on the nightstand, coupled to the mattress, coupled to the ceiling, etc.). More generally, the one or more sensors 130 can be positioned at any suitable location relative to the user such that the one or more sensors 130 can generate physiological data associated with the user and/or the bed partner 220 during one or more sleep session.

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, an average duration of events, a range of event durations, a ratio between the number of different events, a sleep stage, an apnea-hypopnea index (AHI), or any combination thereof. The one or more events can include snoring, apneas, central apneas, obstructive apneas, mixed apneas, hypopneas, an intentional user interface leak, an unintentional user interface leak, a mouth leak, a cough, a restless leg, a sleeping disorder, choking, an increased heart rate, labored breathing, an asthma attack, an epileptic episode, a seizure, increased blood pressure, hyperventilation, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 includes a display device 172. The user device 170 can be, for example, a mobile device such as a smart phone, a tablet, a laptop, a gaming console, a smart watch, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device 170 is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices 170 can be used by and/or included in the system 100.

The blood pressure device 180 is generally used to aid in generating physiological data for determining one or more blood pressure measurements associated with a user. The blood pressure device 180 can include at least one of the one or more sensors 130 to measure, for example, a systolic blood pressure component and/or a diastolic blood pressure component.

In some implementations, the blood pressure device 180 is a sphygmomanometer including an inflatable cuff that can be worn by a user and a pressure sensor (e.g., the pressure sensor 132 described herein). For example, as shown in the example of FIG. 2, the blood pressure device 180 can be worn on an upper arm of the user. In such implementations where the blood pressure device 180 is a sphygmomanometer, the blood pressure device 180 also includes a pump (e.g., a manually operated bulb) for inflating the cuff. In some implementations, the blood pressure device 180 is coupled to the respiratory therapy device 122 of the respiratory therapy system 120, which in turn delivers pressurized air to inflate the cuff. More generally, the blood pressure device 180 can be communicatively coupled with, and/or physically integrated in (e.g., within a housing), the control system 110, the memory device 114, the respiratory therapy system 120, the user device 170, and/or the activity tracker 190.

The activity tracker 190 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. The activity tracker 190 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 190 is a wearable device that can be worn by the user, such as a smartwatch, a wristband, a ring, or a patch. For example, referring to FIG. 2, the activity tracker 190 is worn on a wrist of the user. The activity tracker 190 can also be coupled to or integrated a garment or clothing that is worn by the user. Alternatively, still, the activity tracker 190 can also be coupled to or integrated in (e.g., within the same housing) the user device 170. More generally, the activity tracker 190 can be communicatively coupled with, or physically integrated in (e.g., within a housing), the control system 110, the memory device 114, the respiratory therapy system 120, the user device 170, and/or the blood pressure device 180.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for identifying a user interface used by a user, according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. As a further example, a fourth alternative system includes the control system 110, the memory device 114, the respiratory therapy system 120, at least one of the one or more sensors 130, the user device 170, and the blood pressure device 180 and/or activity tracker 190. Thus, various systems for modifying pressure settings can be formed using any portion or portions of the components shown and described herein and/or in combination with one or more other components.

Referring again to FIG. 2, in some implementations, the control system 110, the memory device 114, any of the one or more sensors 130, or a combination thereof can be located on and/or in any surface and/or structure that is generally adjacent to the bed 230 and/or the user 210. For example, in some implementations, at least one of the one or more sensors 130 can be located at a first position on and/or in one or more components of the respiratory therapy system 120 adjacent to the bed 230 and/or the user 210. The one or more sensors 130 can be coupled to the respiratory therapy system 120, the user interface 124, the conduit 126, the display device 128, the humidification tank 129, or a combination thereof.

Alternatively, or additionally, at least one of the one or more sensors 130 can be located at a second position on and/or in the bed 230 (e.g., the one or more sensors 130 are coupled to and/or integrated in the bed 230). Further, alternatively or additionally, at least one of the one or more sensors 130 can be located at a third position on and/or in the mattress 232 that is adjacent to the bed 230 and/or the user 210 (e.g., the one or more sensors 130 are coupled to and/or integrated in the mattress 232). Alternatively, or additionally, at least one of the one or more sensors 130 can be located at a fourth position on and/or in a pillow that is generally adjacent to the bed 230 and/or the user 210.

Alternatively, or additionally, at least one of the one or more sensors 130 can be located at a fifth position on and/or in the nightstand 240 that is generally adjacent to the bed 230 and/or the user 210. Alternatively, or additionally, at least one of the one or more sensors 130 can be located at a sixth position such that the at least one of the one or more sensors 130 are coupled to and/or positioned on the user 210 (e.g., the one or more sensors 130 are embedded in or coupled to fabric, clothing, and/or a smart device worn by the user 210). More generally, at least one of the one or more sensors 130 can be positioned at any suitable location relative to the user 210 such that the one or more sensors 130 can generate sensor data associated with the user 210.

In some implementations, a primary sensor, such as the microphone 140, is configured to generate acoustic data associated with the user 210 during a sleep session. For example, one or more microphones (the same as, or similar to, the microphone 140 of FIG. 1) can be integrated in and/or coupled to (i) a circuit board of the respiratory therapy device 122, (ii) the conduit 126, (iii) a connector between components of the respiratory therapy system 120, (iv) the user interface 124, (v) a headgear (e.g., straps) associated with the user interface, or (vi) a combination thereof.

In some implementations, one or more secondary sensors may be used in addition to the primary sensor to generate additional data. In some such implementations, the one or more secondary sensors include: a microphone (e.g., the microphone 140 of the system 100), a flow rate sensor (e.g., the flow rate sensor 134 of the system 100), a pressure sensor (e.g., the pressure sensor 132 of the system 100), a temperature sensor (e.g., the temperature sensor 136 of the system 100), a camera (e.g., the camera 150 of the system 100), a vane sensor (VAF), a hot wire sensor (MAF), a cold wire sensor, a laminar flow sensor, an ultrasonic sensor, an inertial sensor, or a combination thereof.

Additionally, or alternatively, one or more microphones (the same as, or similar to, the microphone 140 of FIG. 1) can be integrated in and/or coupled to a co-located smart device, such as the user device 170, a TV, a watch (e.g., a mechanical watch or another smart device worn by the user), a pendant, the mattress 232, the bed 230, beddings positioned on the bed 230, the pillow, a speaker (e.g., the speaker 142 of FIG. 1), a radio, a tablet device, a waterless humidifier, or a combination thereof. A co-located smart device can be any smart device that is within range for detecting sounds emitted by the user, the respiratory therapy system 120, and/or any portion of the system 100. In some implementations, the co-located smart device is a smart device that is in the same room as the user during the sleep session.

Additionally, or alternatively, in some implementations, one or more microphones (the same as, or similar to, the microphone 140 of FIG. 1) can be remote from the system 100 (FIG. 1) and/or the user 210 (FIG. 2), so long as there is an air passage allowing acoustic signals to travel to the one or more microphones. For example, the one or more microphones can be in a different room from the room containing the system 100. In some implementations, based at least in part on an analysis of the acoustic data, a physical obstruction in the airway of a user can be characterize and/or determined.

As used herein, a sleep session can be defined in a number of ways based at least in part on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Figure 3:
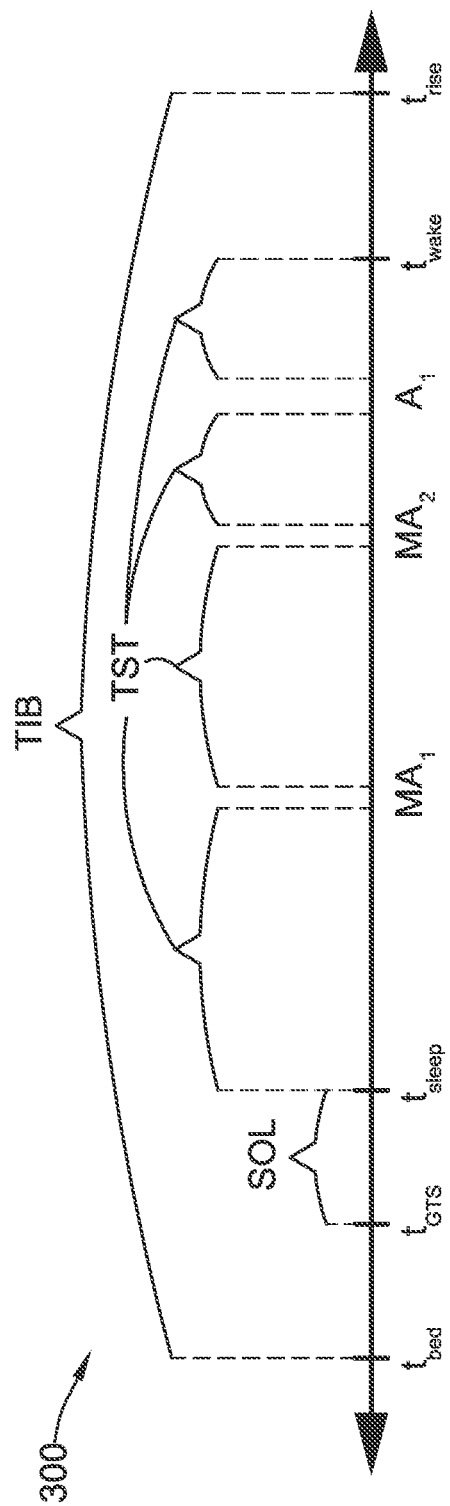
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based at least in part on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based at least in part on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based at least in part on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based at least in part on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based at least in part on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based at least in part on the system monitoring the user's sleep behavior.

The total time in bed (TIB) is the duration of time between the time enter bed time teed and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
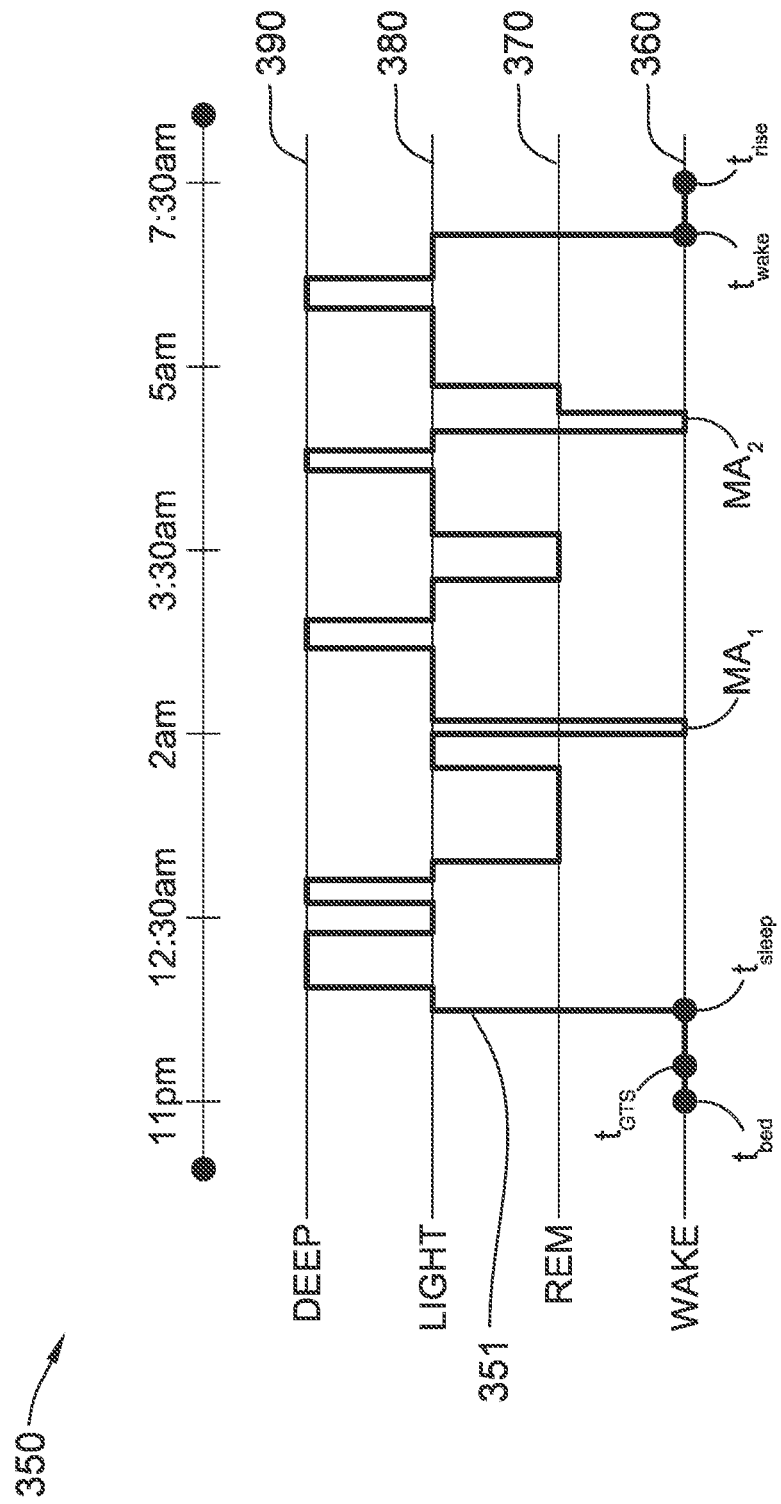
FIG. 4 illustrates an exemplary hypnogram associated with the sleep session of FIG. 3, according to some implementations of the present disclosure.

Referring to FIG. 4, an exemplary hypnogram 350 corresponding to the timeline 300 (FIG. 3), according to some implementations, is illustrated. As shown, the hypnogram 350 includes a sleep-wake signal 351, a wakefulness stage axis 360, a REM stage axis 370, a light sleep stage axis 380, and a deep sleep stage axis 390. The intersection between the sleep-wake signal 351 and one of the axes 360-390 is indicative of the sleep stage at any given time during the sleep session.

The sleep-wake signal 351 can be generated based at least in part on physiological data associated with the user (e.g., generated by one or more of the sensors 130 described herein). The sleep-wake signal can be indicative of one or more sleep stages, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 350 is shown in FIG. 4 as including the light sleep stage axis 380 and the deep sleep stage axis 390, in some implementations, the hypnogram 350 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration amplitude ratio, an inspiration-expiration duration ratio, a number of events per hour, a pattern of events, or any combination thereof. Information describing the sleep-wake signal can be stored in the memory device 114.

The hypnogram 350 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based at least in part on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based at least in part on, for example, data generated by the motion sensor 138, the microphone 140, the camera 150, or any combination thereof. The go-to-sleep time can be determined based at least in part on, for example, data from the motion sensor 138 (e.g., data indicative of no movement by the user), data from the camera 150 (e.g., data indicative of no movement by the user and/or that the user has turned off the lights), data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory therapy device 122, data indicative of the user donning the user interface 124, etc.), or any combination thereof.

FIG. 5 illustrates the generation of acoustic data in response to an acoustic reflection indicative of one or more features of a user interface, according to aspects of the present disclosure. The generation of the acoustic data includes the acoustic sensor 141, which includes the microphone 140 (or any type of audio transducer) and a speaker 142. However, as discussed above, the speaker 142 can instead be replaced by another device that can generate an acoustic signal, such as the motor of the respiratory therapy device 122. The microphone 140 and speaker 142 are shown in specific locations relative to the conduit 126, which is connected to the respiratory therapy device 122 (not shown). However, the locations of the microphone 140 and the speaker 142 can vary from what is shown, as discussed above.

The speaker 142 emits an acoustic signal 302 within the conduit 126. The acoustic signal 302 is in the form of a sound. The sound can be one or more of a standard sound (e.g., an original, unmodified sound from an off-the-shelf sound application), a custom sound, an inaudible frequency, a white noise sound, a broad band impulse, a continuous sinusoidal waveform, a square waveform, a sawtooth waveform, and a frequency modulated sinusoid (e.g., chirp). According to some other implementations, the acoustic signal 302 can be in the form of one or more of an audible sound or an ultrasonic sound. According to some other implementations, the acoustic signal 302 is in the form of an inaudible sound, where the sound is inaudible based on one or both of the frequency of the sound (e.g., the frequency being outside of the frequency range for human hearing) or the amplitude of the sound (e.g., the amplitude being low enough that the sound is not loud enough for human perception).

In one or more implementations, the acoustic signal 302 is emitted at specific times, such as when the user first puts on the user interface, after the user takes off the user interface, after detecting that an apnea event or a hypopnea event is occurring (e.g., after detecting using a respiratory therapy device that an apnea event or a hypopnea event is occurring). For example, the specific monitoring times are selected to be at intervals of 0.1 seconds for a duration of at least 4 seconds.

The acoustic signal 302 travels down the length L of the conduit 126 until the acoustic signal 302 contacts a feature 304 of the user interface 124, such as at or near a connection 306 of the user interface 124 with the conduit 126. The feature 304 can include a widening (or a narrowing) of the pathway 308 formed through the conduit 126 and the user interface 124. The widening at the feature 304 causes a change in the acoustic impedance of the acoustic signal 302 and an acoustic reflection 310. The acoustic reflection 310 travels back down the length L of the conduit 126 until it reaches the microphone 140. The microphone 140 detects the acoustic reflection 310 and generates acoustic data in response to the acoustic reflection 310. The generated acoustic data is subsequently analyzed for categorizing and/or characterizing the user interface, as further discussed below with respect to FIGS. 6 and 14A.

The acoustic signal 302 can continue beyond the feature 304 and into the user interface 124. Although not illustrated, the user interface 124 can include one or more additional features that change the acoustic impedance of the acoustic signal 302, which further generates the acoustic reflection 310. Thus, although only the feature 304 is illustrated and described as causing the acoustic reflection 310, there can be multiple features of the user interface 124 that can all contribute to the acoustic reflection 310.

FIG. 6 is a flow diagram of a method 400 for characterizing a user interface, according to aspects of the present disclosure. For purposes of convenience, the following description will be in reference to the method 400 being performed by a respiratory therapy system, such as the respiratory therapy system 120. However, one or more other devices can perform the method 400, such as one or more user devices 170. For example, such user devices 170 can communicate with the respiratory therapy system 120 for analyzing and characterizing the data further discussed below.

At step 402, the respiratory therapy system 120 generates acoustic data associated with an acoustic reflection of an acoustic signal. The acoustic data can be generated based on an acoustic transducer detecting the acoustic reflection. For example, the acoustic transducer can be a microphone that converts the pressure waves of the acoustic reflection into electrical signals representing the data.

The acoustic reflection is indicative of, at least in part, one or more features of a user interface coupled to a respiratory therapy device via a conduit. As the acoustic signal travels down the conduit, the acoustic signal interacts with one or more features of the conduit, one or more features of the connection between the conduit and the user interface, one or more features of the user interface, etc. The interactions can cause the acoustic signal to reflect, thereby generating the acoustic reflection. As will be discussed in greater detail below, with respect to FIGS. 15 to 20, because the acoustic reflection is caused, at least in part, by the one or more features of the user interface, the acoustic reflection is indicative of the one or more features of the user interface.

In one or more implementations, the acoustic signal can be emitted into the conduit connected to the user interface via an audio transducer, such as a speaker. Alternatively, or in addition, the acoustic signal can be emitted into the conduit via a motor of the respiratory therapy device connected to the conduit. For example, the motor of the respiratory therapy device can emit sound as it forces air through the conduit. The emitted sound can be the acoustic signal, or at least part of the acoustic signal.

In one or more implementations, the acoustic signal can be a sound audible to a human (e.g., an average human with average human hearing). A sound is audible to a human when the sound has an amplitude that is loud enough for detection by the human and when it has a frequency within the frequency range of human hearing, which is generally about 20 Hz to about 20,000 Hz.

In one or more implementations, the acoustic signal can be a sound that is inaudible to a human (e.g., an average human with average human hearing). A sound is inaudible when the sound has an amplitude that is less than the lowest perceptible amplitude of a human. Alternatively, or in addition, a sound is inaudible to a human when the sound has a frequency that is outside of the frequency range of human hearing, which, as stated above, is about 20 Hz to about 20,000 Hz. For example, in one or more implementations, the acoustic signal can be an ultrasonic sound that has a frequency that is higher than the highest perceptible frequency for human hearing.

In one or more implementations, the method 400 can be performed when the user interface is connected to a user (e.g., worn by the user or otherwise engaged with the face of the user). In other words, the acoustic signal can be emitted, and the acoustic data can be generated based on the acoustic reflection with the user interface connected or coupled to the user. Further, the user interface can be connected or coupled to the user while the respiratory therapy system is providing therapy to the user, before providing therapy to the user, or after providing therapy to the user. For example, the flow of pressurized air can be provided through the conduit and into the user interface during the generating of the acoustic data. The providing of therapy may generate the acoustic signal, such as by the motor of the respiratory therapy device emitting the acoustic signal. Alternatively, the acoustic signal can be emitted in the conduit during an absence of a flow of pressurized air through the conduit and into the user interface.

Alternatively, the method can be performed when the user interface is not connected or coupled to a user. Specifically, the acoustic reflection that is indicative of one or more features of the user interface does not require the presence of the user. Accordingly, the method 400 can be performed prior to the user wearing the user interface, or after the user removes the user interface.

Although step 402 is described as being based on an acoustic signal and an acoustic reflection, in one or more implementations, the generated acoustic data can be generated from a plurality of acoustic reflections from a plurality of acoustic signals. The acoustic signals can be the same acoustic signal that is repeatedly emitted, or can be different acoustic signals that are emitted together, forming a single acoustic signal, or can be emitted separately. When there are multiple acoustic signals for multiple acoustic reflections, the generated acoustic data can be an average of the plurality of acoustic reflections from the plurality of the acoustic signals.

At step 404, the respiratory therapy system 120 analyzes the generated acoustic data. The analyzing includes windowing the generated acoustic data based, at least in part, on at least one feature of the respiratory therapy system, such as at least one feature of the user interface, at least one feature of the conduit, etc. The at least one feature of the user interface can be, for example, the expansion from the connection of the conduit to the chamber formed by the cushion of a full-face mask against a user's face. The at least one feature of the conduit can be, for example, the length of the conduit. More specifically, the length can be the distance from the acoustic sensor to where the conduit connects to the user interface. In one or more implementations, the windowing can be based, at least in part, on at least one feature of the one or more features of the user interface. The windowing is a selection of a portion of the generated acoustic data that is used for additional analysis and/or for characterizing the user interface, as discussed below. The windowing focuses in on the generated acoustic data that can differentiate and distinguish between the various user interfaces that exist for respiratory therapy systems. Accordingly, the windowing can focus in on the generated acoustic data that is indicative of the user interface. The windowing can beneficially allow regions of the signal that may otherwise confound the estimation of the user interface, such as varying conduit lengths, differences in respiratory therapy systems, such as different respiratory therapy devices, etc. to be ignored. Thus, windowing the generated acoustic data selects only the region of the acoustic signal, and the corresponding data, that is associated with the user interface. As a result, the windowing allows for ignoring regions of the acoustic signal, and the corresponding data, that may otherwise confound the estimation of the user interface, such as the factors discussed above.

The at least one feature has a corresponding point in the generated acoustic data that acts as fiducial point. The fiducial point provides a basis for analyzing the generated acoustic data for different types of user interfaces, conduits, respiratory therapy devices, etc. Thus, the fiducial point acts as a reference for further analysis of the generated acoustic data, and provides for consistency between different acoustic data generated under different circumstances.

In one or more implementations, the fiducial point can correspond to a location of the one or more features along a pathway formed, at least in part, by the conduit and the user interface. For example, the fiducial point can correspond to a feature of the conduit or a feature of the connection between the conduit and the user interface. In one or more implementations, the fiducial point can correspond to a feature of the user interface itself. In one or more implementations, the fiducial point is the same for a given user interface. In one or more implementations, the fiducial point is the same for all of the different possible user interfaces. The feature can be generic to different types of user interfaces so that the feature, or at least a variation of the feature, is present in all respiratory therapy systems that include a user interface connected to a conduit. For example, the feature can be the expansion of the acoustic pathway that occurs at the connection between a conduit and a user interface. Although such an expansion may not be identical for every combination of the conduit and different user interface, every combination of the conduit with a user interface can include such an expansion. Accordingly, the expansion at the connection between the conduit and the user interface can be the feature that corresponds to the fiducial point user in widowing of the generated acoustic data.

Broadly, the fiducial point can be any feature that causes a change in acoustic impedance and, therefore, is present in the generated acoustic data from the acoustic reflection. In one or more implementations, the change in the acoustic impedance can be based, at least in part, on a narrowing of the pathway formed by the conduit and the user interface and at (i) the user interface, (ii) a connection of the conduit and the user interface, or (iii) a combination thereof. Alternatively, the change in the acoustic impedance can be based, at least in part, on a widening of the pathway at (i) the user interface, (ii) a connection of the conduit and the user interface, or (iii) a combination thereof.

In one or more implementations further discussed below, the analysis of the generated acoustic data can include performing a deconvolution on the generated acoustic data, such as calculating the cepstrum of the generated acoustic data. In which case, the fiducial point can be a minimum point within a predetermined section of the deconvolution of the generated acoustic data. Alternatively, the fiducial point can be a maximum point within a predetermined section of the deconvolution of the generated acoustic data. As discussed above, the fiducial point can be based on the connection between the user interface and the conduit, and the predetermined section can be based on the length of the conduit. More specifically, the predetermined section can be based on the distance between the acoustic sensor and the connection between the conduit and the user interface.

Figure 7:
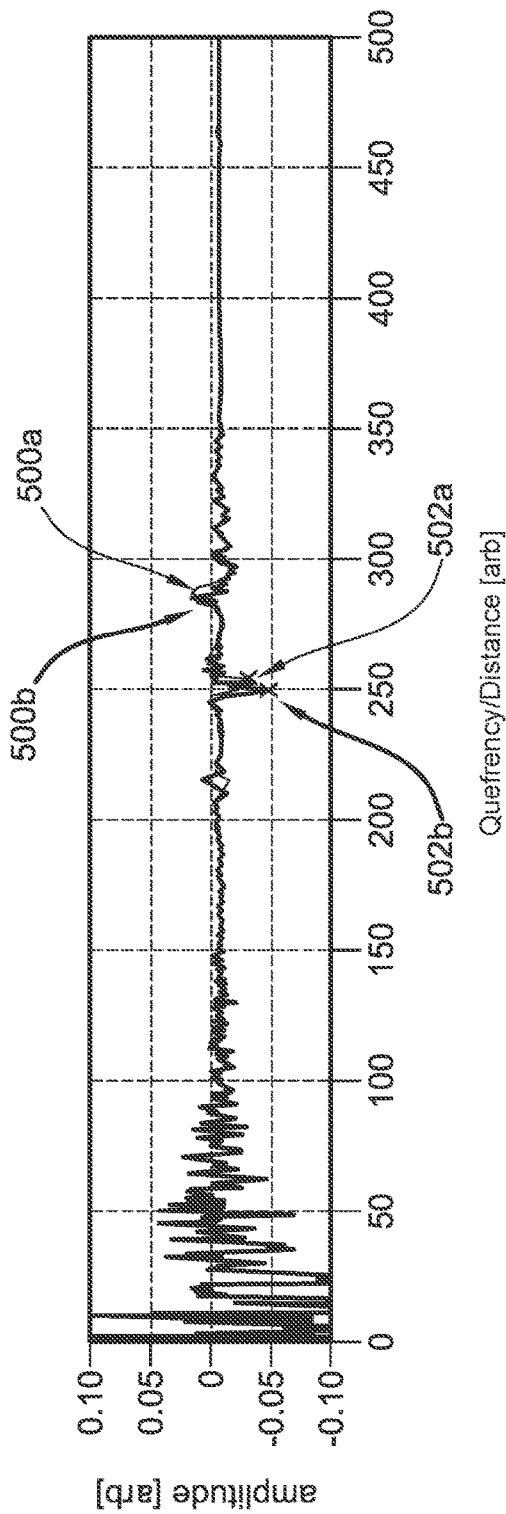
FIG. 7 is a plot of calculated cepstrums of generated acoustic data, according to some implementations of the present disclosure.

Referring to FIG. 7, illustrated are the calculated cepstrums 500*a* and 500*b* resulting from generated acoustic data for two different acoustic reflections. The two cepstrums 500*a* and 500*b* are shown merely for descriptive convenience and are not meant to be limiting. For example, a single cepstrum can be calculated for generated acoustic data for characterizing a user interface. The two cepstrums 500*a* and 500*b* are two cepstrums calculated from different generated acoustic data for the same user interface.

The plots are shown with quefrency in the X-axis and amplitude in the Y-axis. The quefrency is similar to time or distance, but the units of the X-axis are simply samples or sample numbers of the acoustic reflection. The units of the Y-axis can be any unit that measures the amplitude. Around the 250 value in the X-axis are large minima 502*a* and 502*b*, which can be used as fiducial points for analyzing the generated acoustic data. These correspond to a widening of the pathway in the conduit, such as the connection point between the conduit and the user interface.

Referring back to step 404 of FIG. 6, in one or more implementations, the windowing can include a first windowing of the generated acoustic data and a second windowing of the generated acoustic data. In one or more implementations, the first windowing can identify or locate a feature of the user interface corresponding to the fiducial point. Subsequently, the second windowing can identify or locate further features of the user interface. The first windowing of the generated acoustic data can vary from the second windowing of the generated acoustic data by an amount of the generated acoustic data that is selected before the fiducial point in the generated acoustic data, after the fiducial point in the generated acoustic data, or a combination thereof. In relation to a length of the pathway resulting from the conduit and the user interface, the first windowing can capture only about 10 cm before and after the fiducial point, e.g., about 10 cm before and after connection point between the conduit and the user interface. In contrast, the second windowing can capture about 35 cm before the fiducial point and about 50 cm after the fiducial point.

The amount of data captured by the windowing can vary based on the amount of the generated acoustic data that is required for a specific analysis related to the windowing. For example, the first windowing may be merely to identify the fiducial point. As a result, the size of the resulting window of the windowing can be smaller because it is focused purely on determining the fiducial point. Once the fiducial point is determined, the second windowing can occur, which can result in a larger second window. The larger second window can capture the generated acoustic data that is sent to the characterizing step discussed below. The characterizing step may benefit from additional data, which is why the second window generated from the second windowing can be larger than the first window generated from the first windowing, with the larger window capturing more features for characterizing the user interface compared to the first window. Alternatively, the size of the windows generated during the first and second windowing can be reversed, with the first window being large than the second window. The first window being large may assist in determining the correct fiducial point for the analysis.

Figure 8:
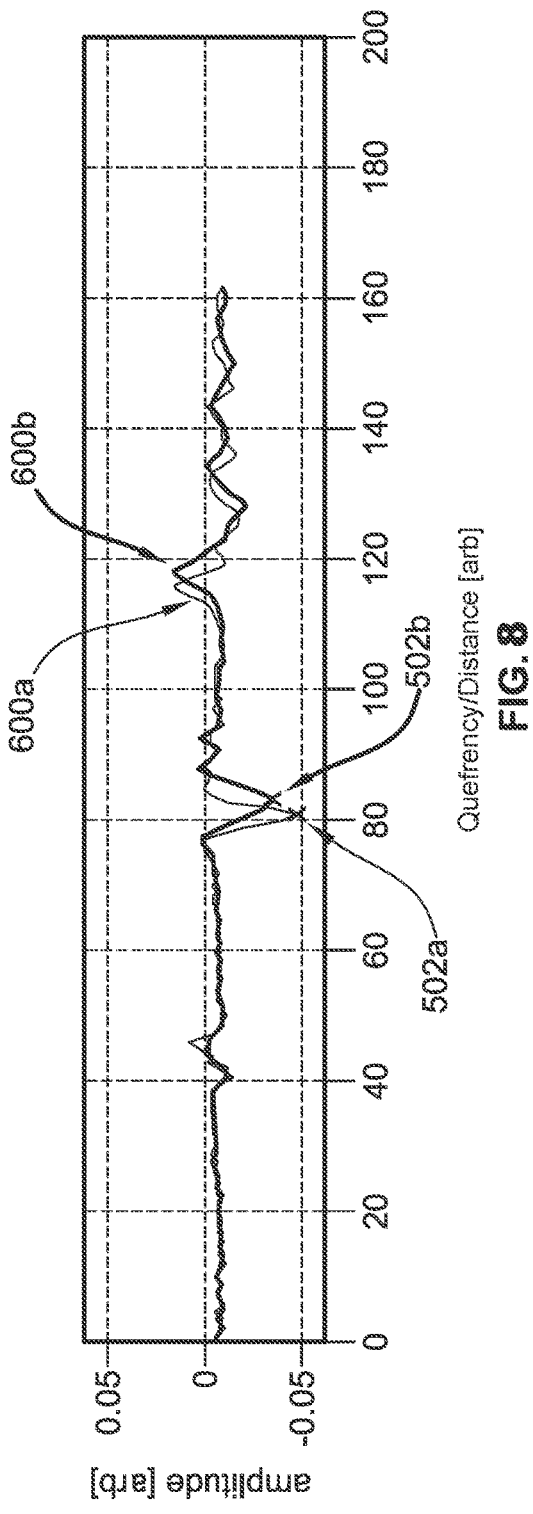
FIG. 8 is a plot of windowed cepstrums of generated acoustic data, according to some implementations of the present disclosure.

Referring to FIG. 8, the windowed cepstrums 600*a* and 600*b*, corresponding to cepstrums 500*a* and 500*b*, respectively, are shown after the windowing is performed as described above. The windowing removed the generated acoustic data after about the 350 value in the X-axis in FIG. 7, and removed the generated acoustic data before about the 200 value in the X-axis in FIG. 7. The windowing is performed to eliminate the generated acoustic data that is not used for characterizing the user interface, and that could potentially disrupt the additional analysis and characterization of the acoustic data for determining the user interface. The generated acoustic data that remains is about 80 on either side of the fiducial points 502a and 502b.

Figure 9:
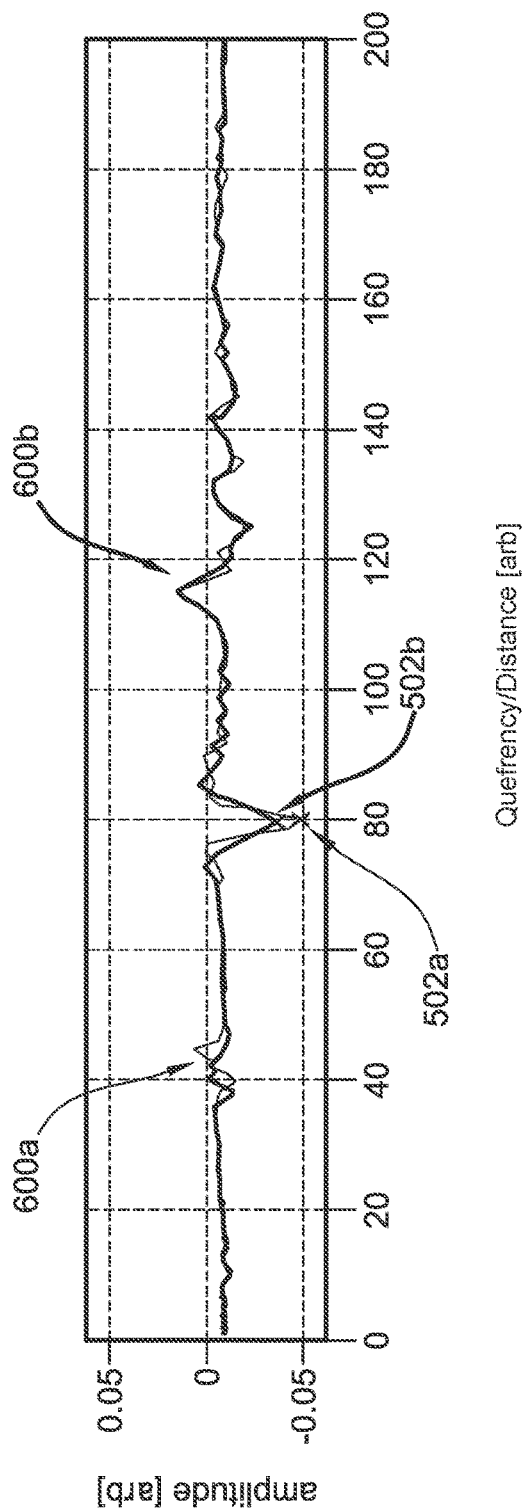
FIG. 9 is a plot of aligned windowed cepstrums of generated acoustic data, according to some implementations of the present disclosure.

Referring to FIG. 9, a further result of the windowing, as shown by the windowed cepstrum 600a relative to the windowed cepstrum 600b, is an alignment based on the fiducial points 502a and 502b. The alignment allows for further consistency in the additional analysis of the generated acoustic data and the characterizing of the analyzed acoustic data, as described below.

As discussed above, in one or more implementations, the respiratory therapy system 120 analyzing the generated acoustic data can include a deconvolution of the generated acoustic data prior to the windowing of the generated acoustic data. In one or more implementations, the deconvolution of the generated acoustic data can include calculating a cepstrum of the generated acoustic data. The cepstrum identifies a distance associated with the acoustic reflection, and the distance indicates a location of the one or more features of the user interface. More specifically, the cepstrum identifies one or more distances associated with each of a corresponding one or more acoustic reflections, thereby indicating a location of each of one or more physical features along the acoustic pathway of the acoustic signal. Calculating the cepstrum can be achieved by processing the acoustic reflection in a series of stages: calculate the frequency spectrum of the acoustic reflection via a fast Fourier transform; take the natural logarithm of the absolute magnitude of this frequency spectrum; and perform the inverse Fourier transform and calculate the real part of the signal to produce a cepstrum. This process may be repeated over multiple time intervals and an average cepstrum may be estimated. The resulting cepstrum signal transforms the acoustic reflection into the quefrency domain which is analogous to separating reflections in time and/or distance. In one or more implementations, the cepstrum can be calculated using a fast Fourier transform of 4096 samples of the acoustic reflection with, optionally, 50% overlap of the samples. These 4096 samples represent about 0.2 seconds of generated acoustic data.

In one or more implementations, the analyzing of the generated acoustic data can include calculating a derivative of the cepstrum to determine a rate of change of the cepstrum signal. The derivative of the cepstrum can provide additional information that is used to characterize the user interface, as described below with respect to step 406. The derivative of the cepstrum also allows the network to find alternate features from the same input In one or more implementations, the respiratory therapy system 120 analyzing the generated acoustic data can include normalizing the generated acoustic data. Normalizing the generated acoustic data can account for confounding conditions. The confounding conditions can be, for example, microphone gain, breathing amplitude, therapy pressure, varying conduit length, curled or stretched conduit, different therapy pressures, ambient temperature, or a combination thereof. In one or more implementations, the normalizing of the generated acoustic data can include subtracting a mean value from the generated acoustic data, dividing by a standard deviation of the generated acoustic data, or a combination thereof. The aim of the normalizing is to make all incoming of the cepstrums of the analyzed acoustic data of similar and magnitude and in a range that is natural for characterization, as further described below. In one or more implementations, the aim of the normalizing is to have the average of the cepstrum always be zero.

Figure 10:
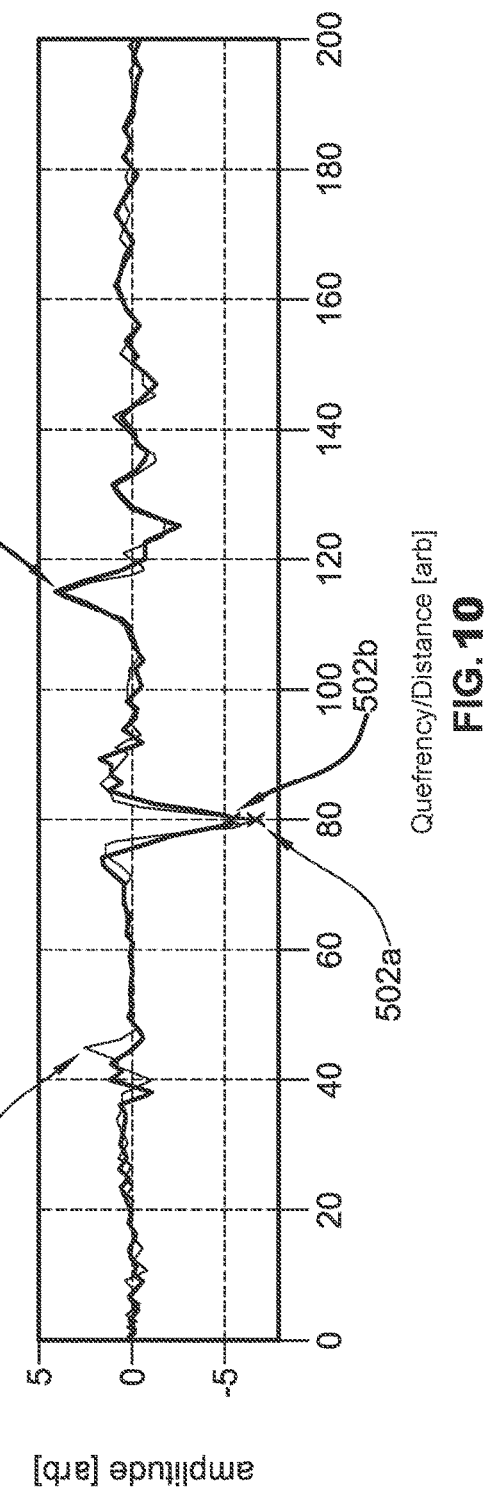
FIG. 10 is a plot of normalized windowed cepstrums of generated acoustic data, according to some implementations of the present disclosure.

Referring to FIG. 10, illustrated are the normalized cepstrums 800a and 800b, corresponding to cepstrums 500a and 500b, respectively. As shown by the values of the Y-axis in FIG. 10 relative to FIG. 9, the amplitudes have been adjusted so that the cepstrums are of similar magnitude and in a range that is natural characterization, as described below.

Referring back to FIG. 6, at step 406, the respiratory therapy system 120 characterizes the user interface based, at least in part, on the analyzed acoustic data. The characterizing of the user interface comprises inputting the analyzed acoustic data into a supervised machine learning model (e.g. a (deep) neural network such as a convolutional neural network) to determine the user interface. In one or more implementations, determining the user interface includes determining a form factor or type of the user interface (e.g. full face, nasal, pillow, etc.), a model of the user interface (e.g. AirFit™ F20 mask manufactured by ResMed), a size of one or more elements of the user interface, or a combination thereof.

In one or more implementations, the convolutional neural network (CNN) can include one or more convolutional and max pooling layers. In one or more implementations, the CNN can include one or more convolutional layers. In one or more implementations, the CNN can include N features. Each of the N features can be L samples in width. The CNN can further allow for a max pooling of M samples. Each feature of the N features is a unique plot or wave within the analyzed acoustic data, such as within the cepstrum. In one or more implementations, N can equal 64, such that the CNN can account for 64 unique plots or features within the analyzed acoustic data. Each sample of the L samples in width represents a data point generated based on the acoustic reflection. Thus, L samples represents L data points generated in response to the acoustic reflection. The L samples is matched roughly to the expected size of the features within the acoustic reflection. In one or more implementations, the L samples can be roughly correspond to about 25 cm in length. The M samples can be, for example, 20 samples, which allows for some natural time-invariance in the model to account for shifts between the different mask reflections. In one or more implementations, the ratio of N to M can be 1:1 to 4:1. In one or more implementations, the outputs of the convolutional layers can be fed into one or more fully-connected dense layers before a classification is made.

Although the disclosed embodiments have been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

In one or more implementations, the CNN can be trained based on augment training set by adding random circular shift 20 samples to the features that are used to train the CNN. Specifically, a transformation can be applied to the features within the data set that is used to train the CNN, which makes for a more robust to time parts of the acoustic signal shifting, shifting the acoustic data in the windows, adding noise, and other types of shift for a more robust system.

Although the focus of the present application is identifying the user interface, in one or more implementations, the systems and methods disclosed in the present application can be used to identify the conduit based on the same methods disclosed for identifying the user interface. For example, different conduits (e.g., different diameters, lengths, materials, etc.) can be used within the respiratory therapy system. The systems and methods can be used to determine the different conduits.

In one or more implementations, the conduit 126 can be identified instead of the user interface. Additional details related to identifying the conduit 126 can be found in U.S. Provisional App. No. 63/107,763 filed on Oct. 30, 2020, which is hereby incorporated by reference herein in its entirety. In one or more implementations, the conduit can be identified along with identifying the user interface. Where both are identified, the order of identification and include both being identified at the same time, or one being identified first (e.g., the conduit or the user interface) followed by the other.

In one or more implementations, identifying one of the conduit or the user interface can narrow down the possible choices from which to identify the other of the conduit or the user interface. For example, a specific conduit may be compatible with only a subset of all user interfaces for respiratory therapy systems. Accordingly, identifying the conduit can limit the subsequent identification of the user interface from among only the user interfaces within the subset. A similar narrowing, and thus simplification of characterization, can be achieved by first identifying the user interface, for subsequent identification of the conduit.

The characterization of the user interface described above focuses at the highest level generally on a type of the user interface, and can narrow down to the specific model, aesthetic style, etc. However, user interfaces, such as the user interface 124 in FIGS. 1 and 2, come in different categories, which can be considered a broader distinction of user interfaces than type (e.g., full face, nasal, nasal pillows, etc.), or at least as broad of a distinction as type. According to some implementations, the categories are defined, at least in part, as being directly connected user interfaces (referred to herein as "direct category" user interfaces) or indirectly connected user interfaces (referred to herein as "indirect category" user interfaces). In one or more implementations, the distinction of directly versus indirectly connected is based on the element(s) of the user interface that connect to the conduit of the respiratory therapy system. That is, the description of directly versus indirectly connected user interfaces relates to how pressurized air is delivered to the user from the end of the conduit of the respiratory therapy system and through the user interface. As will be described in greater detail below, directly connected user interfaces generally have the conduit of the respiratory therapy system connect directly with the cushion and/or the frame of the user interface (described below), optionally via a connector of the user interface. Thus, pressurized air is delivered directly from the conduit of the respiratory therapy system (optionally through a connector) into a chamber formed by the cushion (or cushion and frame) of the user interface against the user's face.

Figure 11A:
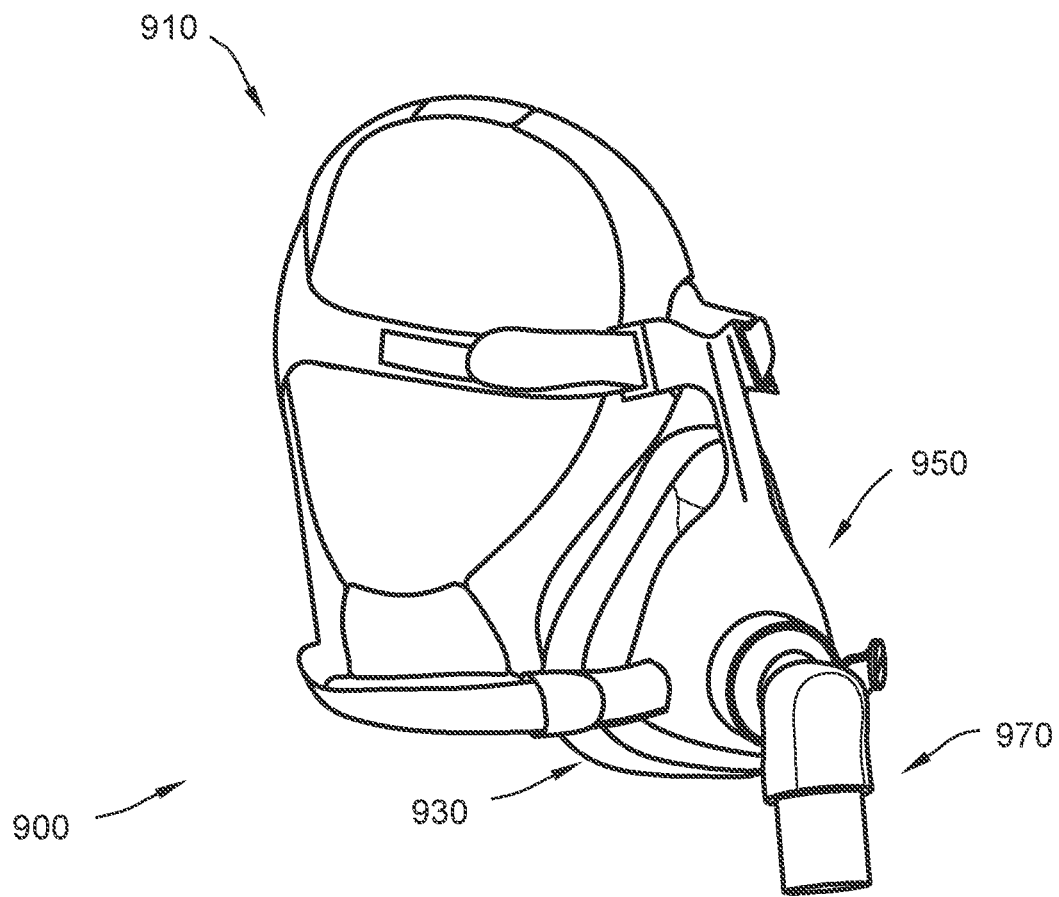
FIG. 11A is a perspective view of one category of user interfaces, according to some implementations of the present disclosure.
Figure 11B:
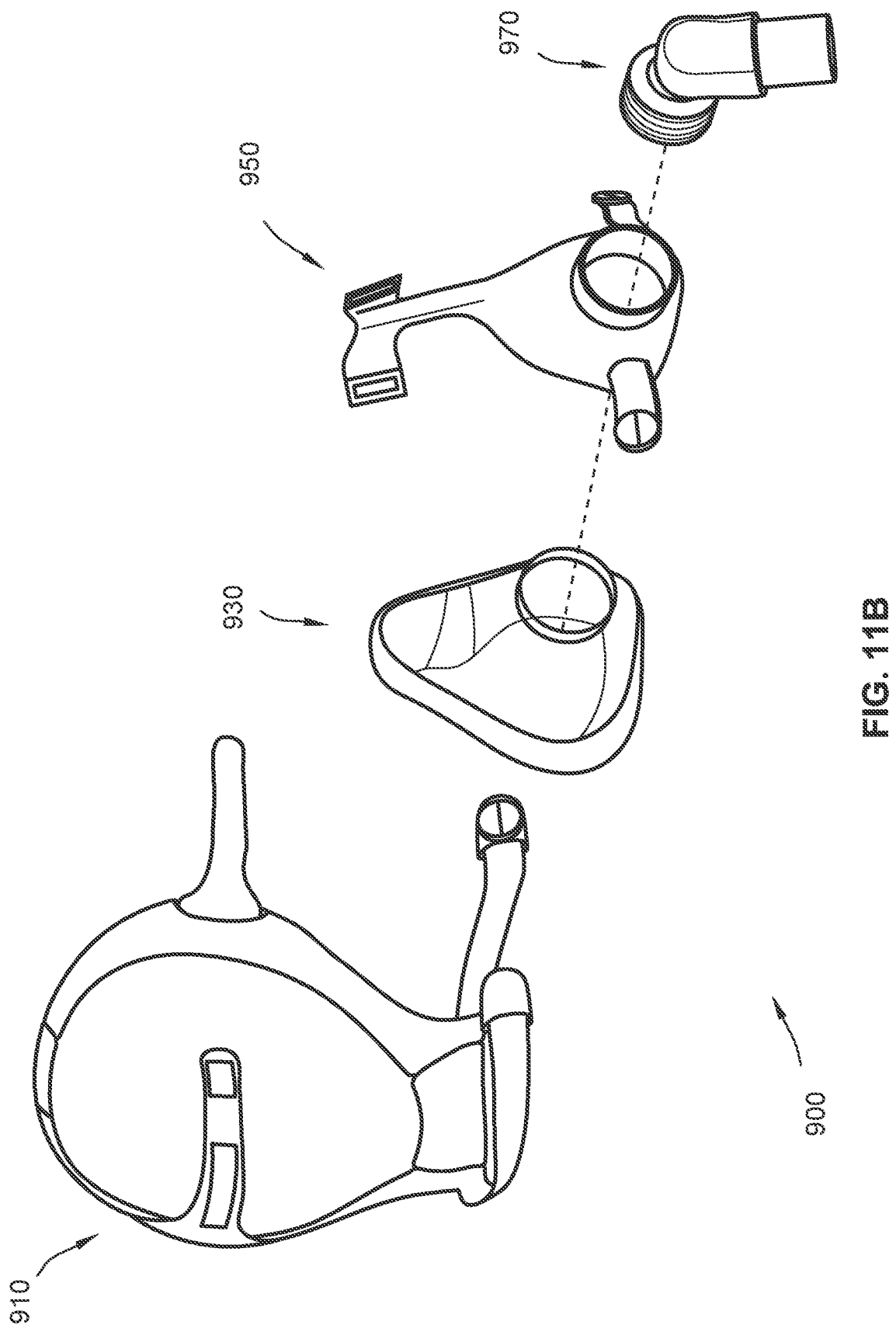
FIG. 11B is an exploded view of the user interface of FIG. 11A, according to some implementations of the present disclosure.

FIGS. 11A and 11B illustrate a perspective view and an exploded view, respectively, of one implementation of a directly connected user interface ("direct category" user interfaces), according to aspects of the present disclosure. The direct category of a user interface 900 generally includes a cushion 930 and a frame 950 that define a volume of space around the mouth and/or nose of the user. When in use, the volume of space receives pressurized air for passage into the user's airways. In some embodiments, the cushion 930 and frame 950 of the user interface 900 form a unitary component of the user interface. The user interface 900 assembly may further be considered to comprise a headgear 910, which in the case of the user interface 900 is generally a strap assembly, and optionally a connector 970. The headgear 910 is configured to be positioned generally about at least a portion of a user's head when the user wears the user interface 900. The headgear 910 can be coupled to the frame 950 and positioned on the user's head such that the user's head is positioned between the headgear 910 and the frame 950. The cushion 930 is positioned between the user's face and the frame 950 to form a seal on the user's face. The optional connector 970 is configured to couple to the frame 950 and/or cushion 930 at one end and to a conduit of a respiratory therapy device (not shown). The pressurized air can flow directly from the conduit of the respiratory therapy system into the volume of space defined by the cushion 930 (or cushion 930 and frame 950) of the user interface 900 through the connector 970). From the user interface 900, the pressurized air reaches the user's airway through the user's mouth, nose, or both. Alternatively, where the user interface 900 does not include the connector 970, the conduit of the respiratory therapy system can connect directly to the cushion 930 and/or the frame 950.

For indirectly connected user interfaces ("indirect category" user interfaces), and as will be described in greater detail below, the conduit of the respiratory therapy system connects indirectly with the cushion and/or frame of the user interface. Another element of the user interface—besides any connector—is between the conduit of the respiratory therapy system and the cushion and/or frame. This additional element delivers the pressurized air to the volume of space formed between the cushion (or cushion and frame) of the user interface and the user's face, from the conduit of the respiratory therapy system. Thus, pressurized air is delivered indirectly from the conduit of the respiratory therapy system into the volume of space defined by the cushion (or the cushion and frame) of the user interface against the user's face. Moreover, according to some implementations, the indirectly connected category of user interfaces can be described as being at least two different categories: "indirect headgear" and "indirect conduit". For the indirect headgear category, the conduit of the respiratory therapy system connects to a headgear conduit, optionally via a connector, which in turn connects to the cushion (or cushion and frame). The headgear is therefore configured to deliver the pressurized air from the conduit of the respiratory therapy system to the cushion (or cushion and frame) of the user interface. This headgear conduit within the headgear of the user interface is therefore configured to deliver the pressurized air from the conduit of the respiratory therapy system to the cushion of the user interface.

Figure 12A:
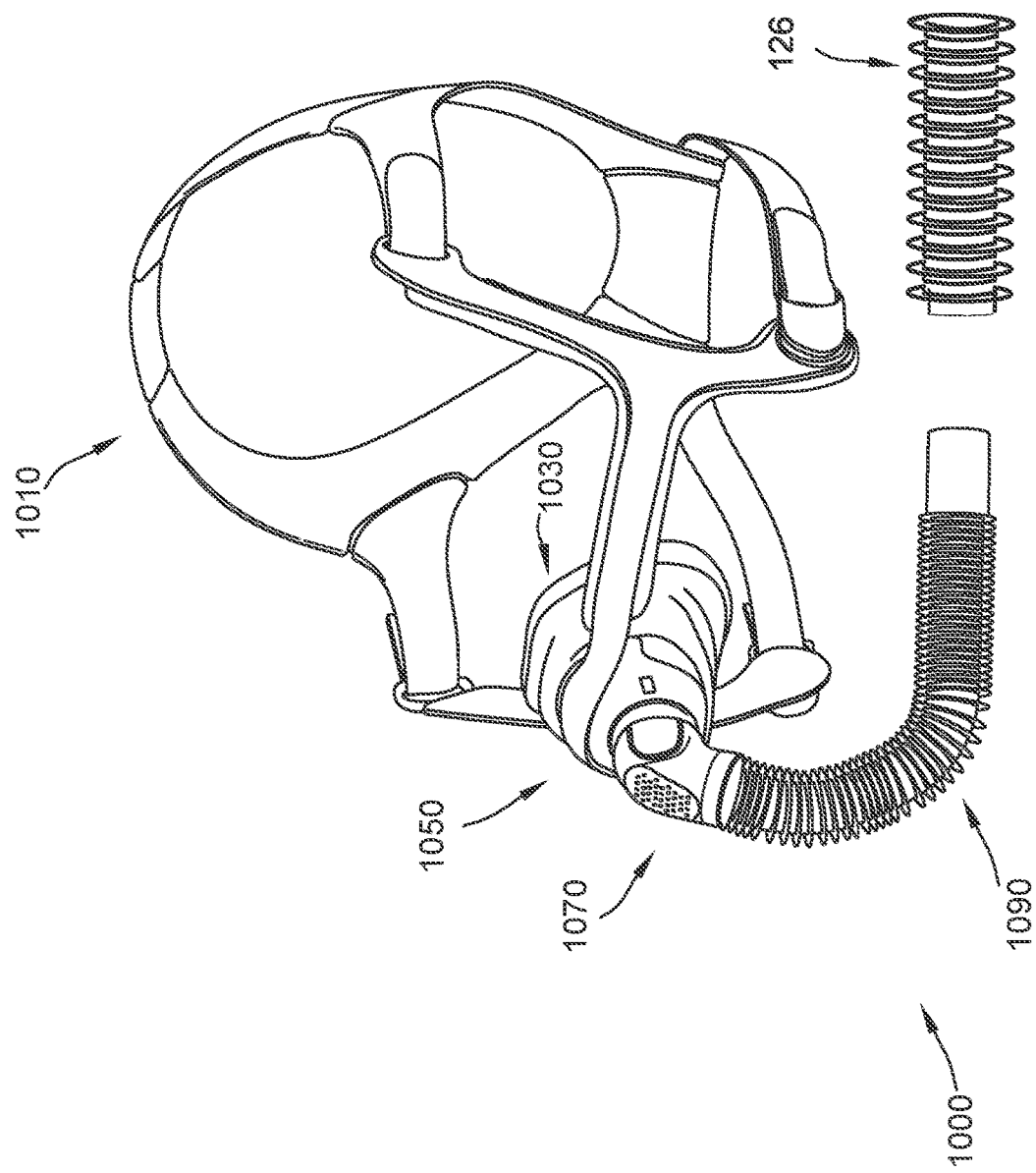
FIG. 12A is a perspective view of another category of user interfaces, according to some implementations of the present disclosure.
Figure 12B:
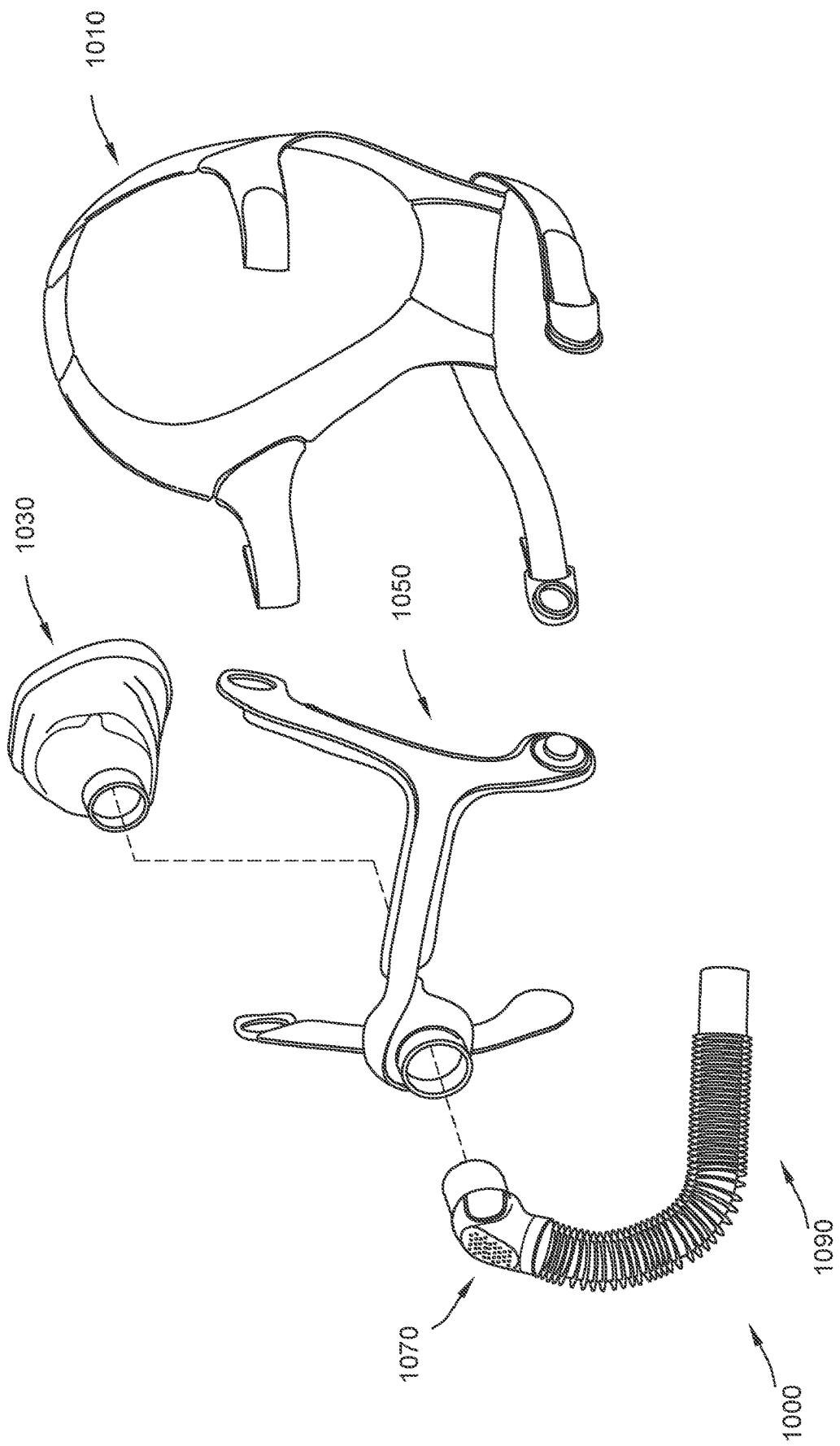
FIG. 12B is an exploded view of the user interface of FIG. 12A, according to some implementations of the present disclosure.

FIGS. 12A and 12B illustrate a perspective view and an exploded view, respectively, of one implementation of an indirect conduit user interface 1000, according to aspects of the present disclosure. The indirect conduit user interface 1000 includes a cushion 1030 and a frame 1050. In some embodiments, the cushion 1030 and frame 1050 form a unitary component of the user interface 1000. The indirect conduit user interface 1000 may further be considered to include a headgear 1010, such as a strap assembly, optionally a connector 1070, and a user interface conduit 1090 (often referred to in the art as a "minitube" or a "flexitube"). Generally, the user interface conduit is i) is more flexible than the conduit 126 of the respiratory therapy system, (ii)

has a diameter smaller than the diameter of the conduit 126 of the respiratory therapy system, or both (i) and (ii). The user interface conduit may also have a shorter length than the conduit. Similar to the user interface 900, the headgear 1010 is configured to be positioned generally about at least a portion of a user's head when the user wears the user interface 1000. The headgear 1010 can be coupled to the frame 1050 and positioned on the user's head such that the user's head is positioned between the headgear 1010 and the frame 1050. The cushion 1030 is positioned between the user's face and the frame 1050 to form a seal on the user's face. The optional connector 1070 is configured to couple to the frame 1050 and/or cushion 1030 at one end and to the conduit 1090 of the user interface 1000 at the other end. In other implementations, the conduit 1090 may connect directly to frame 1050 and/or cushion 1030. The conduit 1090, at the opposite end relative to the frame 1050 and cushion 1030, is configured to connect to the conduit 126 (FIG. 12A) of the respiratory therapy system (not shown). The pressurized air can flow from the conduit 126 (FIG. 12A) of the respiratory therapy system, through the user interface conduit 1090, and optionally the connector 1070, and into a volume of space define by the cushion 1030 (or cushion 1030 and frame 1050) of the user interface 1000 against a user's face. From the volume of space, the pressurized air reaches the user's airway through the user's mouth, nose, or both.

In view of the above configuration, the user interface 1000 is an indirectly connected user interface because pressurized air is delivered from the conduit 126 (FIG. 12A) of the respiratory therapy system (not shown) to the cushion 1030 (or cushion 1030 and frame 1050) through the user interface conduit 1090, rather than directly from the conduit 126 (FIG. 12A) of the respiratory therapy system.

Figure 13A:
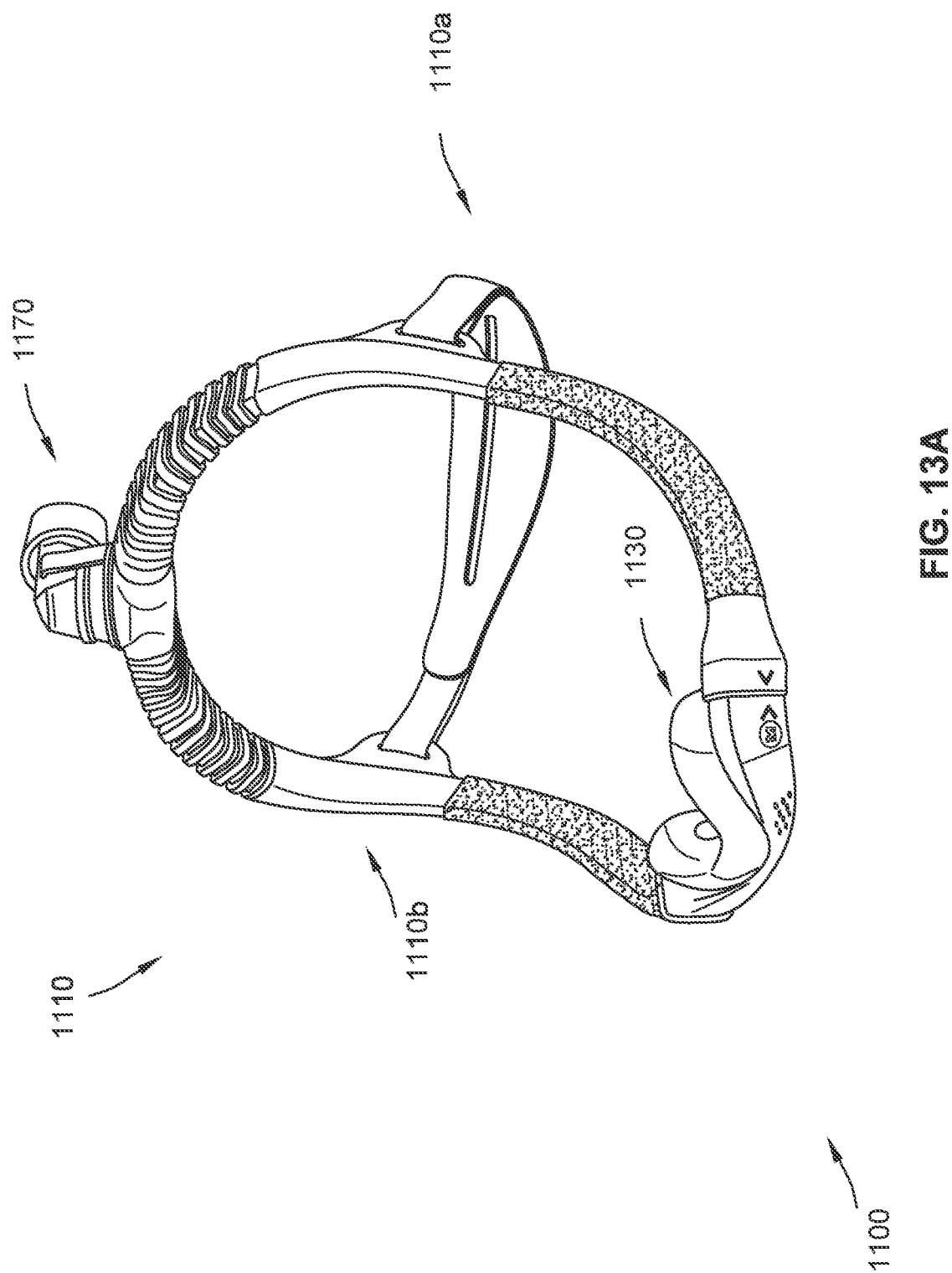
FIG. 13A is a perspective view of another category of user interfaces, according to some implementations of the present disclosure.
Figure 13B:
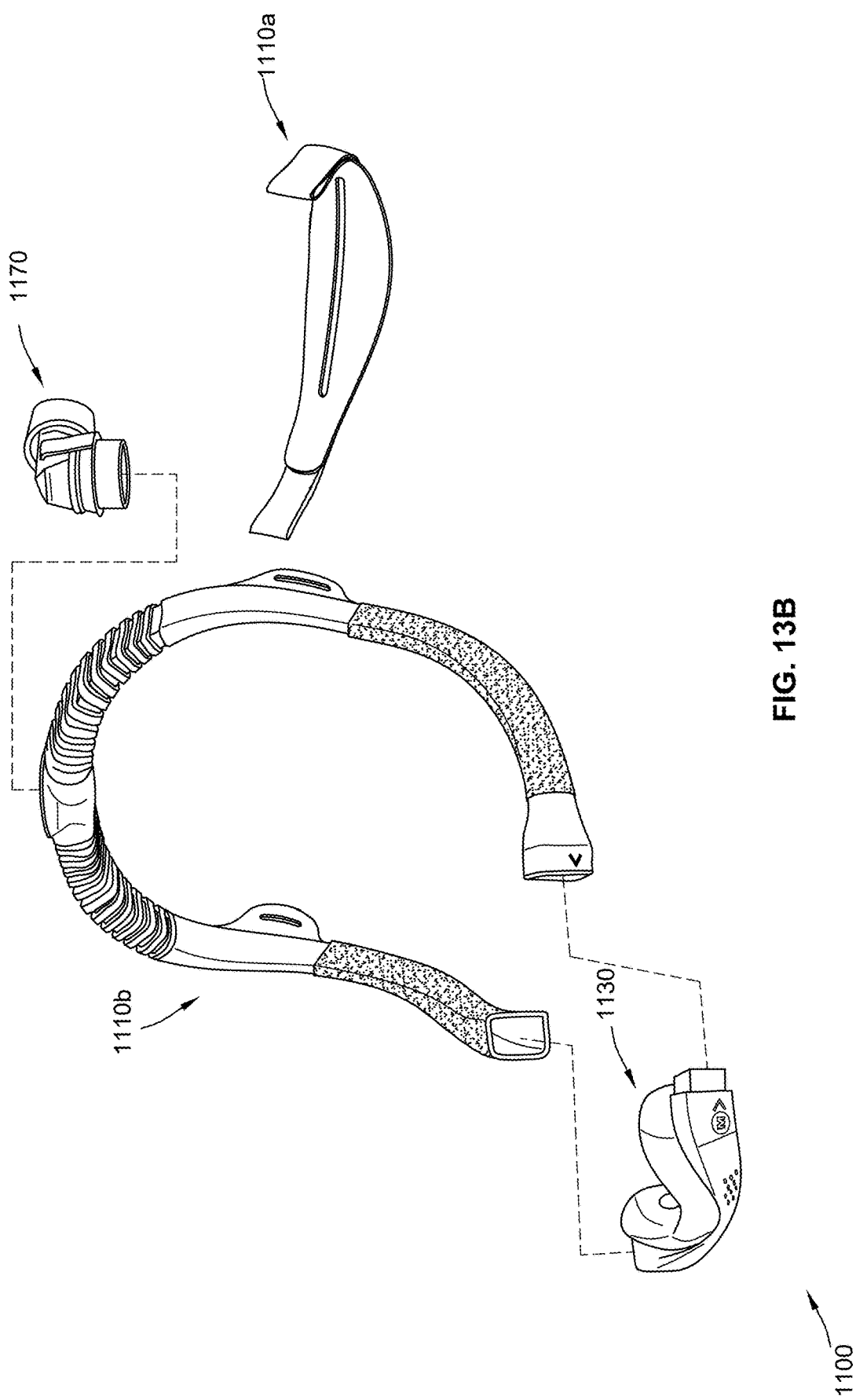
FIG. 13B is an exploded view of the user interface of FIG. 13A, according to some implementations of the present disclosure.

FIGS. 13A and 13B illustrate a perspective view and an exploded view, respectively, of one implementation of an indirect headgear user interface 1100, according to aspects of the present disclosure. The indirect headgear user interface 1100 includes a cushion 1130. The indirect headgear user interface 1100 may further be considered to comprise headgear 1110 (which can comprise strap 1110a and a headgear conduit 1110b, and optionally a connector 1170. Similar to the user interfaces 900 and 1000, the headgear 1110 is configured to be positioned generally about at least a portion of a user's head when the user wears the user interface 1100. The headgear 1110 includes a strap 1110a that can be coupled to the headgear conduit 1110b and positioned on the user's head such that the user's head is positioned between the strap 1110a and the headgear conduit 1110b. The cushion 1130 is positioned between the user's face and the headgear conduit 1110b to form a seal on the user's face. The connector 1170 is configured to couple to the headgear 1110 at one end and a conduit of the respiratory therapy system at the other end. In other implementations, the connector 1170 can be optional and the headgear 1110 can alternatively connect directly to conduit of the respiratory therapy system. The headgear conduit 1110b may be configured to deliver pressurized air from the conduit of the respiratory therapy system to the cushion 1130, or more specifically, to the volume of space around the mouth and/or nose of the user and enclosed by the user cushion. Thus, the headgear conduit 1110b is hollow to provide a passageway for the pressurized air. Both sides of the headgear conduit 1110b can be hollow to provide two passageways for the pressurized air. Alternatively, only one side of the headgear conduit 1110b can be hollow to provide a single passageway. In the implementation illustrated in FIGS. 13A and 13B, headgear conduit 1110b comprises two passageways which, in use, are positioned at either side of a user's head/face. Alternatively, only one passageway of the headgear conduit 1110b can be hollow to provide a single passageway. The pressurized air can flow from the conduit of the respiratory therapy system, through the connector 1170 (if present) and the headgear conduit 1110b, and into the volume of space between the cushion 1130 and the user's face. From the volume of space between the cushion 1130 and the user's face, the pressurized air reaches the user's airway through the user's mouth, nose, or both.

In view of the above configuration, the user interface 1100 is an indirect headgear user interface because pressurized air is delivered from the conduit of the respiratory therapy system to the volume of space between the cushion 1130 and the user's face through the headgear conduit 1110b, rather than directly from the conduit of the respiratory therapy system to the volume of space between the cushion 1130 and the user's face.

In one or more implementations, the distinction between the direct category and the indirect category can be defined in terms of a distance the pressurized air travels after leaving the conduit of the respiratory therapy device and before reaching the volume of space defined by the cushion of the user interface forming a seal with the user's face, exclusive of a connector of the user interface that connects to the conduit. This distance is shorter, such as less than 1 centimeter (cm), less than 2 cm, less than 3 cm, less than 4 cm, or less than 5 cm, for direct category user interfaces than for indirect category user interfaces. This is because the pressurized air travels through the additional element of, for example, the user interface conduit 1090 or the headgear conduit 1110b between the conduit of the respiratory therapy system before reaching the volume of space defined by the cushion (or cushion and frame) of the user interface forming a seal with the user's face for indirect category user interfaces.

Figure 14A:
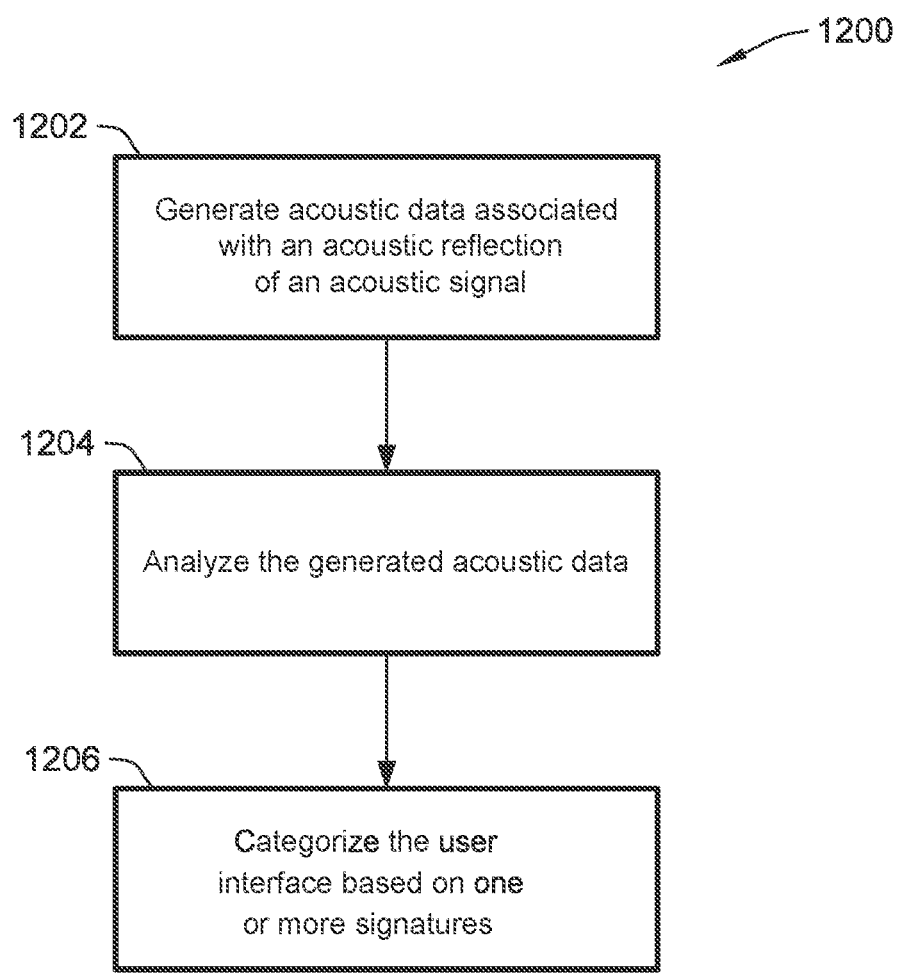
FIG. 14A is a flow diagram of a method for categorizing a user interface, according to some implementations of the present disclosure.

FIG. 14A is a flow diagram of a method 1200 for categorizing a user interface, according to aspects of the present disclosure. For purposes of convenience, the following description will be in reference to the method 1200 being performed by a respiratory therapy system, such as the respiratory therapy system 120. However, one or more other devices can perform the method 1200, such as one or more user devices 170. For example, such user devices 170 can communicate with the respiratory therapy system 120 for analyzing and classifying the data further discussed below.

At step 1202, the respiratory therapy system 120 generates acoustic data associated with an acoustic reflection of an acoustic signal. Similar to step 402 above, the acoustic data can be generated based on an acoustic transducer detecting the acoustic reflection. For example, the acoustic transducer can be a microphone that converts the pressure waves of the acoustic reflection into electrical signals representing the data. The acoustic reflection is indicative of, at least in part, one or more features of a user interface coupled to a respiratory therapy device via a conduit. As the acoustic signal travels down the conduit, the acoustic signal interacts with one or more features of the conduit, one or more features of the connection between the conduit and the user interface, one or more features of the user interface, etc. The interactions can cause the acoustic signal to reflect, thereby generating the acoustic reflection. Because the acoustic reflection is caused, at least in part, by the one or more features of the user interface, the acoustic reflection is indicative of the one or more features of the user interface.

In one or more implementations, the acoustic signal can be emitted into the conduit connected to the user interface via an audio transducer, such as a speaker. Alternatively, or in addition, the acoustic signal can be emitted into the conduit via a motor of the respiratory therapy device connected to the conduit. For example, the motor of the respiratory therapy device can emit sound as it forces air through the conduit. The emitted sound can be the acoustic signal, or at least part of the acoustic signal.

In one or more implementations, the acoustic signal can be a sound audible to a human (e.g., an average human with average human hearing). A sound is audible to a human when the sound has an amplitude that is loud enough for detection by the human and when it has a frequency within the frequency range of human hearing, which is generally about 20 Hz to about 20,000 Hz.

In one or more implementations, the acoustic signal can be a sound that is inaudible to a human (e.g., an average human with average human hearing). A sound is inaudible when the sound has an amplitude that is less than the lowest perceptible amplitude of a human. Alternatively, or in addition, a sound is inaudible to a human when the sound has a frequency that is outside of the frequency range of human hearing, which, as stated above, is about 20 Hz to about 20,000 Hz. For example, in one or more implementations, the acoustic signal can be an ultrasonic sound that has a frequency that is higher than the highest perceptible frequency for human hearing.

In one or more implementations, the method 1200 can be performed when the user interface is connected or worn by a user. In other words, the acoustic signal can be emitted, and the acoustic data can be generated based on the acoustic reflection with the user interface connected or coupled to the user. Further, the user interface can be connected or coupled to the user while the respiratory therapy system is providing therapy to the user, before providing therapy to the user, or after providing therapy to the user. For example, the flow of pressurized air can be provided through the conduit and into the user interface during the generation of the acoustic data. Providing the therapy may generate the acoustic signal, such as by the motor of the respiratory therapy device emitting the acoustic signal. Alternatively, the acoustic signal can be emitted in the conduit during an absence of a flow of pressurized air through the conduit and into the user interface.

Alternatively, the method can be performed when the user interface is not connected or coupled to a user. Specifically, the acoustic reflection that is indicative of one or more features of the user interface does not require the presence of the user. Accordingly, the method 1200 can be performed prior to the user wearing the user interface, or after the user removes the user interface.

Although step 1202 is described as being based on an acoustic signal and an acoustic reflection, in one or more implementations, the generated acoustic data can be generated from a plurality of acoustic reflections from a plurality of acoustic signals. The acoustic signals can be the same acoustic signal that is repeatedly emitted, or can be different acoustic signals that are emitted together, forming a single acoustic signal, or can be emitted separately. When there are multiple acoustic signals for multiple acoustic reflections, the generated acoustic data can be an average of the plurality of acoustic reflections from the plurality of the acoustic signals.

In one or more implementations, the generated acoustic data can include a primary reflection within the acoustic reflection of the acoustic signal. Additionally, or in the alternative, the generated acoustic data can include a secondary reflection within the acoustic reflection of the acoustic signal. Additionally, or in the alternative, the generated acoustic data can include a tertiary reflection within the acoustic reflection of the acoustic signal. The analysis that is conducted in one or more of the following steps can be from the primary, secondary, or tertiary reflections, or combinations thereof; such as the primary and the secondary reflection.

Although step 402 of the method 400 in FIG. 6 and step 1202 of the method 1200 in FIG. 14A are described in different portions of the specification herein and illustrated as different steps in different flow diagrams, in one or more implementations, step 402 and step 1202 can be the same step.

At step 1204, the respiratory therapy system 120 analyzes the generated acoustic data to correlate the one or more features of the user interface to one or more signatures within the generated acoustic data. The one or more signatures can include, for example, a maximum magnitude of a transform, a minimum magnitude of a transform, a standard deviation of a transform, a skewness of a transform, a kurtosis of a transform, a median of an absolute value of a transform, a sum of the absolute value of a transform, a sum of a positive area of a transform, a sum of a negative area of a transform, a fundamental frequency, an energy corresponding to the fundamental frequency, a mean energy, at least one resonant frequency of a combination of the conduit and the user interface, a change in the at least one resonant frequency, a number of peaks within a range, a peak prominence, distance between peaks, or a combination thereof. Generally, a signature can be made up of one or more acoustic features within the acoustic data. In one or more implementations, one or more of the signatures can be changes in one or more of the above aspects over time. The changes of the aspects over time can be considered one or more signatures specific to a specific category because changes in the aspects over time can be specific to a category. The changes can be during multiple iterations of the method 1200, such as consecutive iterations over the course of a few minutes; or during multiple iterations of the method 1200 over the course of a sleep session or a night; or during multiple iterations of the method 1200 over the course of several nights, weeks, months, years, etc.

In one or more implementations, analyzing the generated acoustic data includes generating a spectrum of the generated acoustic data, such as calculating a transform (e.g., Discrete Fourier Transform DFT, or Discrete Cosine Transform DCT) of the generated acoustic data. Thereafter, analyzing the generated acoustic data can further include calculating a logarithm of the spectrum. Thereafter, analyzing the generated acoustic data can include calculating a cepstrum of the logarithm spectrum, such as calculating an inverse transform (e.g., iDFT or iDCT) of the logarithm spectrum. The calculated cepstrum can then be analyzed for one or more signatures that can be used to categorize the user interface. A non-linear operation may be used in place of the logarithm calculation.

In one or more implementations, the analysis of the generated acoustic data does not require analyzing all of the generated acoustic data. For example, in one or more implementations, analyzing the generated acoustic data can include selecting a segment of the above-described spectrum. After selecting the segment, the analysis can further include calculating a direct transform (e.g., DFT or DCT) of the segment of the spectrum. From the direct transform, the one or more features of the user interface can be correlated to one or more signatures within the Fourier transform of the segment to identify the category of the user interface.

Alternatively, analyzing the generated acoustic data can include selecting a segment of the log spectrum of the generated acoustic data described above. From the log spectrum, the analysis can include calculating a transform of the log spectrum, such as a Fourier transform of the log spectrum. Alternatively, the analysis can include calculating an inverse transform of the log spectrum, or an inverse transform of the transform of the log spectrum.

Figure 14B:
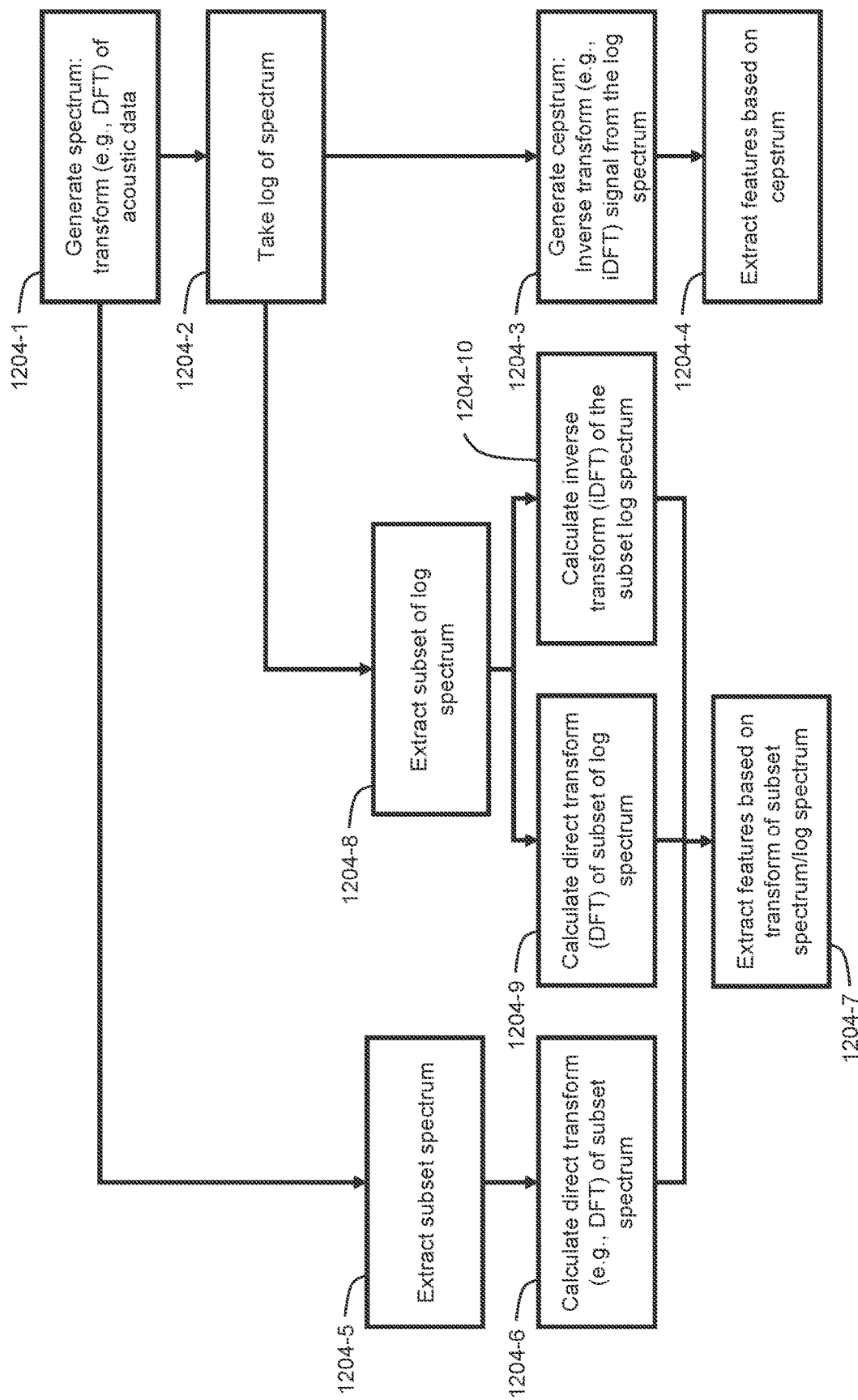
FIG. 14B is a flow diagram of a method for analyzing generated acoustic data, according to some implementations of the present disclosure.

In one or more specific implementations, FIG. 14B shows a flow diagram of a specific method for analyzing the generated acoustic data from step 1202, according to some implementations of the present disclosure. The method of FIG. 14B can be a sub-method within the step 1204 of the method of FIG. 14A.

At step 1204-1, a spectrum is generated from the acoustic data. For example, a transform, such as DFT, can be generated from the acoustic data. At step 1204-2, the log is taken from the spectrum generated at step 1204-1. Thereafter, at step 1204-3, a cepstrum can be generated from the log spectrum of step 1204-2. At step 1204-4, one or more signatures can then be identified from the cepstrum generated at step 1204-3.

Figure 22:
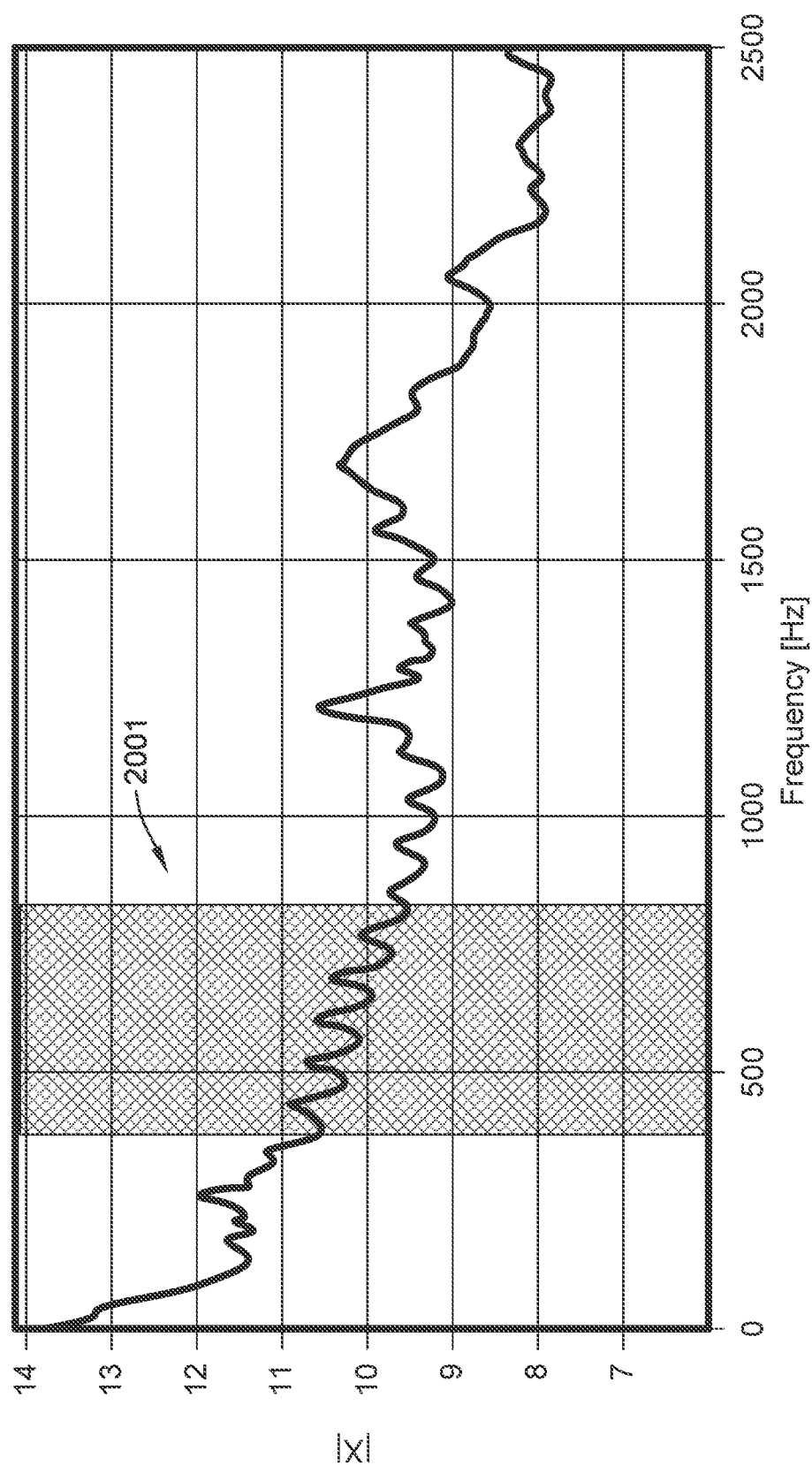
FIG. 22 is a plot of a log spectrum of generated acoustic data, according to some implementations of the present disclosure.
Figure 23:
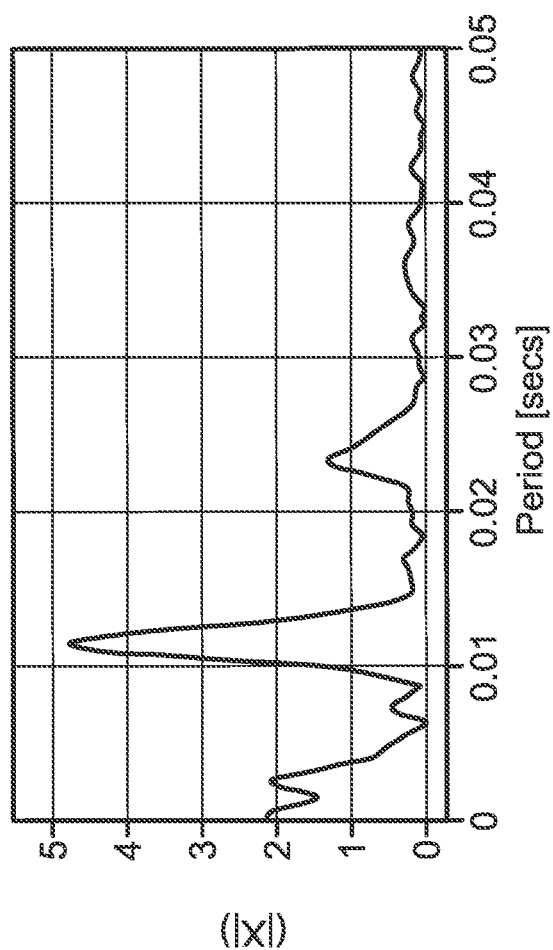
FIG. 23 is a plot of a transform of a segment of the log spectrum illustrated in FIG. 22, according to some implementations of the present disclosure.

Referring back to step 1204-1, rather than proceeding with step 1204-2, instead, at step 1204-5, a subset of the spectrum can be extracted, as discussed further below and with respect to FIGS. 22 and 23. At step 1204-6, there after a direct transform, such as a DFT, can be calculated from the subset spectrum. At step 1204-7, one or more signatures can then be identified from the direct transform of the subset spectrum generated at step 1204-6.

Referring back to step 1204-2, rather than proceeding with step 1204-3, instead, at step 1204-8, a subset of the log spectrum can be extracted, as discussed further below and with respect to FIGS. 22 and 23. Thereafter, a step 1204-9, a direct transform, such as a DFT, can be calculated from the subset log spectrum. Alternatively, at step 1204-10, an inverse transform, such as iDFT, can be calculated from the subset log spectrum. After step 1204-9 and step 1204-10, one or more signatures can then be identified from either the direct transform or inverse transform from the subset log spectrum at step 1204-7.

Referring back to FIG. 14A, the segment of the generated acoustic signal discussed above can be selected by trimming the generated acoustic data based on where within the generated acoustic data the one or more signatures that indicate the category of the user interface are generally located. For example, FIG. 22 illustrates a spectrum of exemplary generated acoustic data. The hashed segment 2001 of the plot of the generated acoustic data may be the segment of the generated acoustic data that corresponds to acoustic data associated with features of the user interface that can be used to categorize the user interface. Accordingly, the generated acoustic data before and after the segment 2001 can be removed and only the generated acoustic data within the segment 2001 may be analyzed (or further analyzed) for categorizing the user interface. FIG. 23 illustrates a further transform of the segment 2001 in FIG. 22, such as an inverse Fourier transform of the log spectrum of the generated acoustic data plotted in FIG. 22. From the plot in FIG. 23, signatures of the plot can be used to categorize the user interface.

Specifically, at step 1206, the respiratory therapy system 120 categorizes the user interface based, at least in part, on the one or more signatures. As discussed above, the category of the user interface can be, for example, direct, indirect frame, or indirect conduit. The one or more signatures can be fed into, for example, a machine learning model (e.g., linear regression, logistic regression, nearest neighbor, decision trees, PCA, naive Bayes classifier, and k-means clustering, random forest, etc.) and return a category (e.g., direct, indirect conduit, indirect frame). In one or more implementations, categorizing the user interface can be based, at least in part, on the one or more signatures matching one or more known signatures of one or more user interfaces of known categories. The user interface can be determined based on the known category of user interface with the matching signatures.

In one or more implementations, the signatures used to categorize the user interface can relate to the primary reflection within the generated acoustic data. Alternatively, the signatures used to categorize the user interface can relate to a reflection other than the primary reflection within the generated acoustic data, such as a secondary reflection, a tertiary reflection, etc. Alternatively, the signatures used to categorize the user interface can include combinations of reflections, such as the first and second reflections; the first and third reflections; the first, second and third reflections; the second and third reflections, etc.

Figure 15:
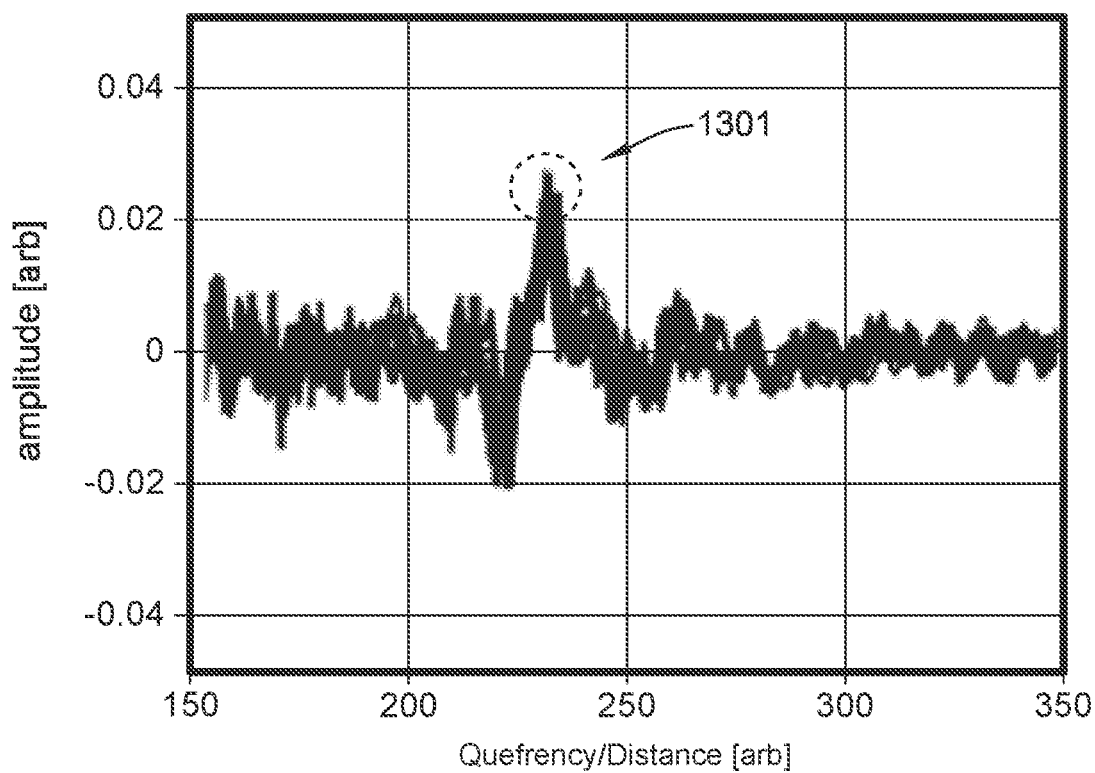
FIG. 15 is a plot of calculated cepstrums for a user interface, according to some implementations of the present disclosure.
Figure 16:
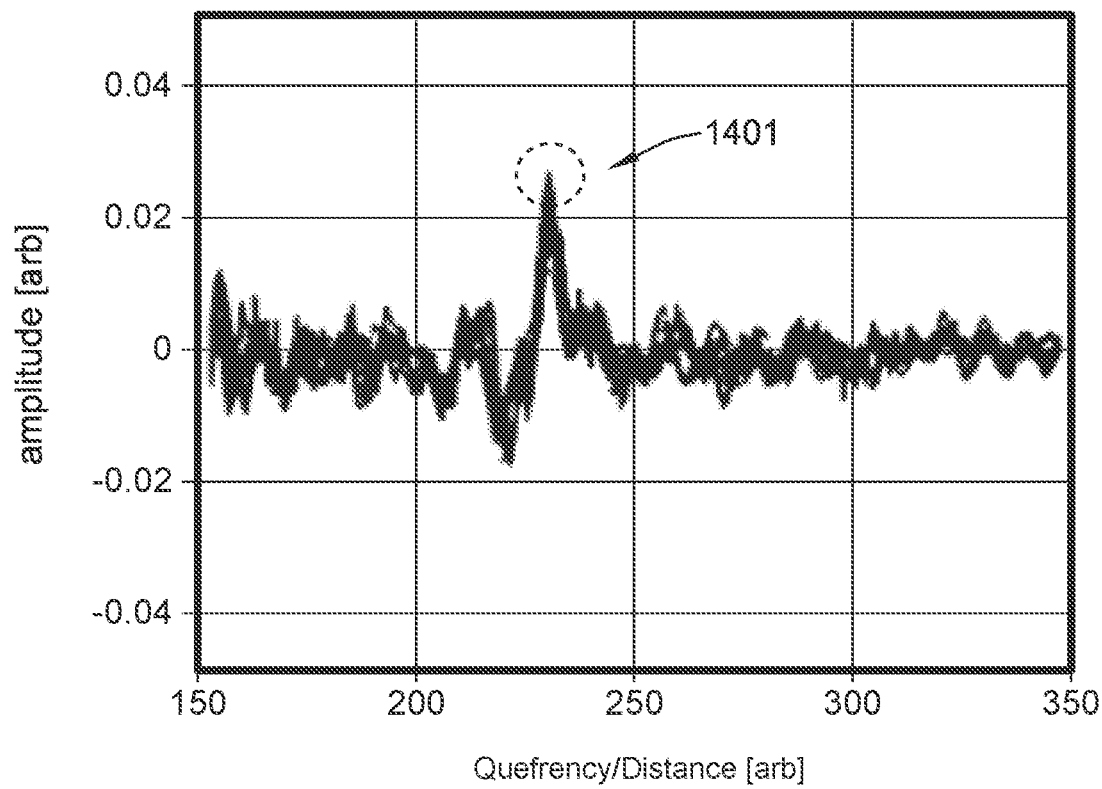
FIG. 16 is a plot of additional calculated cepstrums for a user interface, according to some implementations of the present disclosure.

According to some implementations, the direct category can include the one or more signatures having a maximum magnitude of the cepstrum larger than a threshold. FIGS. 15 and 16 are plots of calculated cepstrums for direct user interfaces, according to some implementations of the present disclosure. Referring to FIG. 15, the plot shows the cepstrum for a direct category user interface (full face mask, specifically the AirFit™ F10 full face ask by ResMed), such as what is illustrated in FIGS. 11A and 11B. The maximum magnitude of the cepstrum satisfies a threshold (e.g., is above), which indicates, at least in part, that the associated user interface is a direct user interface. For example, the threshold can be the value 0.2 in the y-axis. Because the largest peak 1301 is above the 0.2 threshold, the cepstrum indicates that the user interface is the direct category. Similarly, for FIG. 16, the plot shows the calculated cepstrum for another direct category user interface (nasal mask, specifically the AirFit™ N20 Classic nasal mask by ResMed). The maximum magnitude of the cepstrum satisfies a threshold (e.g., is above), such as the same threshold for FIG. 15 of 0.2. Specifically, the largest peak 1401 is above the same 0.2 threshold. Thus, the cepstrum indicates that the user interface is the direct category.

Figure 17:
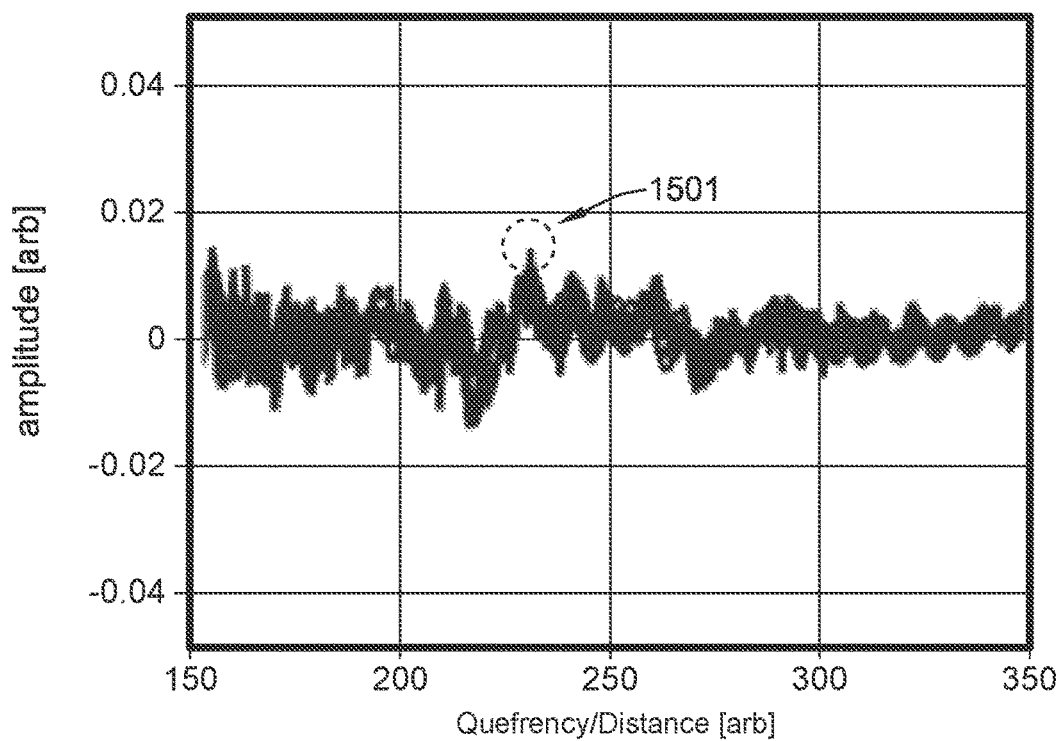
FIG. 17 is a plot of additional calculated cepstrums for a user interface, according to some implementations of the present disclosure.
Figure 18:
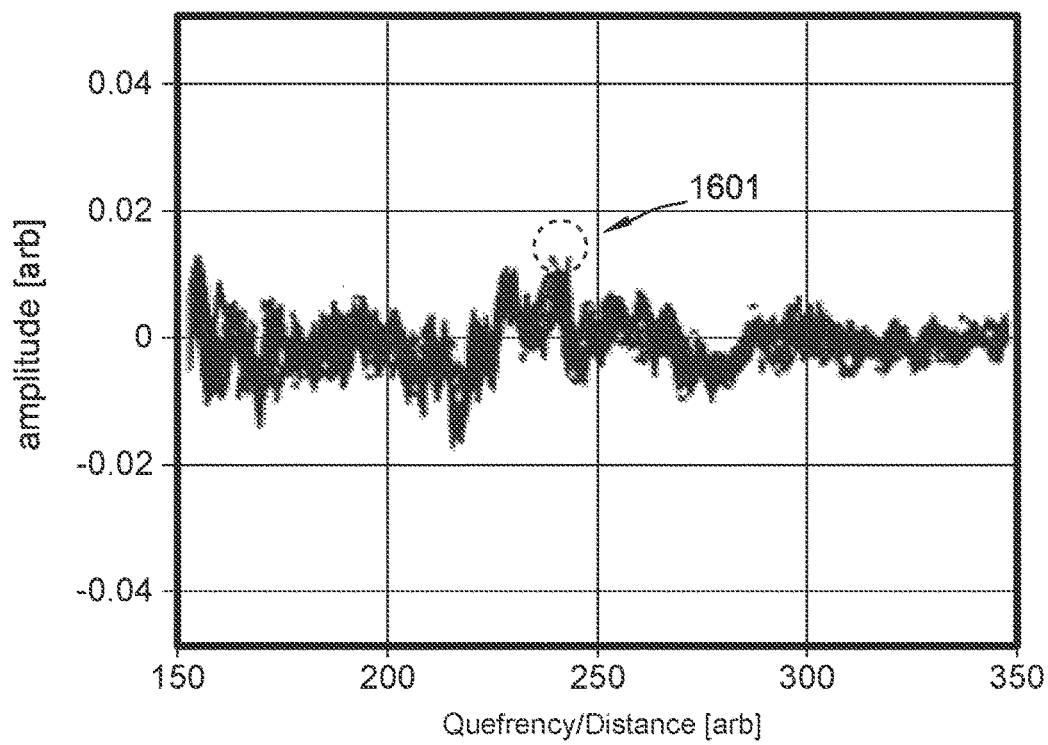
FIG. 18 is a plot of additional calculated cepstrums for a user interface, according to some implementations of the present disclosure.

According to some implementations, the indirect frame category includes one or more signatures with a mean cepstrum value below a threshold. FIGS. 17 and 18 are plots of example cepstrums for indirect frame category user interfaces, according to some implementations of the present disclosure. Referring to FIG. 17, the plot shows the cepstrum for an indirect frame category user interface (full face mask, specifically the AirFit™ F30$i$ full face mask by ResMed), such as what is illustrated in FIGS. 12A and 12B. The maximum magnitude at the peak 1501 of the cepstrum satisfies a threshold (e.g., is below), which indicates that the associated user interface is an indirect frame user interface. For example, the threshold can be the value 0.2 in the y-axis. Because no peak is above the 0.2 threshold, the cepstrum satisfies the threshold and indicates, at least in part, that the user interface is the indirect frame category. Moreover, the plot of the cepstrum in FIG. 17 shows a dispersed cepstral signature. This too indicates, at least in part, that the user interface is the indirect frame category. Referring to FIG. 18, the plot shows the cepstrum for another indirect frame category user interface (nasal mask, specifically the AirFit™

N30i nasal mask by ResMed). The maximum magnitude at the peak 1601 of the cepstrum satisfies the threshold of being below 0.2. The plot of the cepstrum in FIG. 18 also shows a dispersed cepstral signature, which indicates, at least in part, that the user interface is the indirect frame category.

Figure 19:
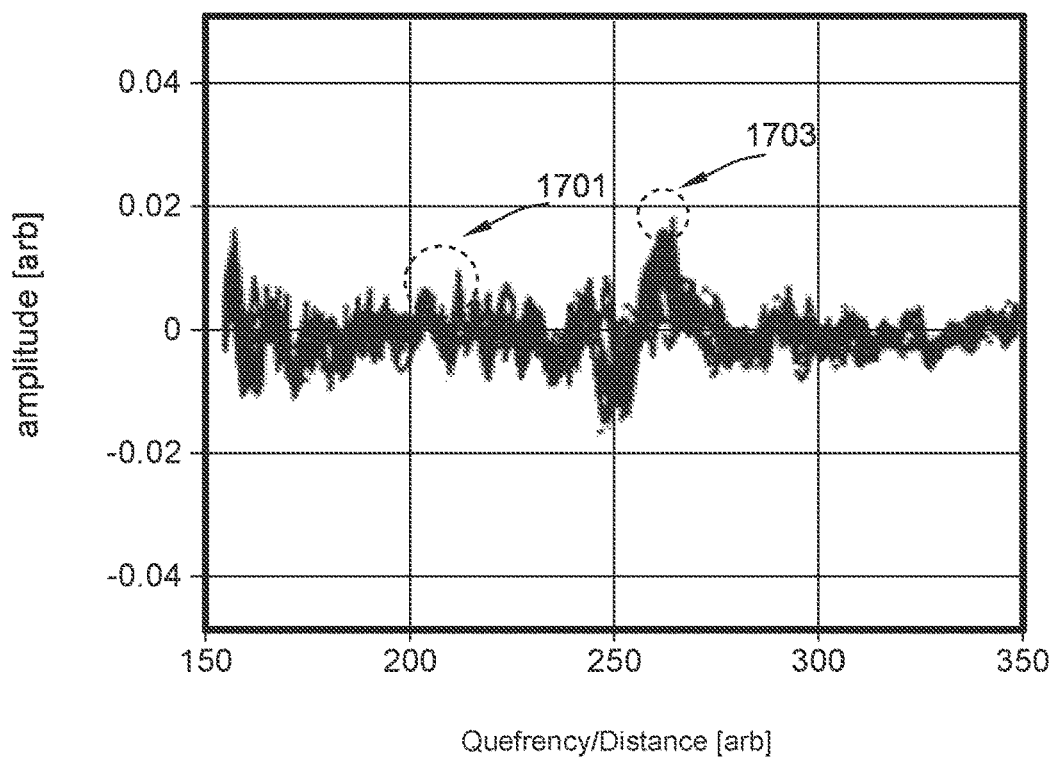
FIG. 19 is a plot of additional calculated cepstrums for a user interface, according to some implementations of the present disclosure.
Figure 20:
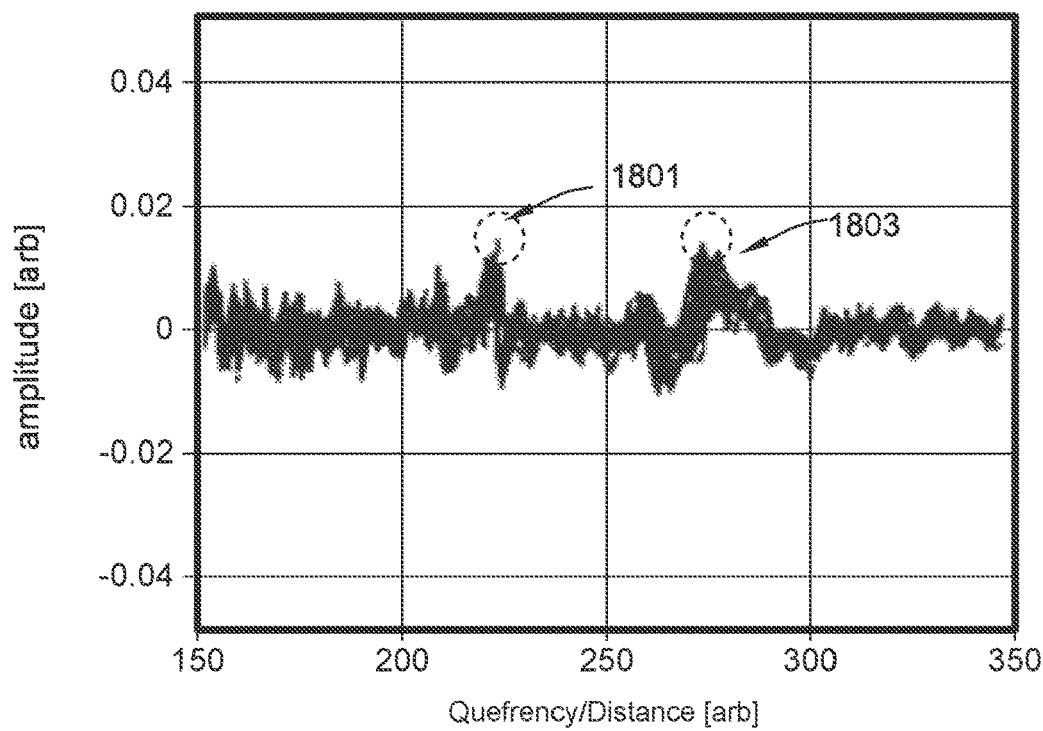
FIG. 20 is a plot of additional calculated cepstrums for a user interface, according to some implementations of the present disclosure.

According to some implementations, the indirect conduit category can include one or more signatures satisfying a threshold number of peaks. The is a result of, for example, the connection between the conduit of the respiratory therapy system and the conduit of the user interface, and the connection of the conduit of the user interface and the connector of the user interface. FIGS. 19 and 20 are plots of example cepstrums for indirect frame conduit user interfaces, according to some implementations of the present disclosure. Referring to FIG. 19, the plot shows the cepstrum for an indirect conduit category user interface (nasal mask, specifically AirFitN20™), such as what is illustrated in FIGS. 13A and 13B. The cepstrum includes two prominent peaks 1701 and 1703. The prominent peak 1701 may represent, for example, the connection between the conduit of the respiratory therapy system and the conduit of the user interface. The prominent peak 1703 may represent, for example, the connection of the conduit of the user interface and the connector of the user interface. Thus, based on the presence of these two prominent peaks 1701 and 1703, the cepstrum indicates that the category of the user interface is indirect conduit.

Referring to FIG. 20, and similar to FIG. 19, the prominent peak 1801 may represent, for example, the connection between the conduit of the respiratory therapy system and the conduit of the user interface. The prominent peak 1803 may represent, for example, the connection of the conduit of the user interface and the connector of the user interface. Thus, based on the presence of these two prominent peaks 1801 and 1803, the cepstrum indicates that the category of the user interface is indirect conduit.

Based on the above analysis, the signatures in the analyzed generated acoustic data can indicate the category of the user interface. In one or more implementations, a single signature can be used to categorize a user interface, such as a prominent peak satisfying a large threshold. However, in one or more implementations, multiple signatures can be used to categorize a user interface. In one or more implementations, the categorizing can be similar to the characterizing. For example, the categorizing can be performed based on inputting the analyzed acoustic data into a supervised machine learning model (e.g. a (deep) neural network such as a convolutional neural network) to determine the user interface.

Figure 21:
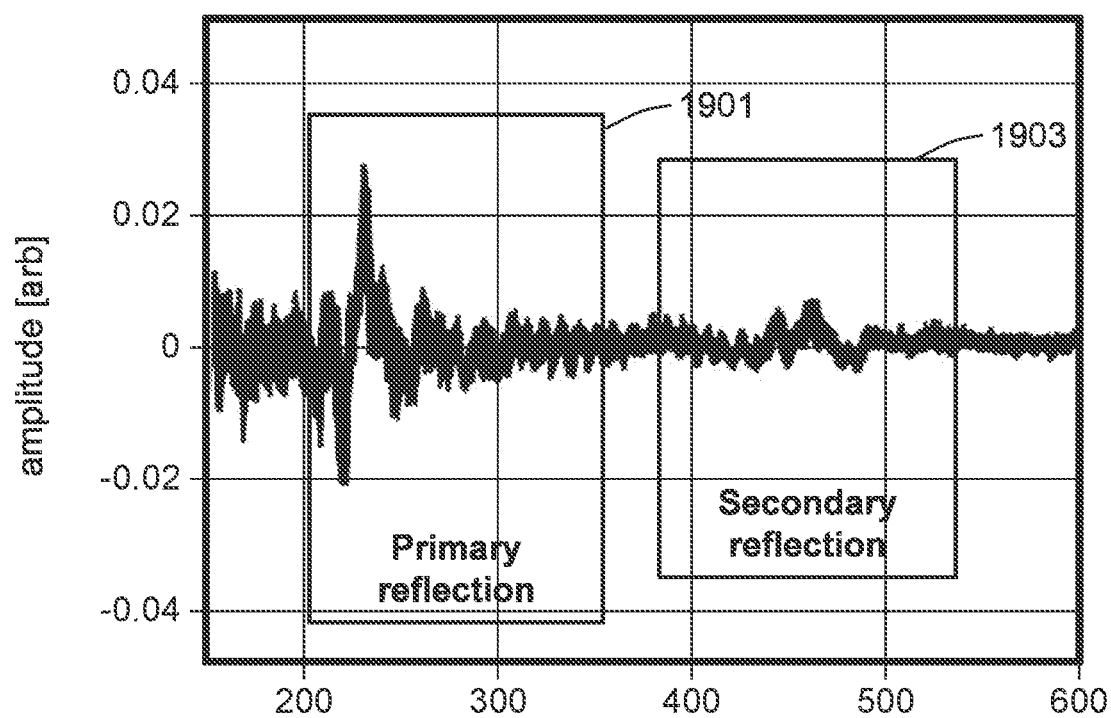
FIG. 21 is a plot of calculated cepstrums illustrating primary and secondary reflections within the cepstrums, according to some implementations of the present disclosure.

Referring to FIG. 21, and as discussed above, the signatures that are used to determine the category of user interface can relate to the primary and secondary reflections in the generated acoustic data. Box 1901 in FIG. 21 indicates portions of the cepstrum that correspond to the primary reflection. Box 1903 in FIG. 21 indicates portions of the cepstrum that correspond to the secondary reflection. The magnitudes of the cepstrum corresponding to the primary reflection may be larger than the magnitudes of the cepstrum corresponding to the secondary reflection. Yet, the shapes of the plots for the primary and secondary reflections are similar. In one or more implementations, signatures in the secondary reflection can be used to confirm signatures in the primary reflection with respect to the category of the user interface. In one or more implementations, the presence/absence of additional reflections (e.g., a secondary reflection and/or tertiary reflection) can be used as a signature for categorizing the user interface. In one or more implementations, the ratio of the secondary reflection (and/or tertiary reflection) with respect to the primary reflection can be used as a signature for categorizing the user interface.

As described with respect to FIG. 14A, categorizing the user interface can be performed as an independent process. Alternatively, in one or more implementations, categorizing the user interface can be performed as part of the method of characterizing the user interface for determining the specific manufacturer, type, model, etc. of the user interface. Categorizing the user interface can be performed before characterizing the user interface. Once the category of the user interface is determined, the category can be used to define a subset of user interfaces from which to characterize the user interface. This can improve the characterization of the user interface by removing user interfaces of different categories that may negatively impact the characterization.

Alternatively, the user interface can first be characterized. Thereafter, the user interface can be categorized. The category of the user interface can be used to verify that the determined user interface manufacturer, type, model, etc. matches with the determined category of the user interface. If the category does not match, the user interface can be characterized again, either taking into consideration or not taking into consideration the category in the characterization process.

In one or more implementations, during the characterizing of the user interface, a confidence score may be determined. The confidence score can be determined based, for example, on how well the user interface is characterized. Depending on the confidence score, the characterized user interface may be categorized for verifying that the category of the user interface matches the type, model, manufacturer, etc. of the user interface. For example, if the confidence score is either below or above a threshold, the user interface can be categorized. The category can then be used to verify the characterization of the user interface. Thus, although the method 400 in FIG. 6 and the method 1200 in FIG. 14A are described in different portions of the specification herein and illustrated in different flow diagrams, in one or more implementations, elements of the methods 400 and 1200 can overlap such that the same step within the same method achieve parallel results in the described methods 400 and 1200.

In some implementations of the present disclosure, analyzing the acoustic data can include estimating the length of the conduit 126. The estimated length of the conduit 126 can be used to define the analysis window of the acoustic data (e.g., the window of acoustic data used to characterize and/or categorize the user interface after the acoustic data is windowed).

Referring back to FIGS. 5, 6, 14A, and 14B, the microphone 140 can detect the reflections 310 due to the feature 304, as well as a variety of other reflections of the acoustic signal 302. In some implementations, the reflections 310 can be used to determine the length of the conduit. The acoustic data that is representative of the acoustic reflections 310 can be used to generate time-domain intensity signal. The time-domain intensity signal is a measure of the intensity and/or amplitude of the reflections 310 over a time period, as measured by the microphone 140. The time-domain intensity signal can be converted into a frequency-domain intensity signal, which in turn can be used to determine the length of the conduit 126. The length of the conduit 126 can be used to aid in windowing the acoustic data, and/or in identifying an acoustic signature of the user interface 124.

In some implementations, the acoustic data represents a plurality of reflections from a plurality of acoustic signals, and thus the time-domain intensity signal can represent the reflections of more than just the acoustic signal 302. For example, reflections from each of a plurality of acoustic signals can be averaged together, and the time-domain intensity signal can be generated from this average.

Figure 24A:
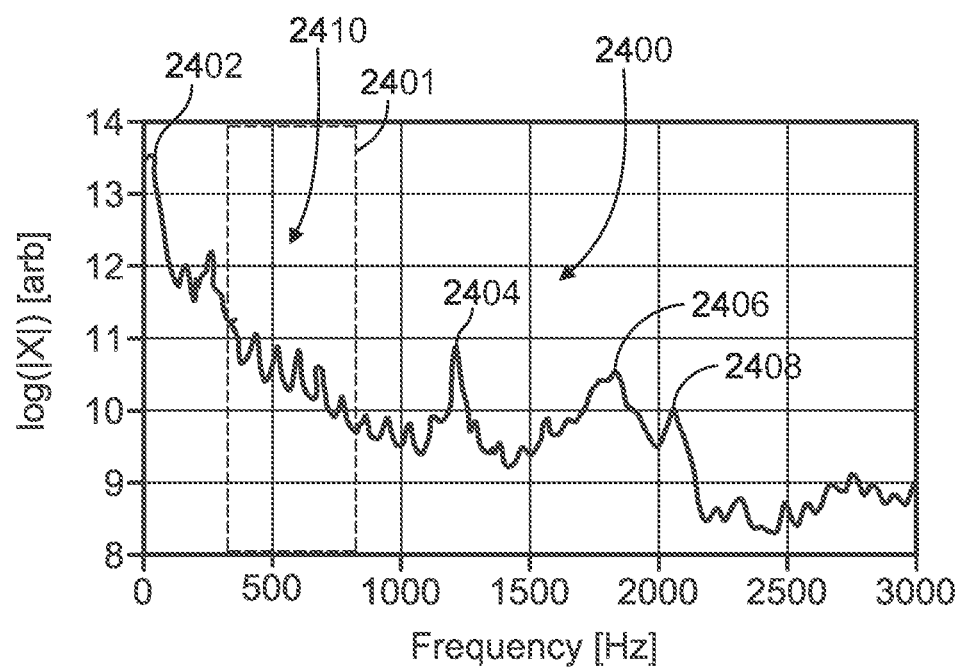
FIG. 24A illustrates a plot of a frequency-domain intensity signal based on the generated acoustic data, according to some implementations of the present disclosure.

FIG. 24A shows a plot of a frequency-domain intensity signal 2400 that can be obtained from the time-domain intensity signal. In some implementations, the frequency-domain intensity signal 2400 can be obtained from the time-domain intensity signal by taking the Fourier Transform of the time-domain intensity signal. The frequency-domain intensity signal 2400 represents the intensity of various different frequencies of the acoustic reflections 310 across a frequency band. Thus, the frequency-domain intensity signal 2400 shows the frequency spectrum of the reflections 310 of the acoustic signal 302. In FIG. 24A, the Y-axis represents the absolute value of the intensity of the reflection 310, denoted as |x|. The intensity is plotted on a log-scale, using arbitrary units. The X-axis represents the frequency of the reflections 310, measured in Hertz (Hz). In some implementations, the intensity is plotted on an absolute scale instead of a log-scale.

The frequency-domain intensity signal 2400 in FIG. 24A represents the various frequencies of the reflections 310 from the acoustic signal 302. The acoustic signal 302 and the reflections 310 form standing waves within the conduit 126 and/or the user interface 124. The conduit 126 can support standing waves at a variety of different frequencies therein. Generally, the lowest frequency of standing wave that is supported by the conduit 126 is referred to as the resonant frequency.

The wavelength of a standing wave at the resonant frequency can be obtained from the resonant frequency, and is generally equal to $2L_C$, where $L_C$ is the length of the conduit 126. The intensity of a standing wave propagating within the conduit 126 at the resonant frequency is generally larger than the intensities of standing waves propagating within the conduit 126 at frequencies other than the resonant frequency.

The frequency-domain intensity signal 2400 shows the intensity of standing waves propagating within the conduit 126 that have a variety of different frequencies. The peaks in the frequency-domain intensity signal 2400 correspond to different standing waves supported within the conduit 126. However, because the conduit 126 is coupled to both the respiratory device 122 and the user interface 124, the frequency-domain intensity signal 2400 also represents standing waves that partially propagate within the respiratory device 122, the user interface 124, or both. Thus, some of the peaks of the frequency-domain intensity signal 2400 correspond to standing waves that propagate partially within the respiratory device 122, the user interface 124, or both.

For example, the frequency-domain intensity signal 2400 includes a peak 2402 at a low frequency, that is larger than the rest of the peaks of the frequency-domain intensity signal 2400. Peak 2402 can correspond to a standing wave that propagated primarily within the respiratory device 122. The frequency-domain intensity signal 2400 also includes peaks 2404, 2406, and 2408 that represent standing waves that at least partially propagate within the user interface 124. Finally, the frequency-domain intensity signal 2400 includes a series of peaks 2410 that are located within portion 2401 of the frequency-domain intensity signal 2400. As is shown in FIG. 24A, the peaks 2410 are arranged in a generally periodic series of peaks that have decreasing intensities. The series of peaks 2410 primarily correspond to standing waves propagating at the resonant frequency of the conduit 126, and higher order harmonics of the resonant frequency, although the peaks 2410 may also correspond to standing waves propagating at the resonant frequency of the user interface 124 and higher order harmonics thereof. These higher order harmonics are standing waves with a wavelength that is equal to $2L_{C/n}$, where n is a positive integer greater than or equal to two.

Figure 24B:
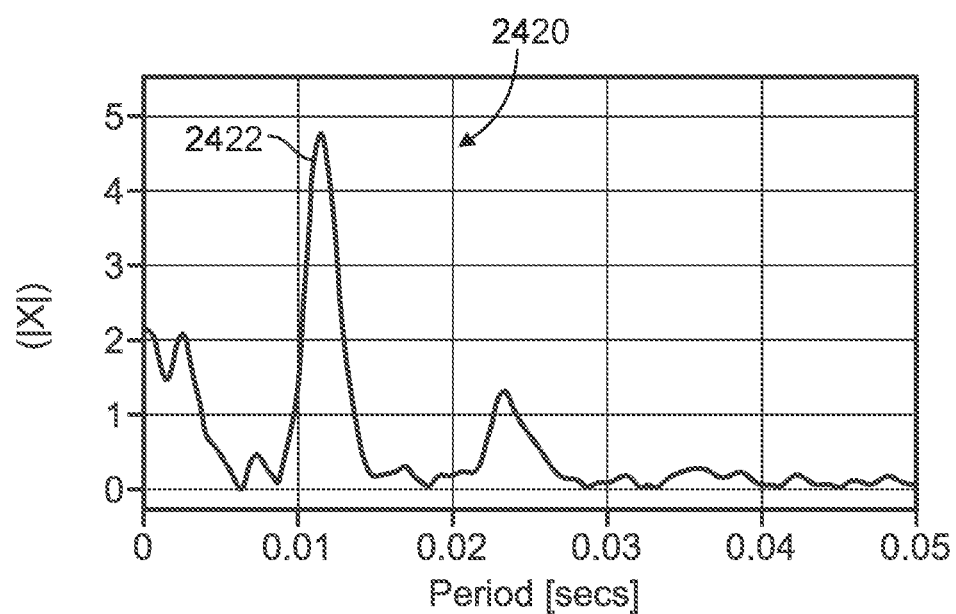
FIG. 24B illustrates a plot of a wave period intensity signal based on the frequency-domain intensity signal of FIG. 24A, according to some implementations of the present disclosure.

FIG. 24B shows a plot of a wave period intensity signal 2420 that can be obtained from the frequency-domain intensity signal 2400. In some implementations, the wave period intensity signal 2420 is obtained by taking the Fourier transform of the portion 2401 of the frequency-domain intensity signal 2400 that contains the periodic series of peaks 2410. The wave period intensity signal 2420 plots the intensity of the reflections 310 within the portion 2401 of the frequency-domain intensity signal, against the period of the standing waves. The Y-axis of the plot represents the intensity of the reflections 310, denoted as |x|. The intensity is plotted on an absolute scale. The X-axis represents the period of the reflections 310 within portion 2401 of the frequency-domain intensity signal 2400, measured in seconds. (e.g., the inverse of the frequency).

As shown, the wave period intensity signal 2420 contains a peak 2422 that is substantially larger than the other peaks in the wave period intensity signal 2420. Because peak 2422 is larger than the other peaks, peak 2422 corresponds to the standing wave propagating at the resonant frequency of the conduit 126. The location of the peak 2422 along the X-axis represents the period of the standing wave propagating at the resonant frequency. By taking the inverse of the period of this standing wave, the resonant frequency can be determined. In turn, the wavelength λ of this standing wave is generally equally to V/f, where v is the speed of sound within the conduit 126. In some implementations, the speed of sound v is based at least in part on the temperature and/or the humidity of the air within the conduit 126. Once the wavelength of the standing wave propagating at the resonant frequency is known, the length of the conduit 126 can be determined from $\lambda=2L_C$ is the inverse of its frequency. Thus, the length of the conduit 126 is proportional to the wavelength of a standing wave propagating at the resonant frequency, and inversely proportional to the resonant frequency.

In some implementations, a peak different than peak 2422 may be selected as the peak representing the resonant frequency of the conduit 126. For example, due to the presence of the respiratory device 122 and/or the user interface 124, the intensities of standing waves propagating at frequencies other than the resonant frequency may appear larger than the peak that actually represents the resonant frequency of the standing wave. In these cases, the lowest frequency peak of the wave period intensity signal 2420 may be selected as representing the resonant frequency of the conduit 126.

Taking the Fourier Transform of the initial time-domain intensity signal and of the frequency-domain intensity signal 2400, along with any pre-processing steps, generally minimizes the noise in the data, to allow the resonant frequency of the conduit to be identified more easily. However, in some implementations, the resonant frequency can be identified from the frequency-domain intensity signal 2400, instead of from the wave period intensity signal. For example, after identifying the series of peaks 2410 in the frequency-domain intensity signal 2400, the resonant frequency may be selected directly from these series of peaks 2410. The peak of the series of peaks 2410 having the lowest frequency can be selected as representing the resonant frequency of the conduit 126.

In some implementations, the frequency-domain intensity signal 2400 can itself be windowed prior to obtaining the wave period intensity signal 2420. In these implementations, a portion of the frequency-domain intensity signal that is expected to include the resonant frequency of the conduit 126 is selected, and that wave period intensity signal 2420 is obtained only from this selected portion. By identifying the portion of the frequency-domain intensity signal expected to include the resonant frequency, the additional portions of the frequency-domain intensity signal are removed, which reduces the complexity present when analyzing the acoustic data. The selection of the portion of the frequency-domain intensity signal that contains the resonant frequency can be based on a variety of factors. In some implementations, a predetermined estimate of the length of the conduit 126 is used to provide the frequency range within which the resonant frequency is expected to fall. For example, if it is known that the conduit 126 is generally between 1.5 meters and 2.0 meters, those length estimates can be used to estimate the portion of the frequency-domain intensity signal where the resonant frequency is expected to be. Additionally or alternatively, the estimate can be based on the speed of sound within the conduit 126, the sampling rate of the of the acoustic data, known conditions both internal to the conduit 126 and external to the conduit 126 (such as the temperature or humidity, which can affect the speed of sound within the conduit 126), and other factors can be used by the skilled person in the art to estimate the portion of the frequency-domain intensity signal within which the resonant frequency exists.

In some implementations, instead of applying a Fourier Transform to the frequency-domain intensity signal to obtain the wave period intensity signal, other transformations and/or analyses may be applied. For example, an inverse Fourier Transform can be applied to the frequency-domain intensity signal 2400 to obtain a new time-domain intensity signal, and the resonant frequency can be identified from the new time-domain intensity signal. In another example, a cross-correlation analysis can be applied to the initial time-domain intensity signal and the frequency-domain intensity signal 2400, in order to determine the resonant frequency of the conduit 126.

In some implementations, a variety of different pre-processing steps can be applied to the frequency-domain intensity signal or to the wave period intensity signal. In one implementation, the pre-processing includes de-trending, which can remove any fluctuations in the frequency-domain intensity signal unrelated to the length of the conduit 126. For example, the acoustic data may include artifacts (such as peaks, dips, etc.) due to physical characteristics of components other than the conduit 126, external noise and/or disturbances, data noise, etc. In additional or alternative implementations, the pre-processing includes spectral windowing. Spectral windowing can be used to improve the quality of the frequency-domain intensity signal, which is the Fourier Transform of the time-domain intensity signal. In some cases, the Fast Fourier Transform algorithm applied to the time-domain intensity signal can lead to various artifacts and other errors in the frequency-domain intensity signal. For example, if the endpoints of the time-domain intensity signal are discontinuous, the frequency-domain intensity signal may be slightly altered from the actual frequency-domain version of the time-domain intensity signal. Spectral windowing can be used to correct for the discontinuities in the endpoints of the time-domain intensity signal, so that the frequency-domain intensity signal more accurately represents the actual frequency spectrum of the reflections of the acoustic signal.

Thus, when windowing the generated acoustic data at step 404 of method 400, the windowing of the generated acoustic data can be based at least in part on the length of the conduit 126 as determined according to FIGS. 24A and 24B. By determining the length of the conduit 126, the approximate location on the x-axis of a cepstrum where the conduit 126 ends and the user interface 124 begins can be identified. This location can then be used to define the analysis window for the acoustic data (e.g., can be used to window the acoustic data). The windowed acoustic data can then be used to characterize the user interface 124, as is discussed herein. In some implementations, the length of the conduit 126 can first be estimated using these techniques to provide an estimate of the location of the user interface 124. Then, one or more fiducial points can be identified based on the estimated location of the user interface 124, and further analysis of the user interface 124 and/or the conduit 126 can be performed. The fiducial points can be identified and the user interface 124 and/or the conduit 126 can be analyzed as is discussed herein. Moreover, the determined length of the conduit 126 can also be used as part of any acoustic signature that ads in characterizing and/or categorizing the user interface 124. In further implementations, the length of the conduit 126 can be estimated using techniques other than those discussed herein with respect to FIGS. 24A and 24B.

Referring now to FIGS. 25A and 25B, the determined length of the conduit 126 can be also used to adjust a characterization of the user interface 124, based on the acoustic data. When analyzing the user interface 124, identifying features of the user interface 124, and characterizing and/or categorizing the user interface 124 as discuss herein, the length of the conduit 126 is assumed. However, the conduit 126 may have a length that is different than expected, for example due to manufacturing tolerances, different designs, stretching, damage, etc. Moreover, the apparent effective length of the conduit 126 can vary due to the amount of time it takes for sound to travel through the conduit 126. This amount of time can vary based on air temperature, humidity, the position/orientation of the conduit 126, etc. If the conduit 126 has a length (actual or apparent) that is different than expected, any acoustic signatures identified using the techniques discussed herein may be unexpectedly distorted or warped, such that the identified acoustic signatures cannot be correlated with the user interface 124 that is being tested/used by the user. Thus, unexpected lengths of the conduit 126 can diminish the accuracy of any characterization and/or categorization of the user interface 124, and various aspects related to characterizing and/or categorizing the user interface 124 may need to be adjusted based on the length of the conduit 126.

FIG. 25A shows an upper plot of cepstrum 2500A, and a lower plot of a cepstrum 2500B. Cepstrum 2500A was determined from acoustic data generated a user interface 124 and a first type of conduit 126. Cepstrum 2500B was determined from acoustic data generated from the same user interface 124, but a second type of conduit 126. For example, the first type of conduit 126 can be a ResMed® SlimLine® conduit, while the second type of conduit 126 can be a ResMed® ClimateLine® conduit. The first and second type of conduits 126 have different lengths.

The cepstrums 2500A and 2500B are shown with quefrency on the X-axis and amplitude on the Y-axis. In these implementations, the quefrency corresponds to a measure of distance along the pathway through which the acoustic signal propagates. The cepstrums 2500A and 2500B are thus used to show the distances along this pathway that are associated with reflections of the acoustic signal. The reflections in turn are associated with various features of the user interface. Thus, the cepstrums 2500A and 2500B can be used to characterize and/or categorize the respective user interfaces 124. While the illustrated implementation shows using cepstrums to characterize and/or categorize the user interface 124, the analysis of the acoustic data can generally include performing any deconvolution of the acoustic data. The deconvolution of the acoustic data can then be used to characterize and/or categorize the user interface 124. A cepstrum is a specific type of deconvolution that can be utilized.

Because the two cepstrums 2500A and 2500B are determined from acoustic data generated using the same user interface 124, the two cepstrums 2500A and 2500B should generally have the same pattern. However, the different lengths of the conduit 126 result in cepstrum 2500B being distorted. As shown in FIG. 25A, cepstrum 2500B is stretched or smeared relative to cepstrum 2500A. For example, cepstrum 2500B includes a peak 2502B that is positioned forward relative to a corresponding peak 2502A of cepstrum 2500A, due to the stretching or smearing of cepstrum 2500B. The distortion of cepstrum 2500B due to the different length of the conduit can also impact the position of the peaks along the Y-axis. If cepstrum 2500B is stretched relative to what would be expected from the expected length of the conduit 126 used to obtain cepstrum 2500B, the peaks may be shorter along the Y-axis than they would otherwise be. Conversely, if the length of the conduit 126 was shorter than expected, the cepstrum 2500B could be compressed relative to normal, and the peaks may be taller along the Y-axis than they would otherwise be. Thus, any features of the user interface 124 obtainable from cepstrum 2500B will be different than features of the user interface 124 obtainable from to cepstrum 2500A, even though both cepstrums were generated using the same user interface 124. Thus, as shown in FIG. 25A, the length of the conduit 126 can negatively affect the characterization of the user interface 124.

FIG. 25B shows an upper plot of a corrected cepstrum 2504A, and a lower plot of a corrected cepstrum 2504B. Cepstrum 2504A is a corrected version of cepstrum 2500A and includes a peak 2506A. Cepstrum 2504B is a corrected version of cepstrum 2500B and includes a peak 2506B. The cepstrums 2504A and 2504B have been corrected by scaling the cepstrums 2500A and 2500B by a factor equal to the ratio of (i) the measured length of each respective conduit 126 to (ii) the assumed length of the conduits 126. For example, if a particular conduit was assumed to be 2 meters long, and the analysis of the conduit revealed that the conduit was actually 1.8 meters long, the new position along the X-axis of each data point of the cepstrum would be equal to the old position along the X-axis, multiplied by 1.8/2. As shown in FIG. 25B, peak 2506A of the corrected cepstrum 2504A is now aligned with peak 2506B of the corrected cepstrum 2504B, which is expected if the actual lengths of the conduits 126 are the same.

In the illustrated implementation, both cepstrums 2500A and 2500B were scaled to the same length, remove the stretching effect caused by the unknown length of the conduit. If the two conduits 126 and their respective user interfaces 124 are being compared, scaling to the same assumed length can allow for an easier comparison. However, any cepstrum generated from acoustic data can generally be scaled to any desired length. For example, in some implementations, two conduits 126 that are assumed to have two different lengths may each be scaled to their respective assumed length, even if those lengths are different. In generally, a cepstrum can be scaled to its assumed length to remove any distortion caused by the actual length of the conduit 126. As discussed herein, this distortion can include the cepstrum being stretched, and the cepstrum being compressed.

Thus, the acoustic data used to characterize and/or categorize the conduit 126 can be stretched and/or compressed to compensate for differences in the effective length of the conduit 126, so that the length of the conduit 126 does not distort the characterization and/or categorization of the user interface 124. This scaling (e.g., stretching and/or compressing) of the acoustic data can be performed in the time domain (time signals), the frequency domain (spectrum), the quefrency domain (cepstrum), any other domain, or any combination of domains. The scaling can be performed on spectrums and/or cepstrums, logarithms of spectrums and/or cepstrums, direct transforms of spectrums and/or cepstrums, direct transforms of logs of spectrums and/or cepstrums, inverse transforms of spectrums and/or cepstrums, inverse transforms of logs of spectrums and/or cepstrums, or any other data set. The scaling can also be performed on the acoustic data itself before any operations or transformations have been performed on the acoustic data. The scaling can be performed using a variety of signal processing methods, such as interpolation, up-sampling, phase-vocoding techniques (which allow for the control of the frequency shift to be applied to a signal), etc. The scaling can thus be used to aid in characterizing the user interface 124 as discussed herein with respect to method 400 and FIG. 6, and to aid in categorizing the user interface 124 as discussed herein with respect to method 1200 and FIGS. 14A and 14B.

Additional details related to determining the length of the conduit 126 and/or identifying the conduit 126 can be found in U.S. Provisional App. No. 63/107,763 filed on Oct. 30, 2020, which is hereby incorporated by reference herein in its entirety.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments. Rather, the scope of the invention should be defined in accordance with the following claims and their equivalents.

One or more elements or aspects or steps, or any portion (s) thereof, from one or more of any of the claims below can be combined with one or more elements or aspects or steps, or any portion(s) thereof, from one or more of any of the other claims below or combinations thereof, to form one or more additional implementations and/or claims of the present disclosure.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A method comprising:
generating acoustic data associated with an acoustic reflection of an acoustic signal, the acoustic reflection being indicative of, at least in part, one or more features of a user interface, a conduit, or both, wherein the user interface is coupled to a respiratory therapy device via the conduit;
analyzing the generated acoustic data, the analyzing including calculating a deconvolution of the generated acoustic data, the calculating of the deconvolution of the generated acoustic data including calculating a cepstrum of the generated acoustic data and further calculating a derivative of the cepstrum to determine a rate of change of the cepstrum signal, the analyzing including windowing the generated acoustic data based, at least in part, on at least one feature of the one or more features of the user interface, the conduit, or both, the windowing the generated acoustic data including a first windowing of the generated acoustic data based on a first window size and relative to the at least one feature and a second windowing of the generated acoustic data based on a second window size and relative to the at least one feature, with the second window size being larger than the first window size; and
characterizing the user interface based, at least in part, on the analyzed acoustic data of the second windowing.

2. The method of claim 1, wherein the first windowing captures the generated acoustic data associated with about 10 cm before and after the at least one feature and the second windowing captures the generated acoustic data associated with about 35 cm before and about 50 cm after the at least one feature.

3. The method of claim 1, wherein the windowing of the generated acoustic data includes determining a fiducial point in the generated acoustic data, and the fiducial point is a minimum or maximum point within a predetermined section of the deconvolution of the generated acoustic data.

4. The method of claim 3, wherein the fiducial point corresponds to a location of the one or more features along a pathway formed, at least in part, by the conduit and the user interface.

5. The method of claim 4, wherein the one or more features cause a change in acoustic impedance based, at least in part, on a narrowing or a widening of the pathway at (i) the user interface, (ii) a junction of the conduit and the user interface, or (iii) a combination thereof.

6. The method of claim 1,
wherein the first windowing and the second windowing vary by an amount of the generated acoustic data selected before a fiducial point in the generated acoustic data, after the fiducial point in the generated acoustic data, or a combination thereof.

7. The method of claim 1, wherein the cepstrum identifies a distance associated with the acoustic reflection, the distance indicating a location of the one or more features of the user interface.

8. The method of claim 1, wherein the analyzing of the generated acoustic data includes normalizing the generated acoustic data by subtracting a mean value from the generated acoustic data, dividing by a standard deviation of the generated acoustic data, or a combination thereof.

9. The method of claim 1, wherein the characterizing of the user interface includes inputting the analyzed acoustic data into a convolutional neural network to determine a form factor of the user interface, a model of the user interface, a size of one or more elements of the user interface, or a combination thereof.

10. The method of claim 9, wherein the convolutional neural network includes N features with a max pooling of M samples of the N features, and the ratio of N to M is 1:1 to 4:1.

11. The method of claim 1, further comprising emitting the acoustic signal into the conduit connected to the user interface via an audio transducer or via a motor of the respiratory therapy device connected to the conduit.

12. The method of claim 11, wherein the acoustic signal is an ultrasonic sound.

13. The method of claim 1, wherein the user interface is not connected to a user during the generating of the acoustic data.

14. The method of claim 1, further comprising providing a flow of pressurized air through the conduit and into the user interface during the generating of the acoustic data.

15. The method of claim 1, wherein the acoustic reflection of the acoustic signal includes a plurality of acoustic reflections from a plurality of acoustic signals, and wherein the generated acoustic data is an average of the plurality of acoustic reflections from the plurality of the acoustic signals.

16. The method of claim 1, wherein the analyzing the generated acoustic data includes identifying one or more signatures that correlate to the one or more features of the user interface, the method further comprising:
categorizing the user interface based, at least in part, on the one or more signatures.

17. The method of claim 16, wherein the user interface is characterized from a subset of user interfaces determined based, at least in part, on the category of the user interface.

18. The method of claim 16, further comprising:
verifying the characterized user interface based, at least in part, on the characterized user interface satisfying the category of the user interface.

19. The method of claim 18, further comprising:
determining a confidence score that the user interface is characterized correctly,
wherein the verifying the characterized user interface occurs when the confidence score satisfies a confidence threshold.

20. A system comprising:
a memory storing machine-readable instructions; and
a control system including one or more processors configured to execute the machine-readable instructions to:
generate acoustic data associated with an acoustic reflection of an acoustic signal, the acoustic reflection being indicative of, at least in part, one or more features of a user interface, a conduit, or both, wherein the user interface is coupled to a respiratory therapy device via the conduit;
analyze the generated acoustic data, the analyzing including calculating a deconvolution of the generated acoustic data, the calculating of the deconvolution of the generated acoustic data including calculating a cepstrum of the generated acoustic data and further calculating a derivative of the cepstrum to determine a rate of change of the cepstrum signal, the analyzing including windowing the generated acoustic data based, at least in part, on at least one feature of the one or more features of the user interface, the conduit, or both, the windowing the generated acoustic data including a first windowing of the generated acoustic data based on a first window size and relative to the at least one feature and a second windowing of the generated acoustic data based on a second window size and relative to the at least one feature, with the second window size being larger than the first window size; and characterize the user interface based, at least in part, on the analyzed acoustic data of the second windowing.

21. The system of claim 20, wherein the first windowing captures the generated acoustic data associated with about 10 cm before and after the at least one feature and the second windowing captures the generated acoustic data associated with about 35 cm before and about 50 cm after the at least one feature.

22. The system of claim 20, wherein the windowing of the generated acoustic data includes determining a fiducial point in the generated acoustic data, and the fiducial point is a minimum or maximum point within a predetermined section of the deconvolution of the generated acoustic data.

23. The system of claim 22, wherein the fiducial point corresponds to a location of the one or more features along a pathway formed, at least in part, by the conduit and the user interface.

24. The system of claim 23, wherein the one or more features cause a change in acoustic impedance based, at least in part, on a narrowing or a widening of the pathway at (i) the user interface, (ii) a junction of the conduit and the user interface, or (iii) a combination thereof.

25. The system of claim 20,
wherein the first windowing and the second windowing vary by an amount of the generated acoustic data selected before a fiducial point in the generated acoustic data, after the fiducial point in the generated acoustic data, or a combination thereof.

26. The system of claim 20, wherein the cepstrum identifies a distance associated with the acoustic reflection, the distance indicating a location of the one or more features of the user interface.

27. The system of claim 20, wherein the analyzing of the generated acoustic data includes normalizing the generated acoustic data by subtracting a mean value from the generated acoustic data, dividing by a standard deviation of the generated acoustic data, or a combination thereof.

28. The system of claim 20, wherein the characterizing of the user interface includes inputting the analyzed acoustic data into a convolutional neural network to determine a form factor of the user interface, a model of the user interface, a size of one or more elements of the user interface, or a combination thereof.

29. The system of claim 28, wherein the convolutional neural network includes N features with a max pooling of M samples of the N features, and the ratio of N to M is 1:1 to 4:1.

30. The system of claim 20, wherein the one or more processors further are configured to execute the machine-readable instructions to cause an emitting of the acoustic signal into the conduit connected to the user interface via an audio transducer or via a motor of the respiratory therapy device connected to the conduit.

31. The system of claim 30, wherein the acoustic signal is an ultrasonic sound.

32. The system of claim 20, wherein the user interface is not connected to a user during the generating of the acoustic data.

33. The system of claim 20, wherein the one or more processors further are configured to execute the machine-readable instructions to generate the acoustic data during a providing of a flow of pressurized air through the conduit and into the user interface.

34. The system of claim 20, wherein the acoustic reflection of the acoustic signal includes a plurality of acoustic reflections from a plurality of acoustic signals, and wherein the generated acoustic data is an average of the plurality of acoustic reflections from the plurality of the acoustic signals.

35. The system of claim 20, wherein the analyzing the generated acoustic data includes identifying one or more signatures that correlate to the one or more features of the user interface, the method further comprising:
categorizing the user interface based, at least in part, on the one or more signatures.

36. The system of claim 35, wherein the user interface is characterized from a subset of user interfaces determined based, at least in part, on the category of the user interface.

37. The system of claim 35, wherein the method further comprises:
verifying the characterized user interface based, at least in part, on the characterized user interface satisfying the category of the user interface.

38. The system of claim 37, wherein the method further comprises:
determining a confidence score that the user interface is characterized correctly,
wherein the verifying the characterized user interface occurs when the confidence score satisfies a confidence threshold.

* * * * *